(12) United States Patent
Zhou et al.

(10) Patent No.: US 11,117,865 B2
(45) Date of Patent: Sep. 14, 2021

(54) INHIBITORS OF BROMODOMAIN-CONTAINING PROTEIN 4 (BRD4)

(71) Applicants: Jia Zhou, Austin, TX (US); Allan R. Brasier, Austin, TX (US); Bing Tian, Austin, TX (US); Zhiqing Liu, Austin, TX (US); Haiying Chen, Austin, TX (US); Erik Rytting, Austin, TX (US)

(72) Inventors: Jia Zhou, Austin, TX (US); Allan R. Brasier, Austin, TX (US); Bing Tian, Austin, TX (US); Zhiqing Liu, Austin, TX (US); Haiying Chen, Austin, TX (US); Erik Rytting, Austin, TX (US)

(73) Assignee: Board of Regents, The University Of Texas System, Austin, TX (US)

( * ) Notice: Subject to any disclaimer, the term of this patent is extended or adjusted under 35 U.S.C. 154(b) by 118 days.

(21) Appl. No.: 16/442,526

(22) Filed: Jun. 16, 2019

(65) Prior Publication Data
US 2019/0359573 A1    Nov. 28, 2019

Related U.S. Application Data

(63) Continuation of application No. PCT/US2017/066107, filed on Dec. 13, 2017.
(Continued)

(51) Int. Cl.
*A61K 9/14* (2006.01)
*A61P 29/00* (2006.01)
(Continued)

(52) U.S. Cl.
CPC .......... *C07D 215/38* (2013.01); *A61K 9/14* (2013.01); *A61P 29/00* (2018.01); *C07D 207/48* (2013.01);
(Continued)

(58) Field of Classification Search
CPC . A61K 9/14; A61P 29/00; A61P 37/00; C07C 2601/08; C07C 311/37;
(Continued)

(56) References Cited

U.S. PATENT DOCUMENTS

| | | | |
|---|---|---|---|
| 4,668,218 A | 5/1987 | Virtanen | |
| 5,458,135 A | 10/1995 | Patton et al. | |

(Continued)

FOREIGN PATENT DOCUMENTS

| | | |
|---|---|---|
| EP | 0237507 | 9/1987 |
| WO | WO 94/06498 | 3/1994 |

(Continued)

OTHER PUBLICATIONS

Extended European Search Report and Opinion issued in correspondence European Patent Application No. 17881997.5, dated Apr. 7, 2020.
(Continued)

*Primary Examiner* — Ernst V Arnold

(57) ABSTRACT

Certain embodiments are directed to small molecule selective inhibitors of the BRD4 bromodomain. Compounds described herein can be used to modulate the bronchiolar NFkB-BRD4 axis, which plays a role in acute neutrophilic response to viral molecular patterns. Compounds described herein can be developed as preventive and therapeutic agents for various human diseases and conditions.

4 Claims, 10 Drawing Sheets

Specification includes a Sequence Listing.

Related U.S. Application Data

(60) Provisional application No. 62/435,421, filed on Dec. 16, 2016.

(51) Int. Cl.

| | | |
|---|---|---|
| *C07D 311/00* | (2006.01) | |
| *C07D 215/38* | (2006.01) | |
| *C07D 207/48* | (2006.01) | |
| *C07D 241/04* | (2006.01) | |
| *C07D 311/30* | (2006.01) | |
| *C07D 401/06* | (2006.01) | |
| *C07D 401/12* | (2006.01) | |
| *C07D 401/14* | (2006.01) | |
| *C07D 405/12* | (2006.01) | |
| *C07D 413/04* | (2006.01) | |
| *C07D 413/06* | (2006.01) | |
| *C07D 413/14* | (2006.01) | |
| *C07D 471/04* | (2006.01) | |

(52) U.S. Cl.
CPC .......... *C07D 241/04* (2013.01); *C07D 311/30* (2013.01); *C07D 401/06* (2013.01); *C07D 401/12* (2013.01); *C07D 401/14* (2013.01); *C07D 405/12* (2013.01); *C07D 413/04* (2013.01); *C07D 413/06* (2013.01); *C07D 413/14* (2013.01); *C07D 471/04* (2013.01)

(58) Field of Classification Search
CPC .. C07D 207/08; C07D 207/09; C07D 207/16; C07D 207/48; C07D 209/08; C07D 215/38; C07D 241/04; C07D 311/30; C07D 401/06; C07D 401/12; C07D 401/14; C07D 403/12; C07D 405/12; C07D 413/04; C07D 413/06; C07D 413/14; C07D 471/02; C07D 471/04
See application file for complete search history.

(56) References Cited

U.S. PATENT DOCUMENTS

| | | | |
|---|---|---|---|
| 6,488,953 B2 | 12/2002 | Halliday et al. | |
| 6,737,045 B2 | 5/2004 | Patton et al. | |
| 6,794,357 B1 | 9/2004 | Edman et al. | |
| 6,797,258 B2 | 9/2004 | Platz et al. | |
| 2007/0032543 A1* | 2/2007 | Delhomel | C07C 69/738 514/432 |
| 2011/0236437 A1 | 9/2011 | Destache | |
| 2015/0148344 A1 | 5/2015 | Babaoglu et al. | |

FOREIGN PATENT DOCUMENTS

| | | | |
|---|---|---|---|
| WO | WO 94/08552 | 4/1994 | |
| WO | WO 94/16970 | 8/1994 | |
| WO | WO 97/25086 | 7/1997 | |
| WO | WO 98/35888 | 8/1998 | |
| WO | WO-2006045096 A2 * | 4/2006 | ................ A61P 9/10 |
| WO | WO 2014/159837 | 10/2014 | |

OTHER PUBLICATIONS

Raj, et al., "Molecular docking and dynamics simulation study of flavonoids as BET bromodomain inhibitors," *Journal of Biomolecular Structure & Dynamics*, 2016, 35(11):2351-2362.

Alexopoulou et al., "Recognition of double-stranded RNA and activation of NF-κB by Toll-like receptor 3," *Nature*, 413(6857); 732-738, 2001.

Burke et al., "EMS-345541 is a Highly Selective Inhibitor of IkB Kinase That Binds at an Allosteric Site of the Enzyme and Blocks NF-kB-dependent Transcription in Mice," *Journal of Biological Chemistry*, 278(3); 1450-1456, 2003.

Creticos, et al., "Nasal Challenge with Ragweed Pollen in Hay Fever Patients Effect of Immunotherapy," *The Journal of Clinical Investigation*, 76(6); 2247-2253, 1985.

Creticos, et al., "Peptide Leukotriene Release After Antigen Challenge in Patients Sensitive to Ragweed," *New England Journal of Medicine*, 310(25); 1626-1630, 1984.

De Boer et al., "Altered Expression of Epithelial Junctional Proteins in Atopic Asthma: Possible Role in Inflammation," *Canadian Journal of Physiology and Pharmacology*, 86(3); 105-112, 2008.

Fitzgerald, et al., "LPS-TLR4 Signaling IRF-3/7 and Nf-kB Involved the Toll Adapters TRAM and TRIF," *Journal of Experimental Medicine*, 198(7); 1043-1055, 2003.

Fransson, et al., "A Role for Neutrophils in Intermittent Allergic Rhinitis," *Acta Otolaryngologica*, 124(5); 616-620, 2004.

Hosoki, et al., "Facilitation of Allergic Sensitization and Allergic Airway Inflammation by Pollen-Induced Innate Neutrophil Recruitment," *American Journal of Respiratory Cell and Molecular Biology*, 54(1); 81-90, 2016.

Hosoki, et al., "Myeloid Differentiation Protein 2 Facilitates Pollen- and Cat Dander-Induced Innate and Allergic Airway Inflammation," *The Journal of Allergy and Clinical Immunology*, 137(5); 1506-1513, e2, 2016.

Hosoki, et al., "Innate Mechanism of Pollen- and Cat Dander-Induced Oxidative Stress and DNA Damage in the Airways," *The Journal of Allergy and Clinical Immunology*, 1436-1439, 2017.

Huang et al., "Junin Virus Infection Activates the Type I Interferon Pathway in a RIG-I-Dependent Manner," *PLoS Neglected Tropical Diseases*, 6(5); e1659, pp. 1-10, 2012.

Huang et. al., "Early Events in Cell Adhesion and Polarity During Epithelial-Mesenchymal Transition," *Journal of Cell Science*,125(19); 4417-4422, 2012.

Huber et al., "Epithelial-Mesenchymal Transition: NF-κB Takes Center Stage," *Cell Cycle*,3(12); 1477-1480, 2004.

Huber et al., "NFκB Is Essential for Epithelial-Mesenchymal Transition and Metastasis in a Model of Breast Cancer Progression," *Journal of Clinical Investigation*,114(4);569-581, 2004.

Ijaz et al., "Systems Biology Approaches to Understanding Epithelial Mesenchymal Transition (EMT) in Mucosal Remodeling and Signaling in Asthma," *World Allergy Organization Journal*, 7(1);13, 2014.

International Preliminary Report on Patentability Issued in Corresponding PCT Application No. PCT/US2017/066107, dated Jun. 18, 2019.

International Search Report and Written Opinion Issued in Corresponding PCT Application No. PCT/US2017/066107, dated Apr. 24, 2018.

Jang, et al., "The Bromodomain Protein Brd4 is a Positive Regulatory Component of P-TEFb and Stimulates RNAPolymerase II-Dependent Transcription," *Molecular Cell*, 19(4); 523-534, 2005.

Kalita et al., "Systems Approaches to Modeling Chronic Mucosal Inflammation," *Biomedical Research International*, Article 505864, 2013.

Kalluri and Weinberg, "The Basics of Epithelial-Mesenchymal Transition," *Journal of Clinical Investigation*, 119(6);1420-28, 2009.

Kaltenborn, et al., "Respiratory Syncytial Virus Potentiates ABCA3 Mutation-Induced Loss of Lung Epithelial Cell Differentiation," *Human Molecular Genetics*, 21(12); 2793-2806, 2012.

Kim, et al., "Constitutively Active Type I Insulin-Like Growth Factor Receptor Causes Transformation and Xenograft Growth of Immortalized Mammary Epithelial Cells and is Accompanied by an Epithelial-to-Mesenchymal Transition Mediated by NF-κB and Snail," *Molecular and Cellular Biology*, 27(8); 3165-3175, 2007.

Korkaya, et al., "Activation of an IL6 Inflammatory Loop Mediates Trastuzumab Resistance in HER2+ Breast Cancer by Expanding the Cancer Stem Cell Population," *Molecular Cell*, 47; 570-584; 2012.

Lambrecht et al., "The Airway Epithelium in Asthma," *Nature Medicine*, 18(5); 684-692, 2012.

Li et al., "Epithelial-Mesenchyme Transition Induced by TNF-α Requires NF-κB-Mediated Transcriptional Upregulation of Twist1," *Cancer Research*, 72(5); 1290-1300, 2012.

(56) References Cited

OTHER PUBLICATIONS

Liu et al., "Retinoic Acid-Inducible Gene I Mediates Early Antiviral Response and Toll-Like Receptor 3 Expression in Respiratory Syncytial Virus-Infected Airway Epithelial Cells," *Journal of Virology*, 81(3);1401-1411, 2007.
McDonald et al., "Genome-Scale Epigenetic Reprogramming During Epithelial-To-Mesenchymal Transition," *Nature Structural & Molecular Biology*, 18; 867-874, 2011.
Miadonna, et al., "Nasal Response to a Single Antigen Challenge in Patients with Allergic Rhinitis—Inflammatory Cell Recruitment Persists Up To 48 Hours," *Clinical and Experimental Allergy*, 29(7); 941-949, 1999.
Naclerio, et al., "Mediator Release After Nasal Airway Challenge with Allergen," *American Review of Respiratory Disease*, 128(4); 597-602, 1983.
Nowak et al., "RelA Ser276 Phosphorylation is Required for Activation of a Subset of NF-κB-Dependent Genes by Recruiting Cyclin-Dependent Kinase 9/Cyclin T1 Complexes," *Molecular and Cellular Biology*, 28(11); 3623-3638, 2008.
Nowak et al., "Two-Step Cross-Linking Method for Identification of NF-κB Gene Network by Chromatin Immunoprecipitation," *Biotechniques*, 39(5):715-725, 2005.
Pelikan, "Cytological Changes in Nasal Secretions Accompanying Delayed Nasal Response to Allergen Challenge," *American Journal of Rhinology & Allergy*, 27(5); 345-353, 2013.
Peters-Golden, et al., "Cysteinyl Leukotrienes: Multi-functional Mediators in Allergic Rhinitis," *Clinical and Experimental Allergy*, 36(6); 689-703, 2006.
Ramirez, et al., "Immortalization of Human Bronchial Epithelial Cells in the Absence of Viral Oncoproteins," *Cancer Research*, 64(24); 9027-9034, 2004.
Tian, et al., "Analysis of the TGFβ-Induced Program in Primary Airway Epithelial Cells Shows Essential Role of NF-κB/RelA Signaling Network in Type II Epithelial Mesenchymal Transition," 2015, *BMC Genomics*, 16; 529, 2015.
Tian, et al., "Identification of Direct Genomic Targets Downstream of the Nuclear Factor-κB Transcription Factor Mediating Tumor Necrosis Factor Signaling," *Journal of Biological Chemistry*, 280(17); 17435-17448, 2005.
Tian, et al., "Selective Antagonists of the Bronchiolar Epithelial NF-κB-Bromodomain-Containing Protein 4 Pathway in Viral-Induced Airway Inflammation," *Cell Reports*, 23; 1138-1151, 2018.
Tian, et al., "Two-Step Cross-Linking for Analysis of Protein-Chromatic Interactions," *Methods. Mol. Biol.* 809:105-120, 2012.
Zhao, et al., "Quantification of Activated NF-κB/RelA Complexes Using ssDNA Aptamer Affinity—Stable Isotope Dilution—Selected Reaction Monitoring—Mass Spectrometry," *Molecular & Cellular Proteomics*, 10(6); M111, 2011.
Zhao, et al., "Quantitation of the Dynamic Profiles of the Innate Immune Response Using Multiplex Selected Reaction Monitoring-Mass Spectrometry," *Molecular & Cellular Proteomics*, 12(6); 1513-1529, 2013.
Bisgrove et al., "Conserved P-TEFb-Interacting Domain of BRD4 Inhibits HIV Transcription," *PNAS USA*, 104(34); 13690-13695, 2007.
Brasier et al., "RelA Ser276 Phosphorylation-Coupled Lys310 Acetylation Controls Transcriptional Elongation of Inflammatory Cytokines in Respiratory Syncytial Virus Infection," *Journal of Virology*, 85(22); 11752-69, 2011.
Brown et al., NF-κB Directs Dynamic Super Enhancer Formation in Inflammation and Atherogenesis, *Molecular Cell*, 56(2); 219-31, 2014.
Ding et al., "BRD4 is a Novel Therapeutic Target for Liver Fibrosis," *PNAS*, 112(51); 15713-15718, 2015.
Filippakopoulos et al., "Selective Inhibition of BET Bromodomains," *Nature*, 468(7327); 1067-1073, 2010.

Galdeano and Ciulli, "Selectivity on-Target of Bromodomain Chemical Probes by Structure-Guided Medicinal Chemistry and Chemical Biology," *Future Medicinal Chemistry*, 8(13); 1655-1680, 2016.
Ghoshal et al., "BET Inhibitors in Cancer Therapeutics: A Patent Review," *Expert Opinion Therapeutic Patents*, 26; 505-522, 2016.
Greer et al., "Mass Spectrometry Imaging for Drugs and Metabolites," *Journal of Proteomics*, 74(12); 2617-2631, 2011.
Holgate et al., "Epithelial-Mesenchymal Communication in the Pathogenesis of Chronic Asthma," *Proceedings of the American Thoracic Society*, 1(2); 93-8, 2004.
Hruska et al., "Effects of Ribavirin on Respiratory Syncytial Virus in Vitro," *Antimicrobial Agents and Chemotherapy*, 17(5);770-775, 1980.
Kanno et al., "BRD4 Assist Elongation of Both Coding and Enhancer RNAs by Interacting with Acetylated Histones," *Nature Structural & Molecular Biology*, 21(12);1047-57, 2014.
Korb et al., "BET Protein BRD4 Activates Transcription in Neurons and BET Inhibitor Jq1 Blocks Memory in Mice," *Nature Neuroscience*, 18; 1464-73, 2015.
Lai et al., "Inhibition of Respiratory Syncytial Virus Infections with Morpholino Oligomers in Cell Cultures and in Mice," *Molecular Therapy*, 16(6); 1120-1128, 2008.
Leaman, et al., "Targeted Therapy of Respiratory Syncytial Virus in African Green Monkeys by Intranasally Administered 2-5A Antisense," *Virology*, 292(1); 70-77, 2002.
Li, et al., "The BET Bromodomain Inhibitor JQ1 Activates HIV Latency Through Antagonizing BRD4 Inhibition of Tat-Transactivation," *Nucleic Acids Research*, 41; 277-287, 2013.
Lietz, et al., "Qualitative and Quantitative Mass Spectrometry Imaging of Drugs and Metabolites," *Advanced Drug Delivery Review*, 65(8); 1074-1085, 2013.
Liu et al., "Drug Discovery Targeting Bromodomain-Containing Protein 4," *Journal of Medicinal Chemistry*, 60(11); 4533-4558, 2017.
Nicholls, et al., "ApoA-I Induction as a Potential Cardioprotective Strategy: Rationale for the SUSTAIN and ASSURE Studies," *Cardiovascular Drugs and Therapy*, 26; 181-187, 2012.
Pubchem 45582977 created on Jun. 21, 2010, pp. 1-10, p. 3 Retrieved from https://pubchem.ncbi.nlm.nih.gov/compound/45582977.
Rytting et al., "Biodegradable Polymeric Nanocarriers for Pulmonary Drug Delivery," *Expert Opinion on Drug Delivery*, 5(6); 629-639, 2008.
Sagara, et al., "Activation of TGF-Beta/Smad2 Signaling is Associated with Airway Remodeling in Asthma," *Journal of Allergy and Clinical Immunology*, 110(2); 249-54, 2002.
Tian, et al., "BRD4 Mediates NF-κB-Dependent Epithelial-Mesenchymal Transition and Pulmonary Fibrosis via Transcriptional Elongation," *American Journal of Physiology Lung Cellular and Molecular Physiology*, 311(6), 2016.
Tian, et al., "CDK9-Dependent Transcriptional Elongation in the Innate Interferon-Stimulated Gene Response to Respiratory Syncytial Virus Infection in Airway Epithelial Cells," Journal of Virology, 87(12); 7075-7092, 2013.
Wu and Chiang, "The Double Bromodomain-Containing Chromatin Adaptor BRD4 and Transcriptional Regulation," *Journal of Biological Chemistry*, 282(18); 13141-13145, 2007.
Xu and Vakoc, "BRD4 is on the Move During Inflammation," *Trends in Cell Biology*, 24(11): 615-616, 2014.
Yang et al., "The 7SK Small Nuclear RNA Inhibits the CDK9/Cyclin T1 Kinase to Control Transcription," *Nature*, 414(6861); 317-322, 2001.
Zhang, et al., "Discovery of Chemical Inhibitors of Human Bromodomains," *Chemical Review*, 115(121); 11625-11668, 2015 (Figure 7).
Zou, et al., "BRD4 Maintains Constitutively Active NF-κB in Cancer Cells by Binding to Acetylated RelA," *Oncogene*, 33; 2395-2404, 2014.

\* cited by examiner

FIG. 5A
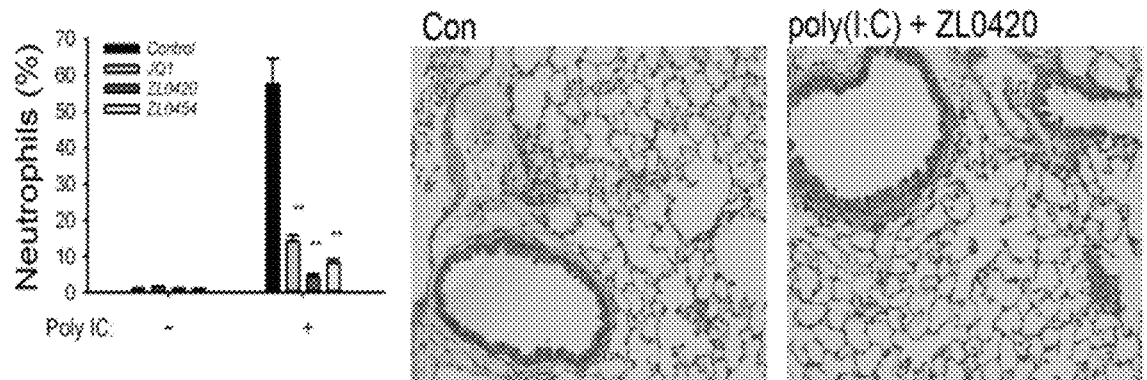
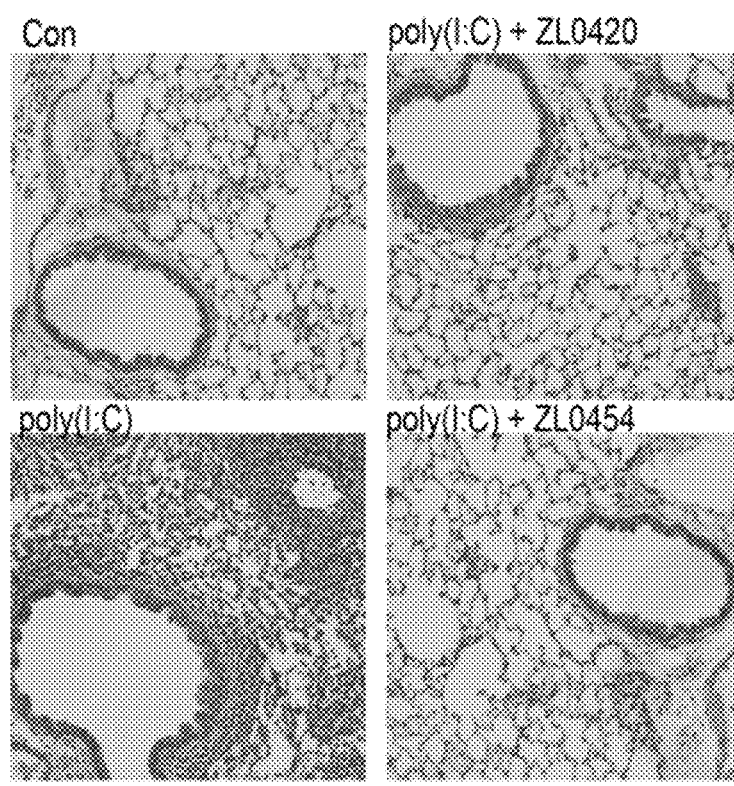
FIG. 5B

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic Primer

<400> SEQUENCE: 1

```
tgcaaacaga cctcctttgt cttga                                25

<210> SEQ ID NO 2
<211> LENGTH: 23
<212> TYPE: DNA
<213> ORGANISM: Artificial Sequence
<220> FEATURE:
<223> OTHER INFORMATION: Synthetic Primer

<400> SEQUENCE: 2
tcctgagacc agactcctcc tcc                                  23
```

INHIBITORS OF BROMODOMAIN-CONTAINING PROTEIN 4 (BRD4)

PRIORITY PARAGRAPH

This Application is a continuation-in-part of International Application PCT/US2017/066107 filed Dec. 13, 2017. This Application also claims priority to U.S. Provisional Patent Application Ser. No. 62/435,421 filed Dec. 16, 2016. Both prior application are incorporated herein by reference in its entirety.

STATEMENT REGARDING FEDERALLY FUNDED RESEARCH

None.

REFERENCE TO SEQUENCE LISTING

A sequence listing required by 37 CFR 1.821-1.825 is being submitted electronically with this application. The sequence listing is incorporated herein by reference.

BACKGROUND

The bromodomain, a highly conserved motif of 110 amino acids, is found in proteins that interact with chromatin, such as histone acetylases, transcription factors and nucleosome remodeling complexes (Zeng and Zhou, *FEBS Lett.* 2002, 513:124-8). Bromodomain-Containing Protein 4 (BRD4), belonging to bromodomain and extra-terminal proteins (BET) family (BRD2, BRD3, BRD4 and BRDT), contains two bromodomains and functions as a chromatin "reader" that binds acetylated lysine in histones (Wu et al., *Mol. Cell* 2013, 49:843-57; Belkina and Denis, *Nat. Rev. Cancer* 2012, 12:465-77). It is an epigenetic reader and a critical regulator of transcription in many cell types. BRD4 plays an important role in the regulation of cell cycle control and transcription elongation mediated by interactions with P-TEFb (Jang et al., *Mol. Cell* 2005, 19:523-34). Oncogene BRD4-NUT has also been detected in tumor tissues (French et al., *Cancer Res.* 2003, 63:304-7). BRD4 is recently identified as a cancer therapeutic target for Basal-like breast cancer (Shi et al., *Cancer cell* 2014, 25:210-25), NUT midline carcinoma (NMC), acute myeloid leukemia, multiple myeloma, Burkitt's lymphoma and so on.

Meanwhile, BRD4 also has an essential role in the induction of inflammatory gene transcription. BRD4 is associated with nuclear factor-κB (NF-κB) signaling pathway via specific binding to acetylated RelA to stimulate NF-κB-dependent inflammatory response (Zou et al., *Oncogene* 2014, 33:2395-404). BRD4 is reported as a potential therapeutic target for patients with fibrotic complications (Ding et al., *Proc. Natl. Acad. Sci. USA* 2015, 112:15713-8). In addition, BRD4 competes with the HIV transactivator protein Tat for PTEFb binding to repress the Tat-mediated transactivation of the HIV promoter (Bisgrove et al., *Proc. Natl. Acad. Sci. USA* 2007, 104:13690-5). BRD4 inhibitors may efficiently reverse latent HIV (Li et al., *Nucleic Acids Res.* 2013, 41:277-87). Furthermore, BRD4 is crucial to neuronal function and mediates the transcriptional regulation underlying learning and memory. The loss of BRD4 function affects critical synaptic proteins, which results in memory deficits in mice but also decrease seizure susceptibility (Korb et al., *Nat. Neurosci.* 2015, 18:1464-73). Most recently, BRD4 was validated as an in vivo target for the treatment of pulmonary fibrosis associated with inflammation-coupled remodeling in chronic lung diseases (Tian et al., *Am J Physiol Lung Cell Mol Physiol.* 2016 Oct. 28). Therefore, targeting BRD4 represents a novel therapeutic method for a variety of different human diseases.

Currently, several different classes of BRD4 inhibitors are under investigation, including benzodiazepines, thienodiazepines, pyridodiazepines, isoxazoles, quinolones, pyrrolopyrrolones, pyrrolopyridines, pyrazolopyridines and pyridopyrazines, which have been reported with moderate to high binding affinities to BRD4 (Liu et al., *J. Med. Chem.* 2017, 60 (11):4533-4558; Zhang et al., *Chem. Rev.* 2015, 115:11625-68; Ghoshal et al., *Expert Opin. Ther. Pat.* 2016, 26:505-22; Galdeano and Ciulli, *Future Med. Chem.* 2016). However, most of them are pan-BET inhibitors instead of BRD4 selective inhibitors. While several of them have been developed into clinical trials, such as RVX-208, I-BET762, OTX-015, TEN-010 and BAY-1238097, none of them has been approved by FDA. A Phase III clinical trial of RVX-208 for high-risk cardiovascular disease patients with type 2 diabetes mellitus and low HDL was initiated in the fall of 2015. The Phase II clinical trial result of RVX-208 in atherosclerosis only showed modest improvement of atherosclerotic plaques (Nicholls et al., *Cardiovasc. Drugs Ther.* 2012, 26:181-7). Other indications of BRD4 inhibitors in various clinical trials include NMC, progressive lymphoma, acute leukemia and other hematological malignancies. It remains an urgent need to identify potent, selective and more drug-like BRD4 inhibitors. Because BET proteins are involved broadly in transcriptional regulation, more selective inhibitors may facilitate to achieve isoform and/or domain specificity to avoid side effects in clinic. Given that JQ1 was reported to cause memory deficits in mice (Korb, et al., *Nat. Neurosci.* 2015, 18:1464-1473), novel potent and specific BRD4 inhibitors that do not cross the blood-brain barrier (BBB) may hold promise as therapeutics benefiting cancer and inflammation or infectious diseases patients, while displaying less risk of neurological adverse effects.

Thus, there remains a need for additional compositions and methods for treating or ameliorating lung disease by synthesizing or administering BRD4 inhibitors to subjects in need thereof.

SUMMARY

The NFκB-BRD4 signaling pathway in airway epithelial cells mediates the acute inflammatory response to a variety of viruses and viral exposures. BRD4 inhibition was shown to completely block poly(I:C) and/or respiratory syncytial virus-induced inflammatory gene programs in vitro, and airway inflammation and neutrophil recruitment in vivo. Small molecule selective inhibitors of the BRD4 bromodomain were designed, synthesized, and demonstrated to be specific for a BRD4 domain (BD) with sub-micromolar affinity. Compounds described herein can be used to modulate the bronchiolar NFκB-BRD4 axis, which plays a role in acute neutrophilic response to viral molecular patterns.

Certain embodiments are directed to compounds of Formula I, or a pharmaceutically acceptable salt thereof.

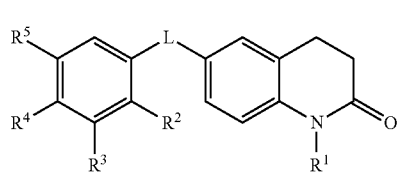

Formula I

Certain aspects are directed to compounds of Formula I wherein: L is —N=N— or —NH(CO)NH—; $R^1$ is H or C1-C4 alkyl or arylalkyl; $R^2$, $R^3$, and $R^5$ are independently H, —OH, alkyl, alkoxy, halogen, —NH$_2$, or —CF$_3$; $R^4$ is —OH, —NH$_2$, —CF$_3$, —(CH$_2$)$_n$R$^6$ where n is 1-4 and $R^6$ is —OH or —NH$_2$, —O(CH$_2$)$_m$R$^7$ where m is 1-4 and $R^7$ is —OH or —NH$_2$; or $R^4$ and $R^5$ are optionally joined to form a 5-6 membered heteroaryl having 1-3 heteroatoms.

In certain aspects are directed to compounds of Formula Ia wherein L is —N=N— and $R^1$ is H. In certain aspects $R^2$, $R^3$, $R^4$, and $R^5$ are as described above.

Formula Ia

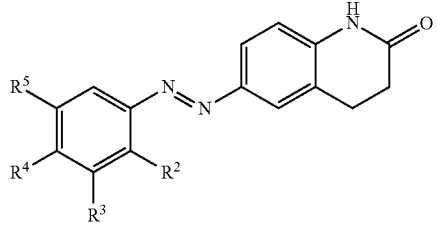

In a further aspect a compound of Formula Ia is ZL0420.

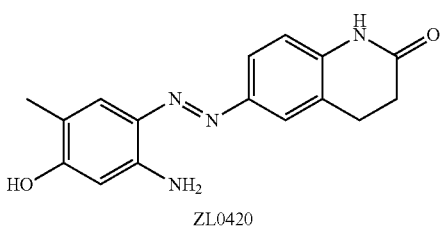 [SMILES: Cc1cc(/N=N/c2ccc3c(c2)CCC(=O)N3)c(N)cc1O]

ZL0420

Further aspects are directed to compounds of Formula Ib, where L is —NH(CO)NH—. In certain aspects $R^2$, $R^3$, $R^4$, and $R^5$ are as described above. A compound of the invention is directed to a compound of Formula Ib wherein $R^1$ is H. In a further aspect $R^4$ is —OH; —(CH$_3$)$_n$R$^6$ where n is 1-4 and $R^6$ is —OH; or —O(CH$_3$)$_m$R$^7$ where m is 1-4 and $R^7$ is —OH.

Formula Ib

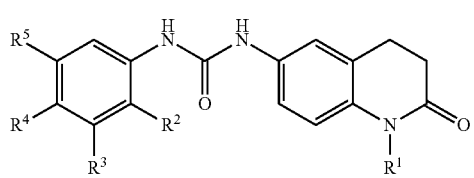

Certain embodiments are directed to compounds having the chemical formula

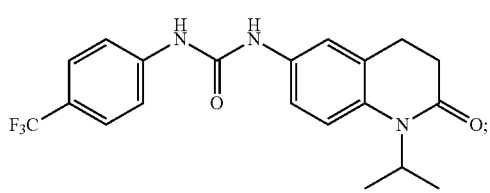

-continued

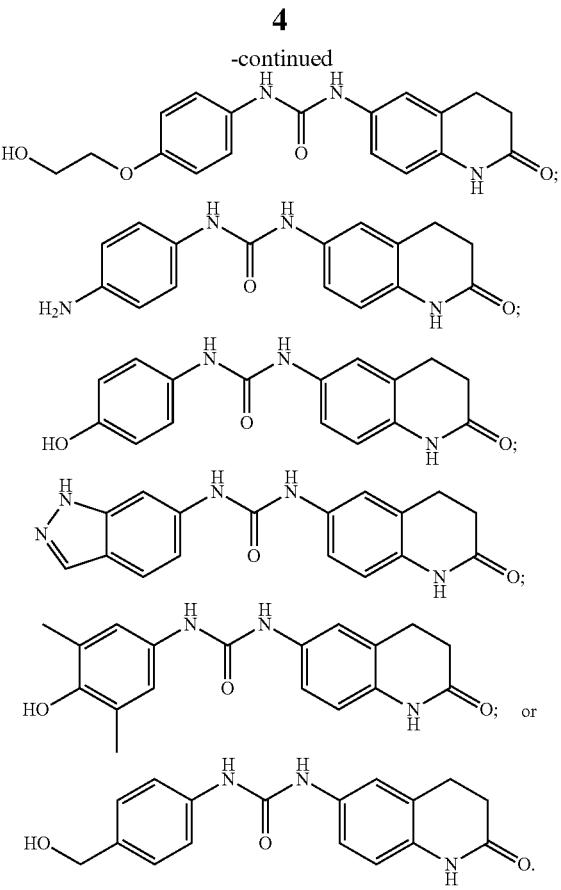

A compound designated ZL0454, or a pharmaceutically acceptable salt thereof, having the structure:

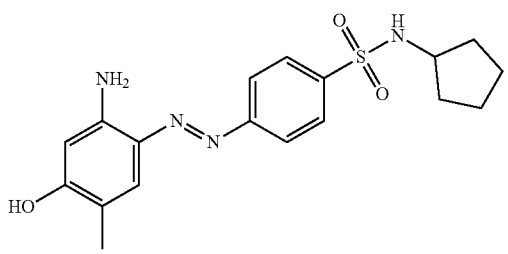

ZL0454

Certain embodiments are directed to compounds of Formula II, or a pharmaceutically acceptable salt thereof.

Formula II

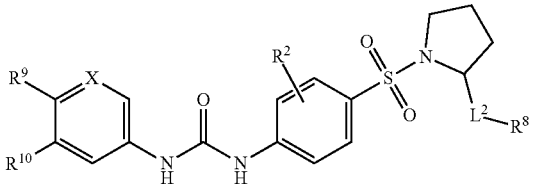

Certain aspects are directed to compounds of Formula II wherein $L^2$ is —CH2— or —(CO)NH—; $R^2$ is as described above. $R^8$ is —OH, —OTs, alkoxy, ester, substituted or unsubstituted aryl, or substituted or unsubstituted 3-7 member heterocycle, or —NR[18]R[19] where R[18] and R[19] are independently H, alkyl; or R[18] and R[19] are optionally joined to form a 3-6 membered substituted or unsubstituted heterocycle having 1-3 heteroatoms; X is C, N, or O; R[9] and R[10] are independently selected from H, —OH, halogen, —CF$_3$, alkyl, hydroxylalkyl, amino, or alkylamino, or R[9] and R[10] are optionally joined to form a 5-6 membered heteroaryl or heterocycle having 1-3 heteroatoms and optionally substituted with one or more substituents selected from alkyl, acetyl, and carbonyl. In certain aspects the X substituent is at position 2, 3, 4, 5, or 6 of Formula II. In a further aspect X is C. In particular aspects a compound of Formula II is

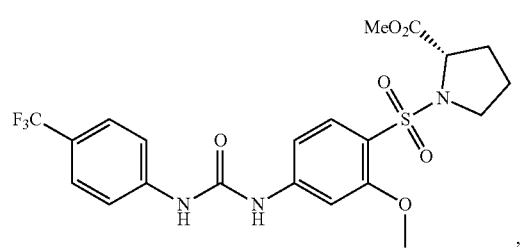

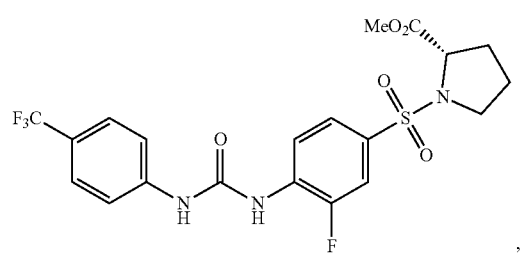

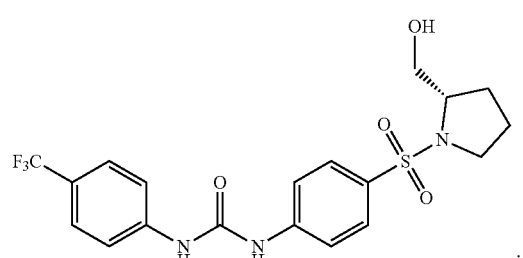

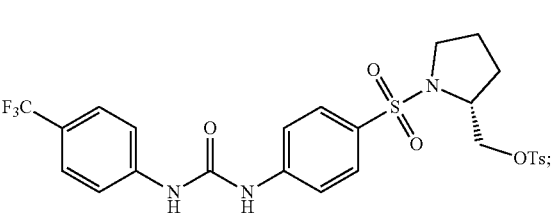

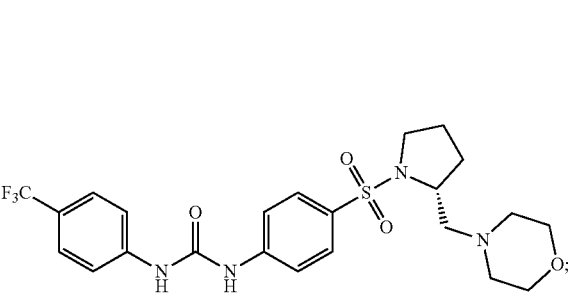

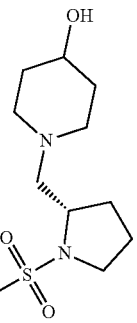

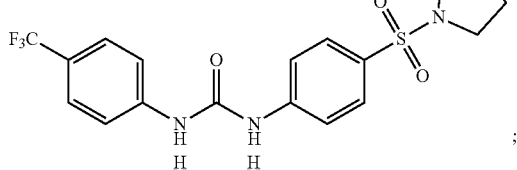

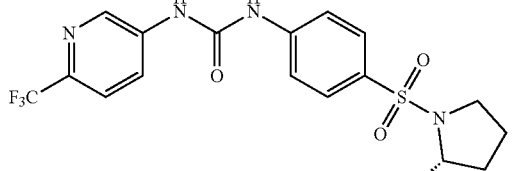

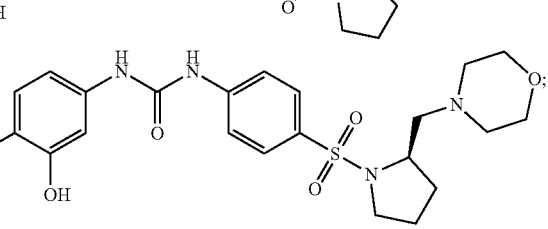

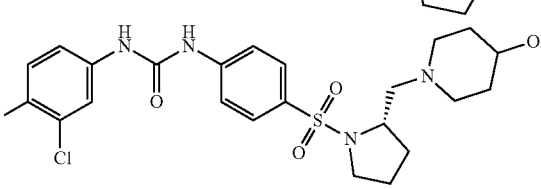

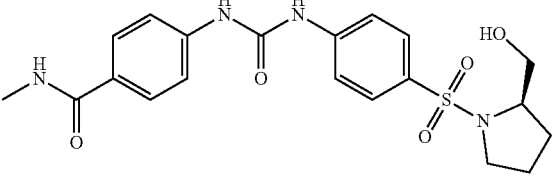

-continued

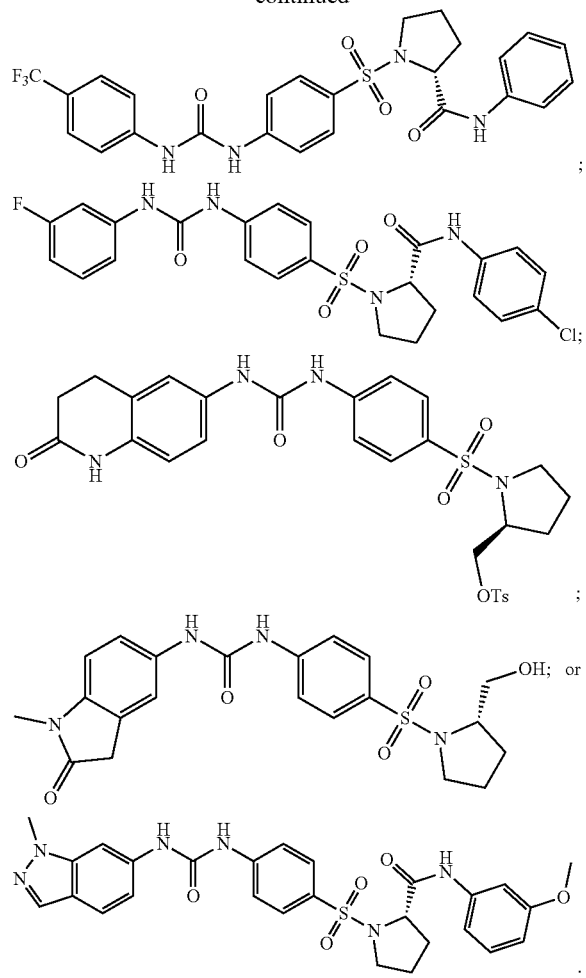

Further embodiments are directed to compounds of Formula II where $L_2$ is —CH$_2$— and X is C, as shown in Formula IIa.

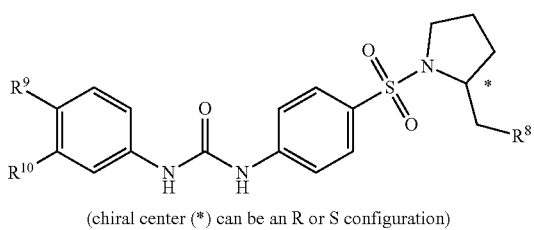

Formula IIa (chiral center (*) can be an R or S configuration)

Certain aspects are directed to a compound of Formula IIa wherein $R^8$ is a substituted or unsubstituted: morphiline, piperidine, or phenyl. In a further aspect $R^8$ is —OH or —OTs.

Certain embodiments are directed to a compound of Formula II where $R^9$ is —CF$_3$ and $R^{10}$ is H, as shown in Formula IIb. In certain aspects $R^8$ is —OH, —OTs, alkoxy, ester, primary amine, secondary amine, substituted or unsubstituted aryl, or substituted or unsubstituted 3-7 member heterocycle.

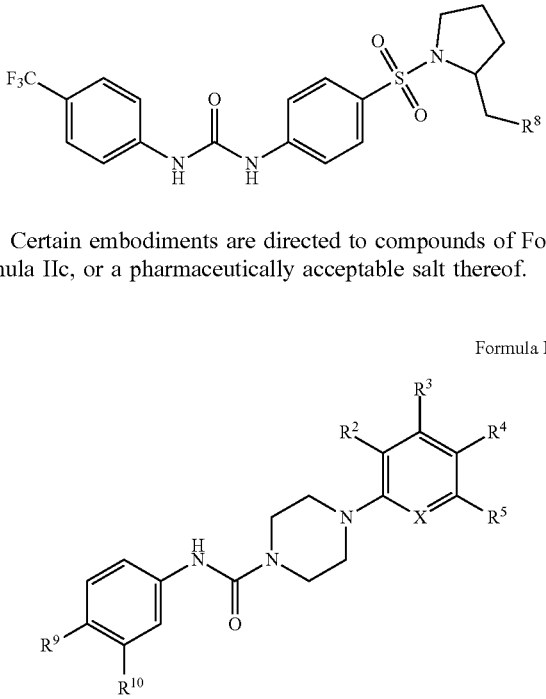

Formula IIb

Certain embodiments are directed to compounds of Formula IIc, or a pharmaceutically acceptable salt thereof.

Formula IIc where $R^2$, $R^3$, and $R^5$ are independently H, —OH, alkyl, alkoxy, halogen, —NH$_2$, or —CF$_3$; $R^4$ is —OH, —NH$_2$, —CF$_3$, —(CH$_2$)$_n$R$^6$ where n is 1-4 and $R^6$ is —OH or —NH$_2$, —O(CH$_2$)$_m$R$^7$ where m is 1-4 and $R^7$ is —OH or —NH$_2$; or $R^4$ and $R^5$ are optionally joined to form a 5-6 membered heteroaryl having 1-3 heteroatoms. $R^9$ and $R^{10}$ are independently selected from H, —OH, halogen, —CF$_3$, alkyl, hydroxylalkyl, amino, or alkylamino, or $R^9$ and $R^{10}$ are optionally joined to form a 5-6 membered heteroaryl or heterocycle having 1-3 heteroatoms and optionally substituted with one or more substituents selected from alkyl, acetyl, and carbonyl. In certain aspects the X substituent is at position 2, 3, 4, 5, or 6 of Formula IIc.

Other embodiments are directed to a compound of formula III, or a pharmaceutically acceptable salt thereof.

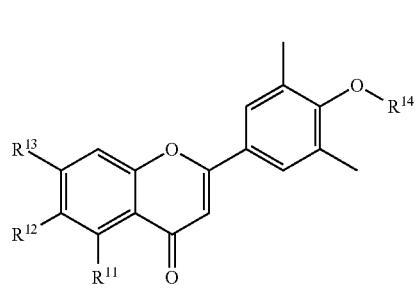

Formula III

Certain aspects are directed to a compound of Formula III where $R^{11}$, $R^{12}$, and $R^{13}$ are independently H, —OH, halogen, alkoxy, —NH$_2$, —CF$_3$, —(CO)R$^{17}$ where $R^{17}$ is alkyl, alkoxy, amino, or alkylamino; $R^{14}$ is substituted or unsubstituted alkyl or heteroalkyl, or substituted or unsubstituted aryl or heteroaryl. Certain aspects are directed to compounds of Formula III where R14 is a C1-4 alkyl substituted with one or more of: OH, alkoxy, amino, alkylamino, or an unsubstituted 5-6 membered heterocycle with 1-3 heteroatoms.

Certain aspects are directed a compound of Formula IIIa, or a pharmaceutically acceptable salt thereof.

Formula IIIa

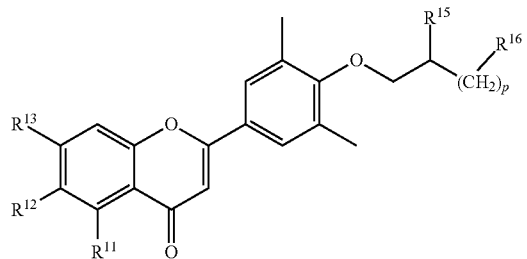

Certain aspects are directed to a compound of Formula IIIa where $R^{11}$, $R^{12}$, and $R^{13}$ are independently H, —OH, halogen, alkoxy, —$NH_2$, —$CF_3$, —(CO)$R^{17}$ where $R^{17}$ is alkyl, alkoxy, amino, or alkylamino; $R^{15}$ is H, —OH, alkyl, or $NH_2$; p is 0-4; $R^{16}$ is H, —OH, alkyl, alkoxy; or —$NR^{18}R^{19}$ where $R^{18}$ and $R^{19}$ are independently H, alkyl; or $R^{18}$ and $R^{19}$ are optionally joined to form a 3-6 membered substituted or unsubstituted heterocycle having 1-3 heteroatoms. In certain aspects $R^{15}$ is —OH. In a further aspect p is 0 or 1. In still a further aspect $R^{16}$ is —$NR^{18}R^{19}$. In certain aspects at least one of $R^{11}$, $R^{12}$, and $R^{13}$ of Formula IIIa is methoxy.

Certain aspects are directed a compound of Formula IIIb, or a pharmaceutically acceptable salt thereof. In this aspect, with reference to Formula IIIa, $R^{11}$ and $R^{13}$ are methoxy, $R^{12}$ is H, and $R^{15}$ is OH.

Formula IIIb

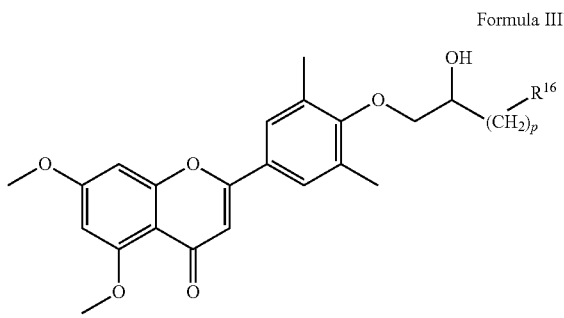

Certain aspects of Formula IIIb are direct to one or more compound having a structure of

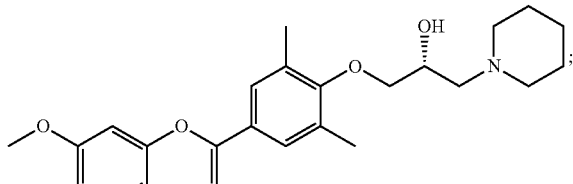

-continued

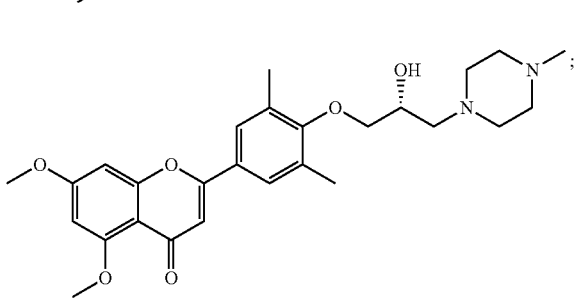

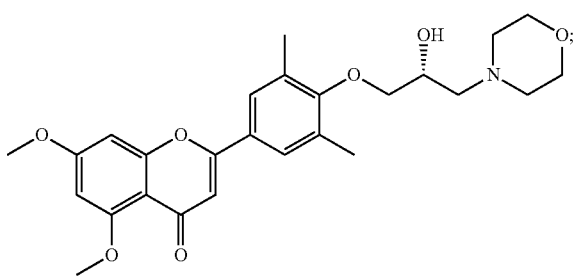

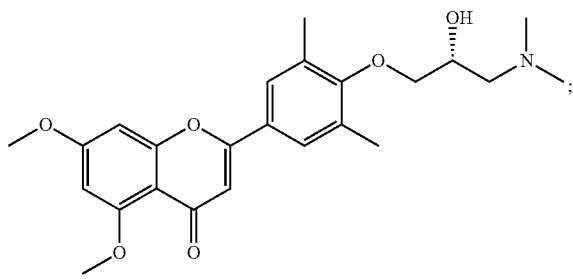

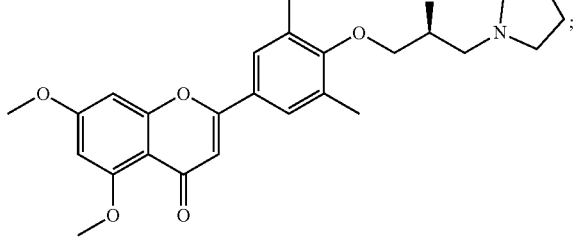

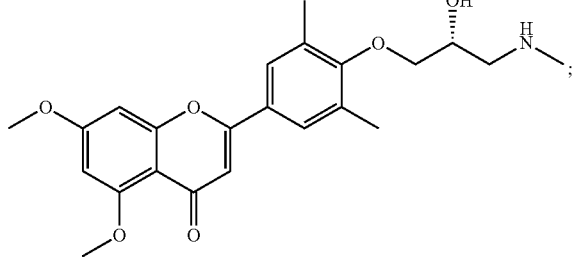

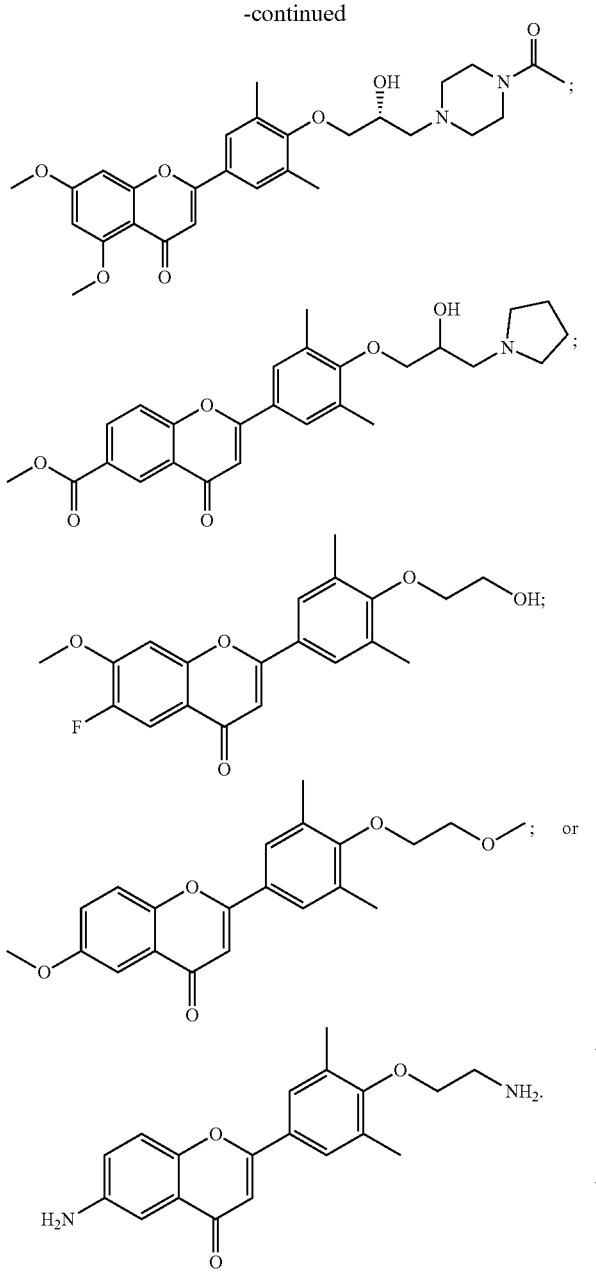

Certain embodiments are directed to a compound of Formula IVa, or a pharmaceutically acceptable salt thereof.

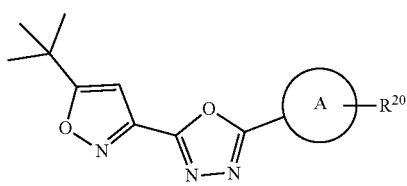

Formula IVa

Certain aspects are directed to Formula IVa where A is a 5-6 membered, mono- or bi-cyclic heteroaryl with 1-3 heteroatoms, and A is unsubstituted or substituted with one or more substituents $R^{20}$ and $R^{20}$ is —OH, halogen, $CF_3$, $NH_2$, alkyl, heteroalkyl, alkoxy, or acetyl. Certain aspects are directed to a compound of Formula IVa having the structure

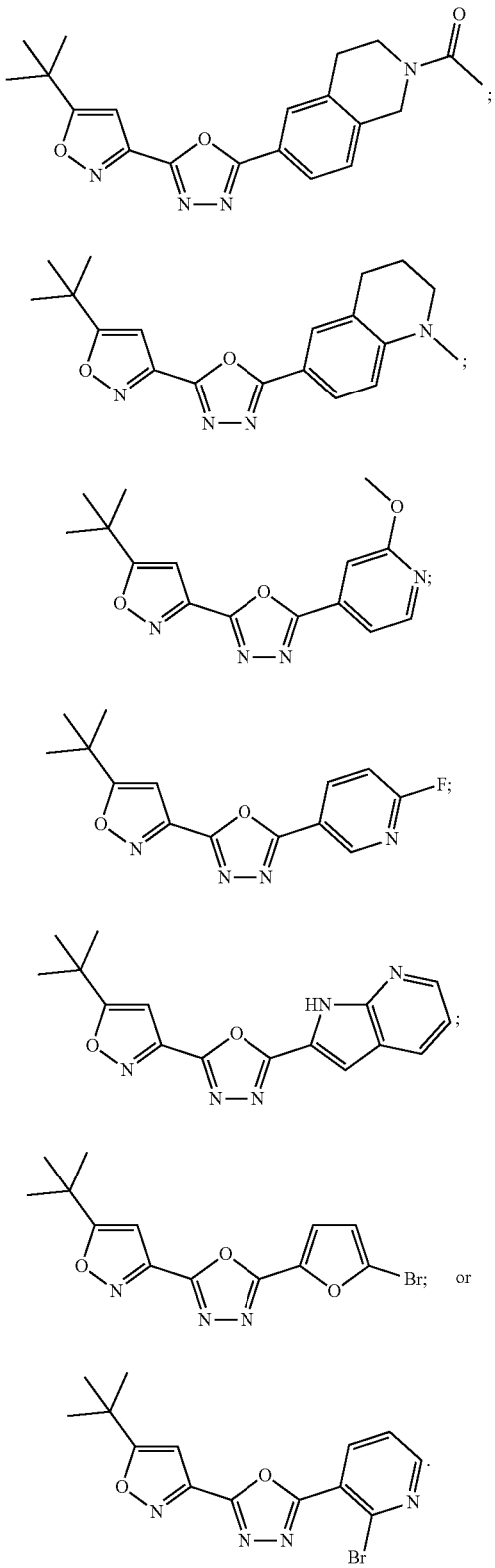

Further embodiments are directed to compounds of Formula IVb, or a pharmaceutically acceptable salt thereof.

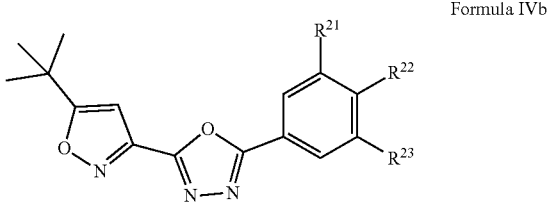

Formula IVb

Certain aspects are directed to compounds of Formula IVb where $R^{21}$ and $R^{23}$ are independently selected from —OH, halogen, $CF_3$, $NH_2$, alkyl, heteroalkyl, alkoxy, and acetyl; and $R^{22}$ is H, —OH, halogen, $CF_3$, $NH_2$, alkyl, heteroalkyl, alkoxy, or acetyl. Certain aspects are directed to compounds of Formula IVb where the compound is

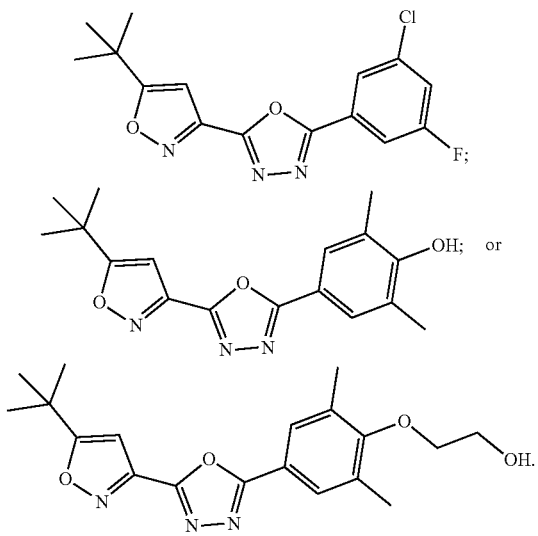

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The use of the word "a" or "an" when used in conjunction with the term "comprising" in the claims and/or the specification may mean "one," but it is also consistent with the meaning of "one or more," "at least one," and "one or more than one."

DESCRIPTION OF THE DRAWINGS

The following drawing forms part of the present specification and is included to further demonstrate certain aspects of the present invention. The invention may be better understood by reference to one or more of these drawings in combination with the detailed description of the specification embodiments presented herein.

FIGS. 5A-B ZL lead compounds block poly(I:C) induced airway inflammation. (5A) neutrophil counts in bronchoalveolar lavage fluid (BALF). (5B) IL-6 expression in BALF. Right panels are representative H&E staining from control, poly(I:C) or poly(I:C) with ZL0420 or ZL0454 treatment. Note the significant reduction in neutrophils and IL-6 in ZL treatments.

DESCRIPTION

Figure 1A:
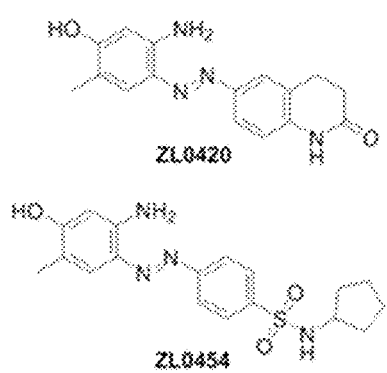
FIGS. 1A-D. (1A) Chemical structures of representative BRD4 inhibitors ZL0420 and ZL0454. (1B) Binding mode of ZL0420 with BRD4 BD1 in ribbon representation. The highlighted residues are Asn140 (N140), Tyr97 (Y97), Pro82 (P82), Trp81 (W81) and Lys91 (K91). (1C) Binding mode of ZL0454 with BRD4 BD1 in ribbon representation. (1D) Superimposition of ZL0420 and ZL0454 docked into BRD4 BD1 in the form of surface representation. WPF (Trp81-Pro82-Phe83) shelf is highlighted. Asn, Asparagine; Tyr, Tyrosine; Pro, Proline; Trp, Tryptophan; Lys, Lysine.

Chronic obstructive lung diseases (OLDs), including chronic obstructive pulmonary disease (COPD), asthma, cystic fibrosis (CF) and bronchiectasis, are highly prevalent conditions characterized by acute episodic decompensations and an inexorable decline in pulmonary function. The two most highly prevalent diseases are COPD and asthma; COPD affects 13.5 million (M) people in the US with a regional age-standardized death rate as high as 50 per 100,000, and asthma affects 25.7 M people, with a disproportionate impact in the pediatric population. Accumulating evidence suggests that TGFβ-induced remodeling plays an important role in the pathogenesis and severity of OLDs (Holgate et al., *Proc. Am. Thorac. Soc.* 2004, 1:93-8; Sagara et al., *J. Allergy Clin. Immunol.* 2002, 110:249-54). Studies conducted by the inventors have revealed that BRD4 is a key epigenetic regulator of TGFβ induced remodeling. As described below, the inventors have found that inhibition of BRD4 helps restore barrier function, reversing innate immunity and reducing airway remodeling.

Certain embodiments are directed to compounds that selectively target BRD4 and inhibit BRD4 in airway remodeling and defective innate immune response in asthma and chronic obstructive lung diseases. Several series of novel BRD4 inhibitors have been designed and created using computer-assisted rational structure/fragment-based drug design. Some of these compounds have been tested in vitro (cellular activity in primary airway epithelial cells (hSAECs) and target specificity) and in vivo (pharmacokinetics, distribution and efficacy). A number of advanced lead molecules have been identified as superior drug candidates for preclinical and clinical trials. These molecules may be developed as preventive and therapeutic agents for various diseases including but not limited to inflammatory diseases (e.g. chronic obstructive lung diseases, ulcerative colitis, and liver fibrosis), burn injury management by mediating hypertrophic scar formation, cancers (e.g., NMC, breast cancer, colon cancer, and lymphoma), atherosclerosis, diabetes, obesity, CNS disorders, and infectious diseases (e.g., HIV).

Studies described herein evaluated the NFκB-BRD4 signaling pathway in airway epithelial cells that mediates the acute inflammatory response to viral patterns. RelA deletion in cultured bronchiolar cells block viral-induced expression of inflammatory and anti-viral genes. RelA was deleted in bronchiolar cells using a tamoxifen-inducible Cre recombinase expressed by the Sgpc1a/CC10 promoter crossed with a mouse containing homozygous RelA fl/fl. Deletion of bronchiolar RelA prevented bronchoalveolar cytokine expression of inflammatory cytokines and IFNs in response to either viral molecular patterns [poly(I:C)], or after exposure to live virus (RSV). Small molecule selective inhibitors of the BRD4 bromodomain (BD) were designed, synthesized, and demonstrated to be specific for BRD4 BD with sub-micromolar affinity. In one set of experiments, BRD4 inhibition completely blocked poly(I:C) induced inflammatory gene programs in vitro and airway inflammation and neutrophil recruitment in vivo. In a second set of experiments, BRD4 inhibition blocks RSV induced inflammatory gene programs, airway inflammation and neutrophil recruitment in vivo. Together, these data indicate that the bronchiolar NFκB-BRD4 axis plays a role in acute neutrophilic response to virus infections.

The bromodomain protein BDR4 is a chromatin remodeling enzyme recognized as one of the most important regulators of immune responses (Filippakopoulos et al., *Nature*, 2010, 468(7327):1067-73; Xu and Vakoc, *Trends Cell Biol*, 2014, 24(11):615-16; Brown et al., *Mol Cell*, 2014, 56(2):219-31; Kanno et al., *Nat Struct Mol Biol*, 2014, 21(12):1047-57). The bromodomain and extraterminal domain (BET) family proteins (Wu and Chiang, *J Biol Chem*, 2007, 282(18):13141-45), including BRD2, BRD3, BRD4 and BRDT, contain two bromodomains (BDs) (Filippakopoulos et al., *Nature*, 2010, 468(7327):1067-1073). Among ubiquitously expressed BET family proteins, BRD4 is unique in that it interacts with P-TEFb through its C-terminal tail (Bisgrove et al., *PNAS USA*, 2007, 104(34):13690-95). Furthermore, BRD4 is a mammalian bromodomain protein that preferentially binds to acetylated histone H4 (H4-KAc) in living cells (Brasier et al., *J Virol*, 2011, 85(22):11752-69; Jang et al., *Mol Cell*, 2005, 19(4):523-34; Yang et al., *Nature*, 2001, 414(6861):317-22). Through H4-KAc binding, BRD4 is a critical mediator of transcriptional elongation, functioning to recruit activated CDK9 to the promoter (Jang et al., *Mol Cell*, 2005, 19(4):523-34; Yang et al., *Nature*, 2001, 414(6861):317-22).

Modulators of BRD4 include compounds of Formula I, or a pharmaceutically acceptable salt thereof.

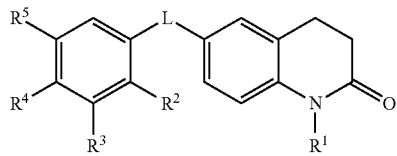

Formula I

Certain aspects of the invention are directed to compounds of Formula I where L is —N=N— or —NH(CO)NH—; $R^1$ is H or C1-4 alkyl or arylalkyl; $R^2$, $R^3$, and $R^5$ are independently H, —OH, alkyl, alkoxy, halogen, —NH$_2$, or —CF$_3$; $R^4$ is —OH, —NH$_2$, —CF$_3$, —(CH$_2$)$_n$R$^6$ where n is 1-4 and $R^6$ is —OH or —NH$_2$, —O(CH$_2$)$_m$R$^7$ where m is 1-4 and $R^7$ is —OH or —NH$_2$; or $R^4$ and $R^5$ are optionally joined to form a 5-6 membered heteroaryl having 1-3 heteroatoms.

Certain aspects are directed to compounds of Formula Ia where, with respect to Formula I, L is —N=N— and $R^1$ is H.

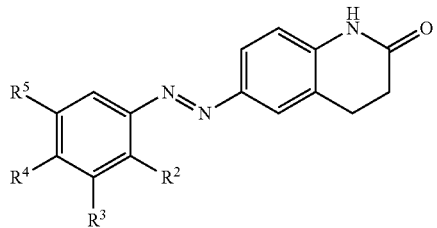

Formula Ia

Certain aspects are directed to a compound having the structure of ZL0420.

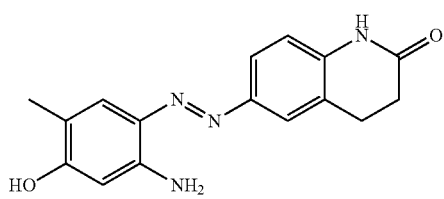

ZL0420

Still further aspects are directed to compound of Formula Ib, where, with respect to Formula I, L is —NH(CO)NH—. In certain aspects $R^1$ is H. In another aspect $R^4$ is —OH; —(CH$_3$)$_n$R$^6$ where n is 1-4 and $R^6$ is —OH; or —O(CH$_3$)$_m$R$^7$ where m is 1-4 and $R^7$ is —OH.

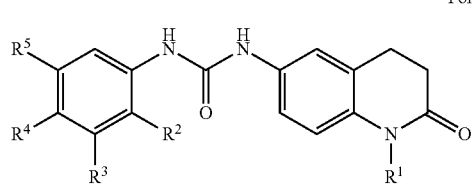

Formula Ib

Certain aspects of the invention are directed to compounds having a structure of

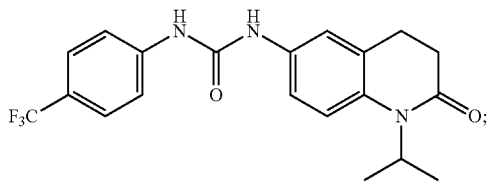

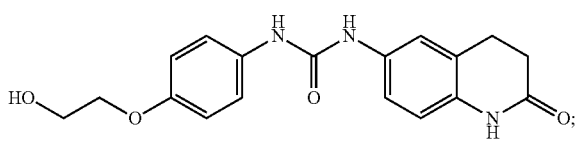

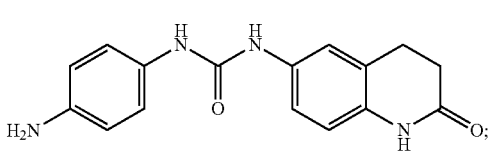

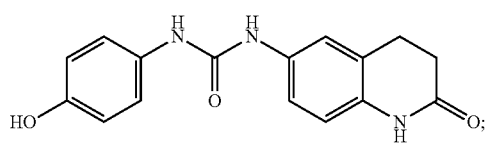

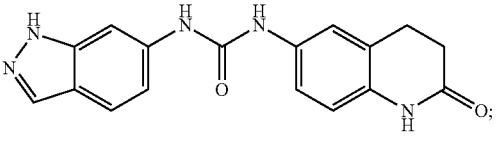

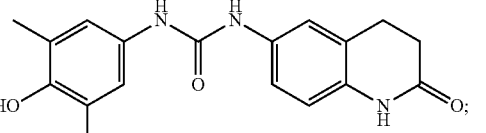

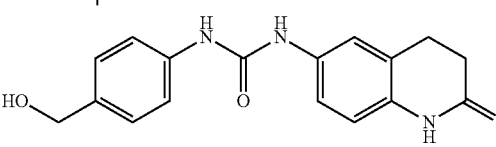

Certain embodiments are directed to compound ZL0454, or a pharmaceutically acceptable salt thereof.

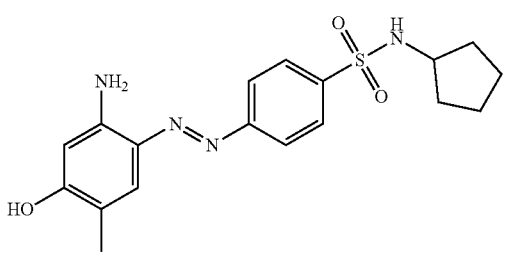

ZL0454

Certain embodiments are directed to compounds of Formula II, or a pharmaceutically acceptable salt thereof.

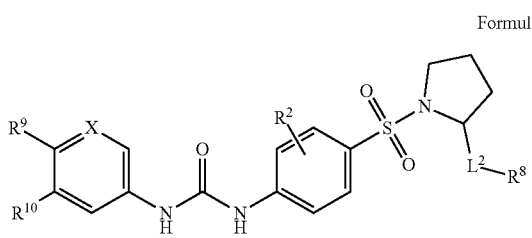

Formula II

Certain aspects are directed to compounds of Formula II wherein $L^2$ is —CH$_2$— or —(CO)NH—; $R^2$ is as described above; $R^8$ is —OH, —OTs, alkoxy, ester, substituted or unsubstituted aryl, or substituted or unsubstituted 3-7 member heterocycle, or —NR$^{18}$R$^{19}$ where R$^{18}$ and R$^{19}$ are independently H, alkyl; or R$^{18}$ and R$^{19}$ are optionally joined to form a 3-6 membered substituted or unsubstituted heterocycle having 1-3 heteroatoms; X is C or N; $R^9$ and $R^{10}$ are independently selected from H, —OH, halogen, —CF$_3$, alkyl, hydroxylalkyl, amino, or alkylamino, or $R^9$ and $R^{10}$ are optionally joined to form a 5-6 membered heteroaryl or heterocycle having 1-3 heteroatoms and optionally substituted with one or more substituents selected from alkyl, acetyl, and carbonyl. In certain aspects the X substituent is at position 2, 3, 4, 5, or 6 of Formula II. In a further aspect X is C. In particular aspects a compound of Formula II is

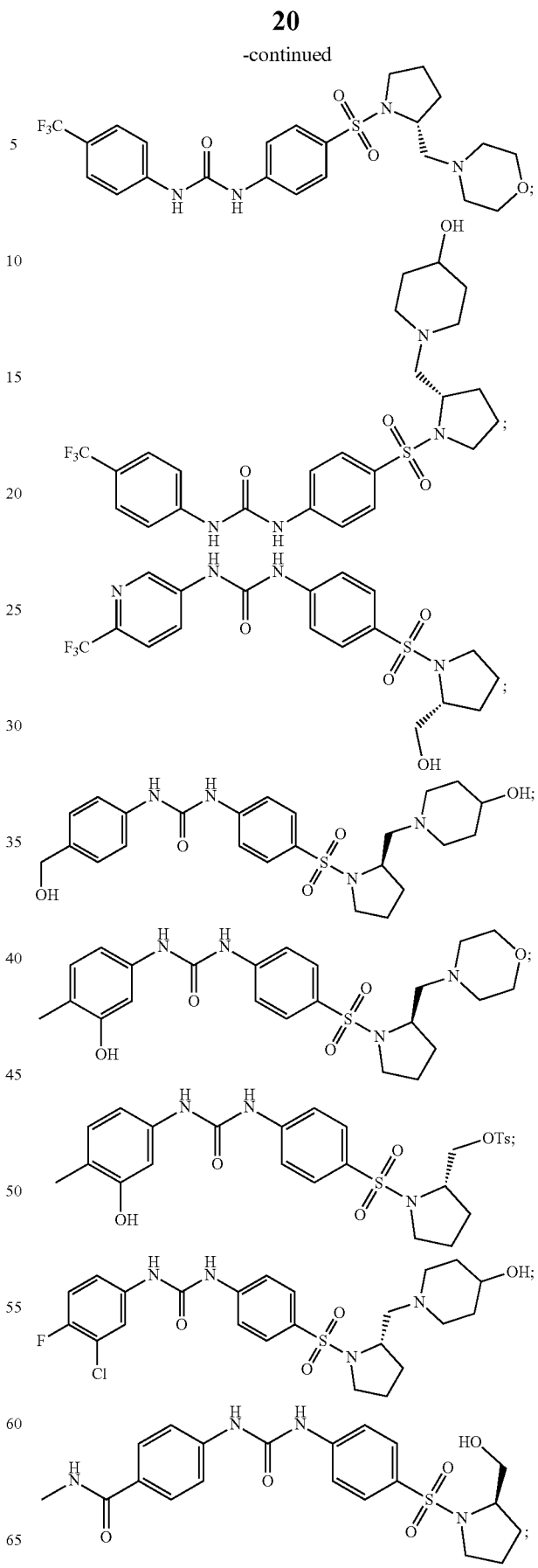

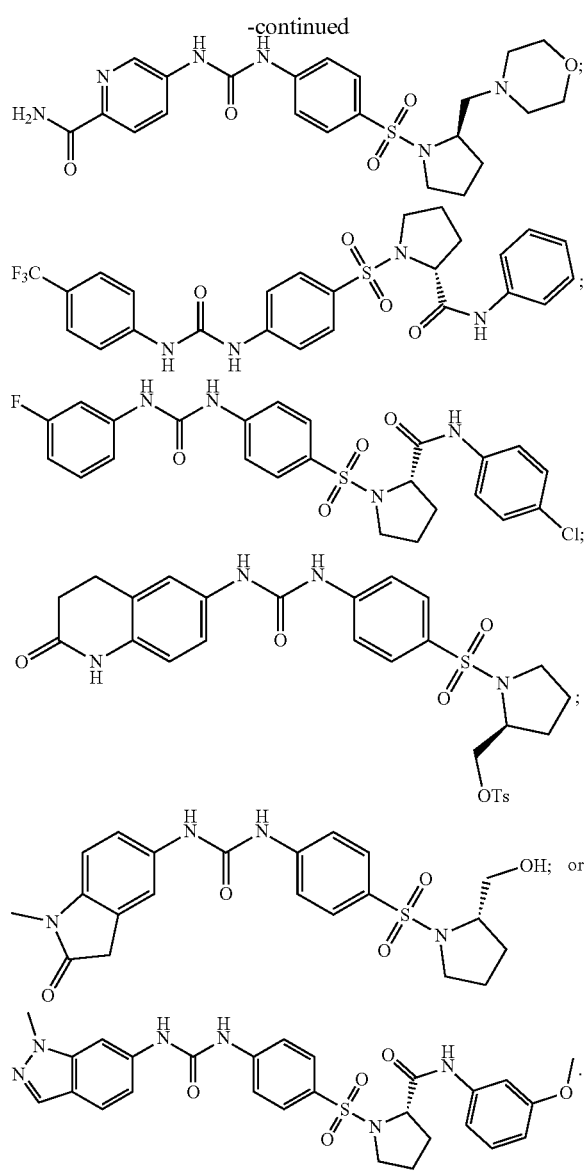

Further embodiments are directed to compounds of Formula II where $L_2$ is —CH$_2$— and X is C, as shown in Formula IIa.

Formula IIa

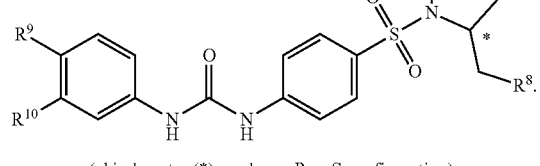

(chiral center (*) can be an R or S configuration)

Certain aspects are directed to a compound of Formula IIa wherein $R^8$ is a substituted or unsubstituted: morpholine, piperidine, or phenyl. In a further aspect $R^8$ is —OH or —OTs.

Certain embodiments are directed to a compound of Formula II where $R^9$ is —CF$_3$ and $R^{10}$ is H, as shown in Formula IIb. In certain aspects $R^8$ is —OH, —OTs, alkoxy, ester, primary amine, secondary amine, substituted or unsubstituted aryl, or substituted or unsubstituted 3-7 member heterocycle.

Formula IIb

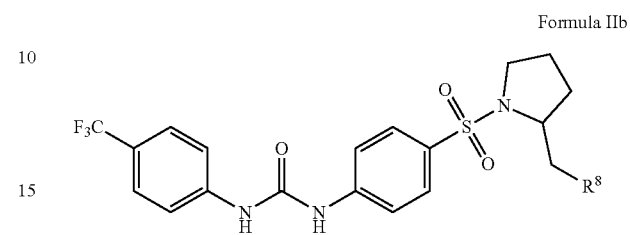

Certain embodiments are directed to compounds of Formula III, or a pharmaceutically acceptable salt thereof.
Certain embodiments are directed to compounds of Formula IIc, or a pharmaceutically acceptable salt thereof.

Formula IIc

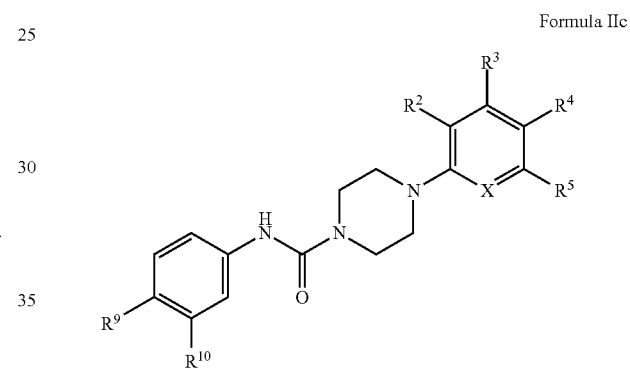

$R^2$, $R^3$, and $R^5$ are independently H, —OH, alkyl, alkoxy, halogen, —NH$_2$, or —CF$_3$; $R^4$ is —OH, —NH$_2$, —CF$_3$, —(CH$_2$)$_n$R$^6$ where n is 1-4 and $R^6$ is —OH or —NH$_2$, —O(CH$_2$)$_m$R$^7$ where m is 1-4 and $R^7$ is —OH or —NH$_2$; or $R^4$ and $R^5$ are optionally joined to form a 5-6 membered heteroaryl having 1-3 heteroatoms. $R^9$ and $R^{10}$ are independently selected from H, —OH, halogen, —CF$_3$, alkyl, hydroxylalkyl, amino, or alkylamino, or $R^9$ and $R^{10}$ are optionally joined to form a 5-6 membered heteroaryl or heterocycle having 1-3 heteroatoms and optionally substituted with one or more substituents selected from alkyl, acetyl, and carbonyl. In certain aspects the X substituent is at position 2, 3, 4, 5, or 6 of Formula IIc.

Certain embodiments are directed to compounds of Formula III, or a pharmaceutically acceptable salt thereof.

Formula III

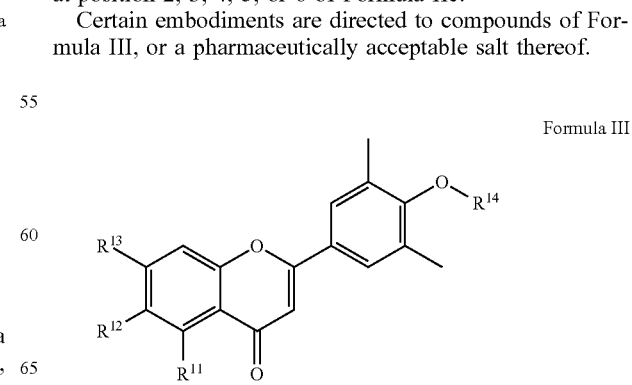

Certain aspects are directed to a compound of Formula III where $R^{11}$, $R^{12}$, and $R^{13}$ are independently H, —OH, halogen, alkoxy, —NH$_2$, —CF$_3$, —(CO)R$^{17}$ where $R^{17}$ is alkyl, alkoxy, amino, or alkylamino; $R^{14}$ is substituted or unsubstituted alkyl or heteroalkyl, or substituted or unsubstituted aryl or heteroaryl. Certain aspects are directed to compounds of Formula III where $R^{14}$ is a C1-4 alkyl substituted with one or more of: OH, alkoxy, amino, alkylamino, or an unsubstituted 5-6 membered heterocycle with 1-3 heteroatoms.

Certain aspects are directed a compound of Formula IIIa, or a pharmaceutically acceptable salt thereof.

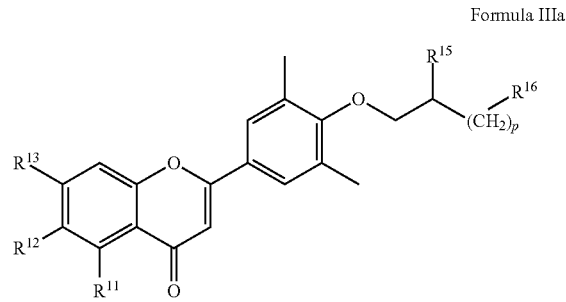

Formula IIIa

Certain aspects are directed to a compound of Formula IIIa where $R^{11}$, $R^{12}$, and $R^{13}$ are independently H, —OH, halogen, alkoxy, —NH$_2$, —CF$_3$, —(CO)R$^{17}$ where $R^{17}$ is alkyl, alkoxy, amino, or alkylamino; $R^{15}$ is H, —OH, alkyl, or NH$_2$; p is 0-4; $R^{16}$ is H, —OH, alkyl, alkoxy; or —NR$^{18}$R$^{19}$ where $R^{18}$ and $R^{19}$ are independently H, alkyl; or $R^{18}$ and $R^{19}$ are optionally joined to form a 3-6 membered substituted or unsubstituted heterocycle having 1-3 heteroatoms. In certain aspects $R^{15}$ is —OH. In a further aspect p is 0 or 1. In still a further aspect $R^{16}$ is —NR$^{18}$R$^{19}$. In certain aspects at least one of $R^{11}$, $R^{12}$, and $R^{13}$ of Formula IIIa is methoxy.

Certain aspects are directed a compound of Formula IIIb, or a pharmaceutically acceptable salt thereof. In this aspect, with reference to Formula IIIa, $R^{11}$ and $R^{13}$ are methoxy, $R^2$ is H, and $R^{15}$ is OH.

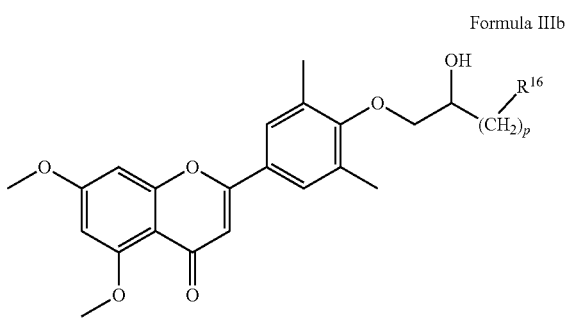

Formula IIIb

Certain aspects of Formula IIIb are direct to one or more compound having a structure of

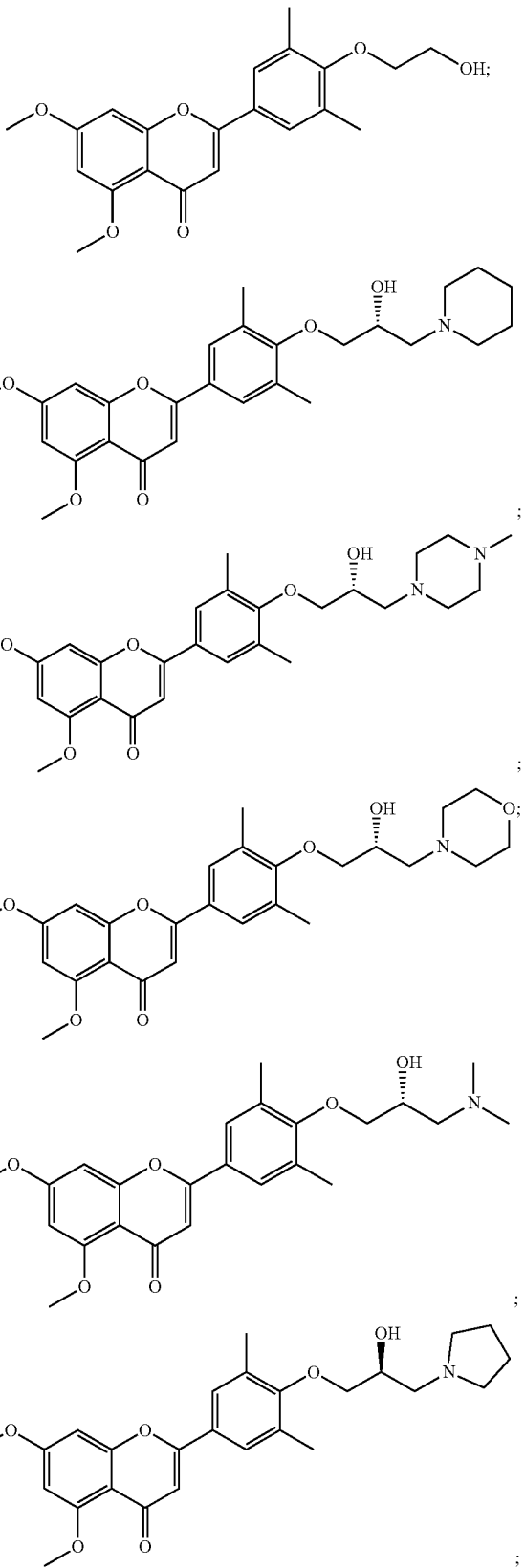

-continued

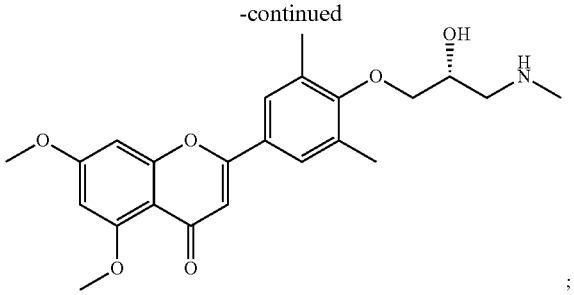
;

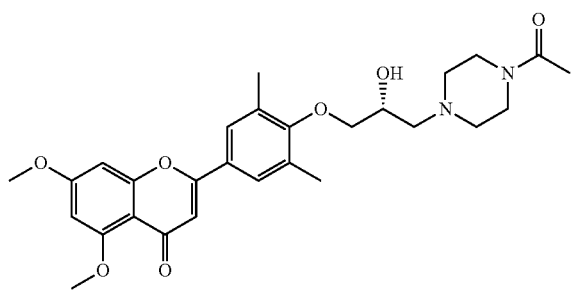
;

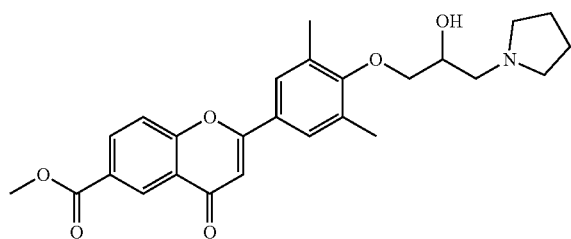
;

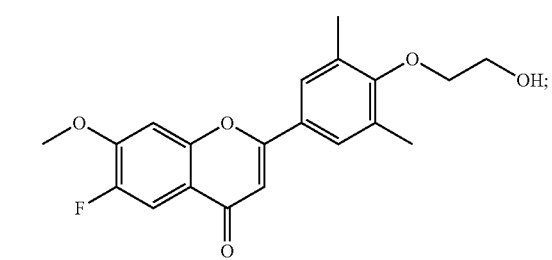
;

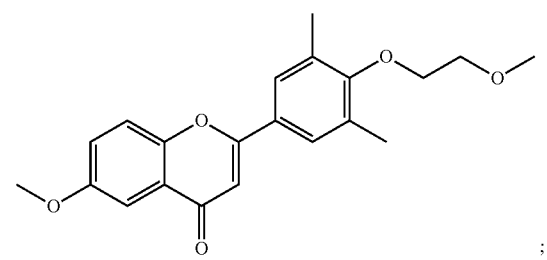
; or

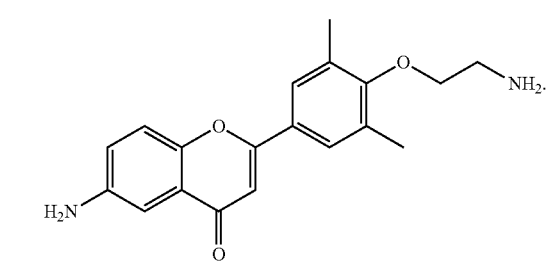
.

Certain embodiments are directed to a compound of Formula IVa, or a pharmaceutically acceptable salt thereof.

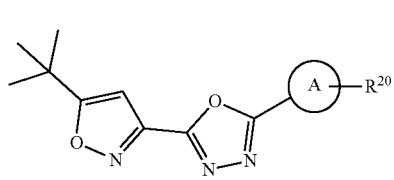

Formula IVa

Certain aspects are directed to Formula IVa where A is a 5-6 membered, mono- or bi-cyclic heteroaryl with 1-3 heteroatoms, and A is unsubstituted or substituted with one or more substituents $R^{20}$ and $R^{20}$ is —OH, halogen, $CF_3$, $NH_2$, alkyl, heteroalkyl, alkoxy, or acetyl. Certain aspects are directed to a compound of Formula IVa having the structure

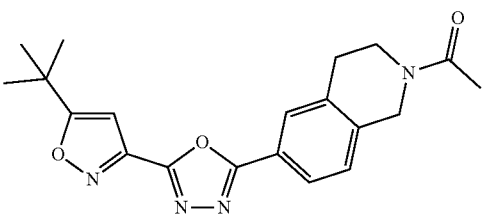
;

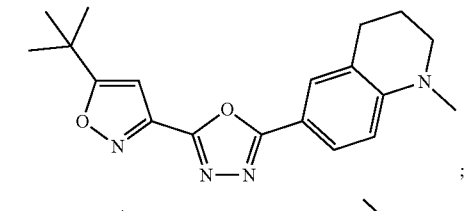
;

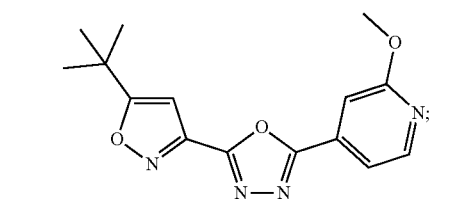
;

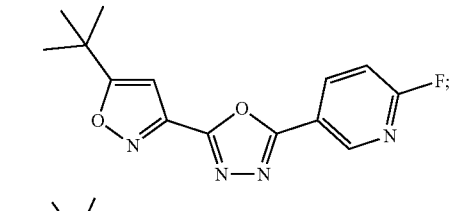
;

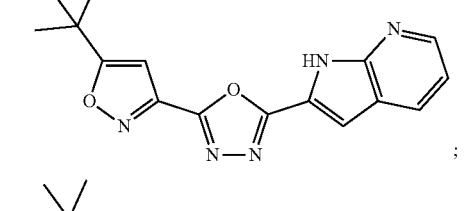
;

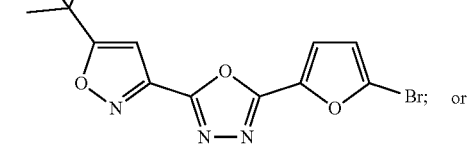
; or

-continued

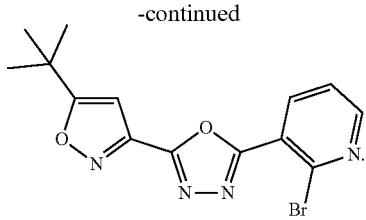

Further embodiments are directed to compounds of Formula IVb, or a pharmaceutically acceptable salt thereof.

Formula IVb

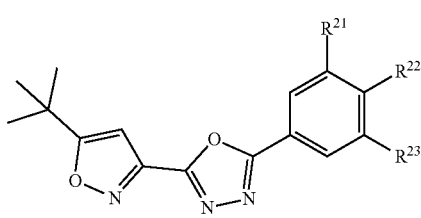

Certain aspects are directed to compounds of Formula IVb where R²¹ and R²³ are independently selected from —OH, halogen, CF₃, NH₂, alkyl, heteroalkyl, alkoxy, and acetyl;

and R²² is H, —OH, halogen, CF₃, NH₂, alkyl, heteroalkyl, alkoxy, or acetyl. Certain aspects are directed to compounds of Formula IVb where the compound is

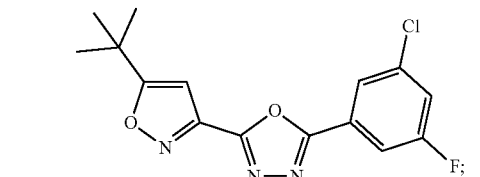

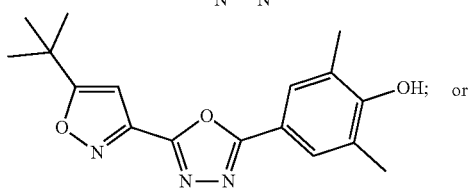
or

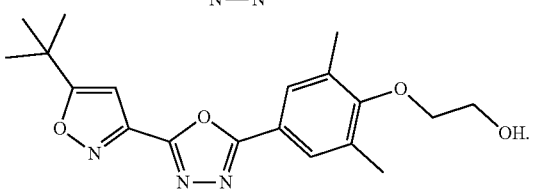
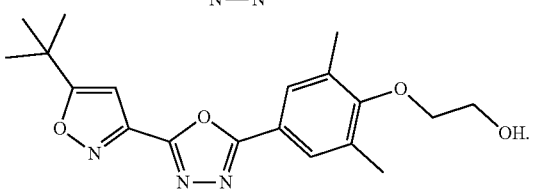

TABLE 1

List of representative compounds that have been synthesized and pharmacologically screened. Inhibitory effects of BRD4 inhibitors on induction of fibrotic genes including CIG5 and IL-6 in hSAECs.

| Compounds | Structure | CIG5 (%) | IL-6 (%) |
|---|---|---|---|
| ZL0420 | 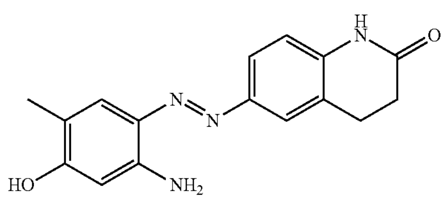 [SMILES: Cc1cc(/N=N/c2ccc3c(c2)CCC(=O)N3)c(N)cc1O] | 1.54 | 0.54 |
| ZL0454 | 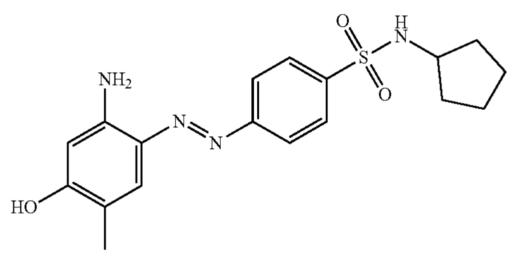 [SMILES: Cc1cc(/N=N/c2ccc(S(=O)(=O)NC3CCCC3)cc2)c(N)cc1O] | 15.6 | 0.9 |
| ZL0556 | 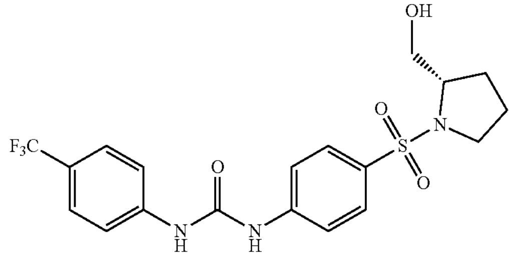 [SMILES: O=C(Nc1ccc(C(F)(F)F)cc1)Nc1ccc(S(=O)(=O)N2CCC[C@H]2CO)cc1] | 0.89 | 0.85 |

TABLE 1-continued

List of representative compounds that have been synthesized and pharmacologically screened. Inhibitory effects of BRD4 inhibitors on induction of fibrotic genes including CIG5 and IL-6 in hSAECs.

| Compounds | Structure | CIG5 (%) | IL-6 (%) |
|---|---|---|---|
| ZL0586 | 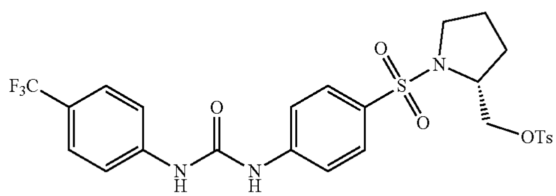 [SMILES: Cc1ccc(S(=O)(=O)OC[C@H]2CCCN2S(=O)(=O)c2ccc(NC(=O)Nc3ccc(C(F)(F)F)cc3)cc2)cc1] | 1.4 | 3.4 |
| ZL0590 | 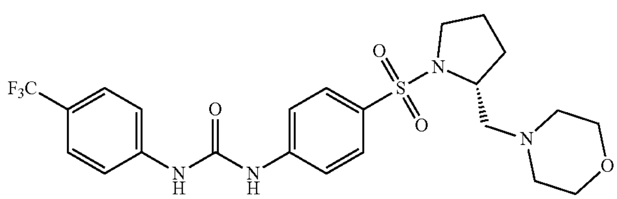 [SMILES: O=C(Nc1ccc(C(F)(F)F)cc1)Nc1ccc(S(=O)(=O)N2CCC[C@@H]2CN2CCOCC2)cc1] | 0.78 | 0.26 |
| ZL0591 | 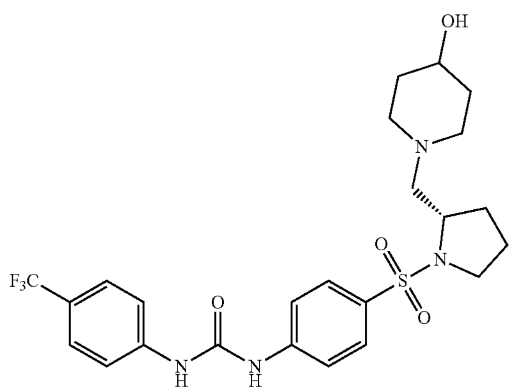 [SMILES: O=C(Nc1ccc(C(F)(F)F)cc1)Nc1ccc(S(=O)(=O)N2CCC[C@H]2CN2CCC(O)CC2)cc1] | 0.48 | 0.28 |
| ZL0589 | 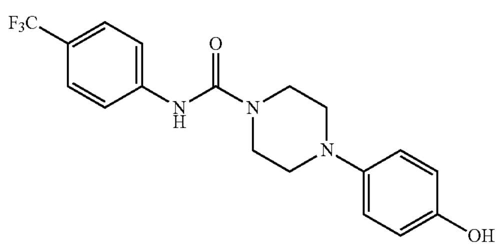 [SMILES: O=C(Nc1ccc(C(F)(F)F)cc1)N1CCN(c2ccc(O)cc2)CC1] | 5.6 | 4.2 |
| ZL0468 | 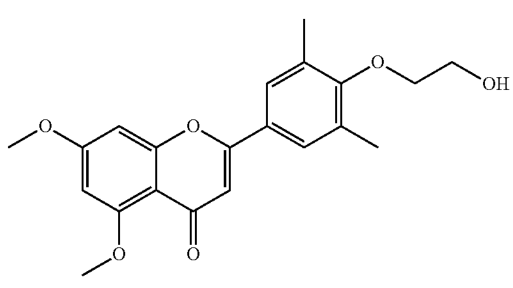 [SMILES: COc1cc(OC)c2c(=O)cc(-c3cc(C)c(OCCO)c(C)c3)oc2c1] | 3.14 | 2.25 |

TABLE 1-continued

List of representative compounds that have been synthesized and pharmacologically screened. Inhibitory effects of BRD4 inhibitors on induction of fibrotic genes including CIG5 and IL-6 in hSAECs.

| Compounds | Structure | CIG5 (%) | IL-6 (%) |
|---|---|---|---|
| ZL0513 | 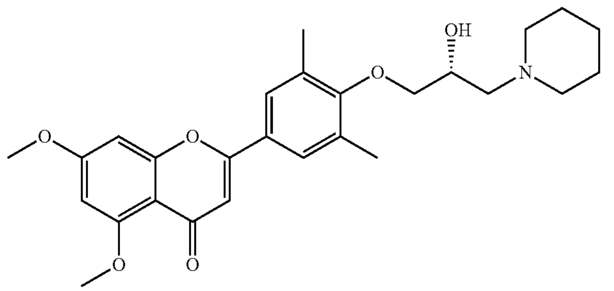 [SMILES: COc1cc(OC)c2c(=O)cc(-c3cc(C)c(OC[C@H](O)CN4CCCCC4)c(C)c3)oc2c1] | 0.81 | 0.3 |
| ZL0516 | 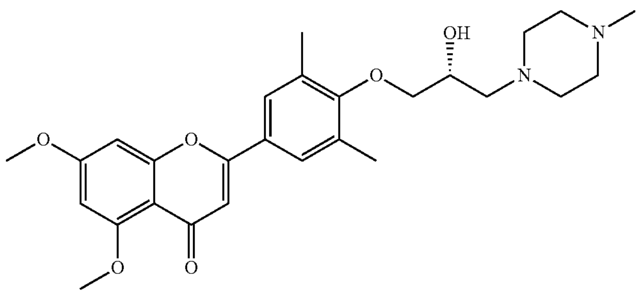 | 9.1 | 2.71 |
| ZL0165 | 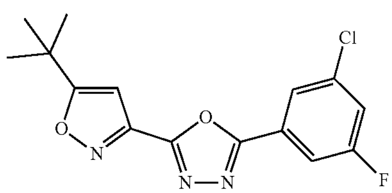 [SMILES: CC(C)(C)c1cc(-c2nnc(-c3cc(F)cc(Cl)c3)o2)no1] | 1.01 | 2.5 |

TABLE 2

Binding affinities of selected compounds with BRD4 BD1, BRD4 BD2, BRD2 BD1 and BRD2 BD2.

| Compounds | CIG5 (IC$_{50}$, µM) | IL-6 (IC$_{50}$, µM) | BRD4 (IC$_{50}$, µM) | | BRD2 (IC$_{50}$, µM) | |
|---|---|---|---|---|---|---|
| | | | BD1 | BD2 | BD1 | BD2 |
| JQ1 | 0.95 | 1.02 | 0.092 | 0.062 | 0.078 | 0.052 |
| RVX-208 | 1.66 | 3.29 | 1.142 | 0.135 | 5.78 | 0.251 |
| ZL0392 | 1.34 | 1.88 | 0.103 | 0.142 | | |
| ZL0420 | 0.42 | 0.45 | 0.027 | 0.032 | 0.803 | 1.736 |
| ZL0454 | 0.6 | 0.69 | 0.049 | 0.032 | 0.772 | 1.836 |
| HJC05100 | 3.5 | 3.2 | 0.183 | 0.147 | | |
| ZL0468 | 2.6 | 2.8 | 0.164 | 0.135 | | |

Certain embodiments are directed to one or more of the compounds of Table 3.

TABLE 3

The structures of selected molecules.

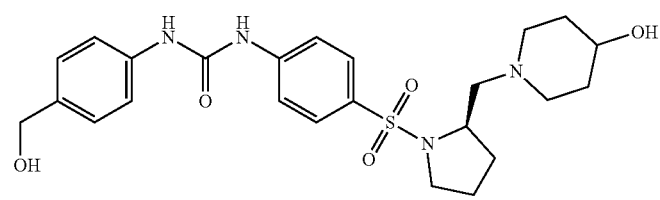 [SMILES: O=C(Nc1ccc(CO)cc1)Nc1ccc(S(=O)(=O)N2CCC[C@@H]2CN2CCC(O)CC2)cc1]

TABLE 3-continued
The structures of selected molecules.
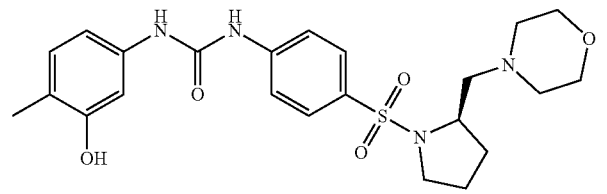 [SMILES: Cc1ccc(NC(=O)Nc2ccc(S(=O)(=O)N3CCC[C@@H]3CN3CCOCC3)cc2)cc1O]
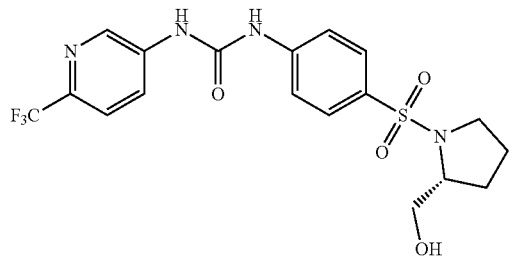 [SMILES: O=C(Nc1ccc(S(=O)(=O)N2CCC[C@@H]2CO)cc1)Nc1ccc(C(F)(F)F)nc1]
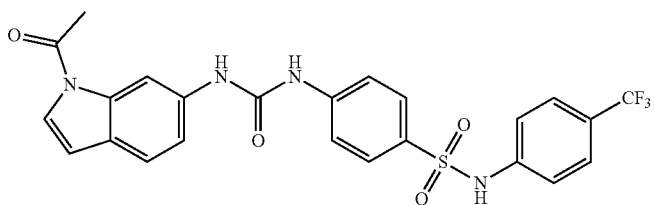 [SMILES: CC(=O)n1ccc2ccc(NC(=O)Nc3ccc(S(=O)(=O)Nc4ccc(C(F)(F)F)cc4)cc3)cc21]
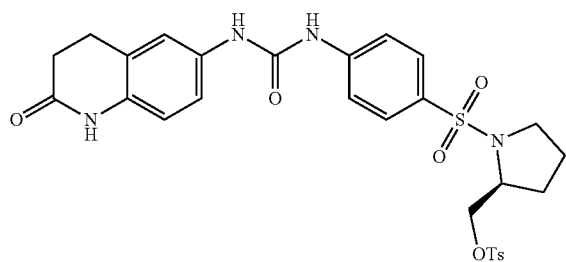 [SMILES: Cc1ccc(S(=O)(=O)OC[C@@H]2CCCN2S(=O)(=O)c2ccc(NC(=O)Nc3ccc4c(c3)CCC(=O)N4)cc2)cc1]
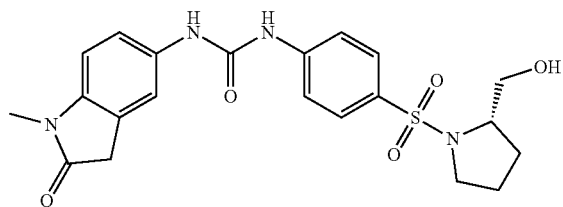 [SMILES: CN1C(=O)Cc2cc(NC(=O)Nc3ccc(S(=O)(=O)N4CCC[C@H]4CO)cc3)ccc21]
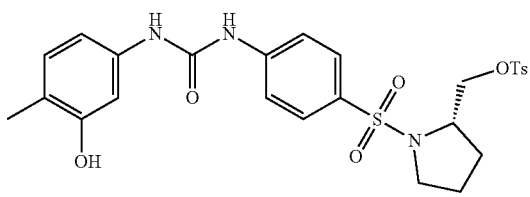 [SMILES: Cc1ccc(S(=O)(=O)OC[C@@H]2CCCN2S(=O)(=O)c2ccc(NC(=O)Nc3ccc(C)c(O)c3)cc2)cc1]
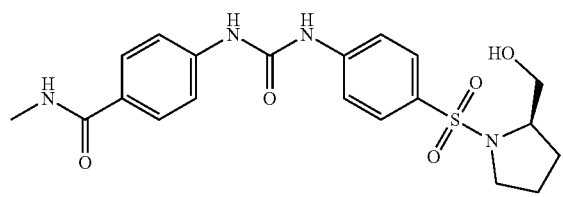 [SMILES: CNC(=O)c1ccc(NC(=O)Nc2ccc(S(=O)(=O)N3CCC[C@@H]3CO)cc2)cc1]

TABLE 3-continued
The structures of selected molecules.
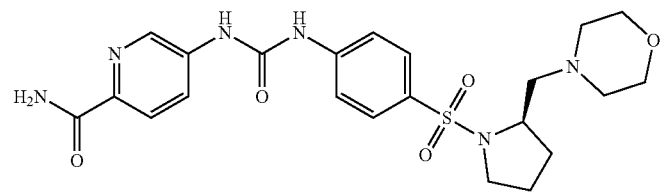 [SMILES: NC(=O)c1ccc(NC(=O)Nc2ccc(S(=O)(=O)N3CCC[C@@H]3CN3CCOCC3)cc2)cn1]
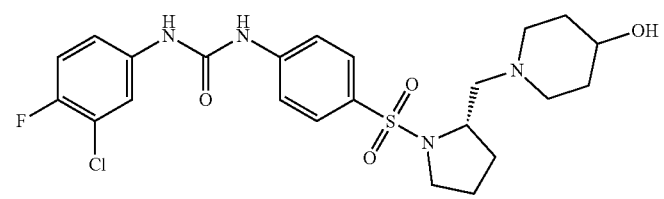 [SMILES: O=C(Nc1ccc(S(=O)(=O)N2CCC[C@H]2CN2CCC(O)CC2)cc1)Nc1ccc(F)c(Cl)c1]
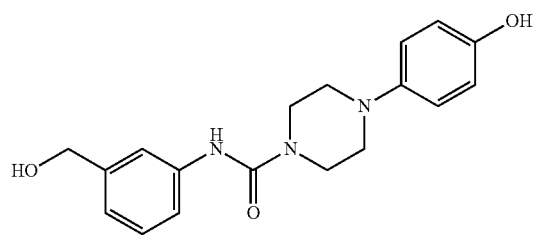 [SMILES: O=C(Nc1cccc(CO)c1)N1CCN(c2ccc(O)cc2)CC1]
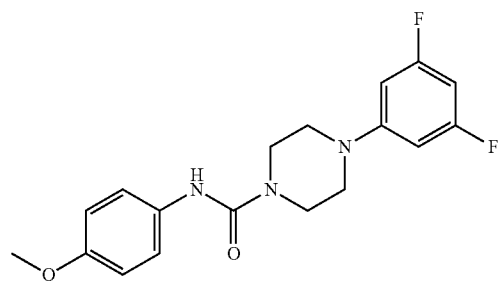 [SMILES: COc1ccc(NC(=O)N2CCN(c3cc(F)cc(F)c3)CC2)cc1]
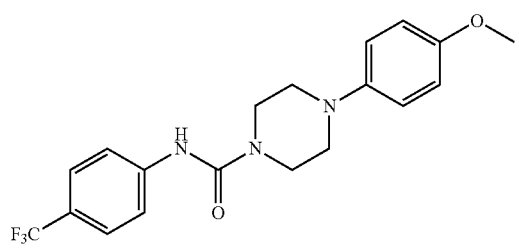 [SMILES: COc1ccc(N2CCN(C(=O)Nc3ccc(C(F)(F)F)cc3)CC2)cc1]
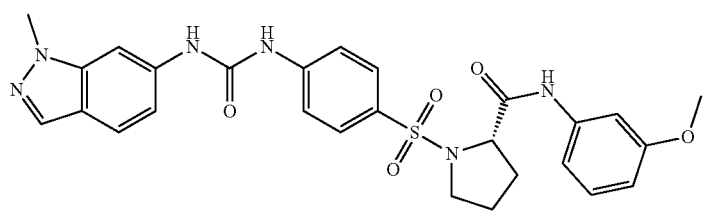 [SMILES: COc1cccc(NC(=O)[C@@H]2CCCN2S(=O)(=O)c2ccc(NC(=O)Nc3ccc4cnn(C)c4c3)cc2)c1]
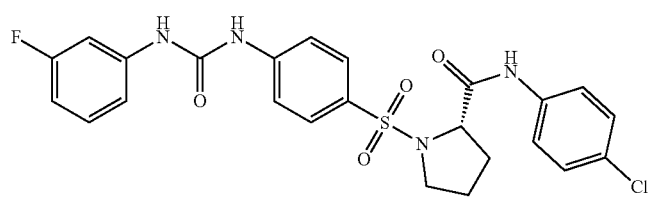 [SMILES: O=C(Nc1ccc(S(=O)(=O)N2CCC[C@H]2C(=O)Nc2ccc(Cl)cc2)cc1)Nc1cccc(F)c1]

TABLE 3-continued
The structures of selected molecules.
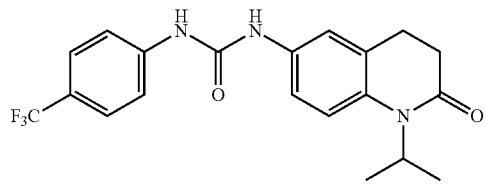 [SMILES: CC(C)N1C(=O)CCc2cc(NC(=O)Nc3ccc(C(F)(F)F)cc3)ccc21]
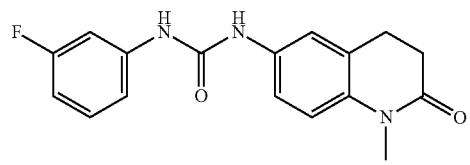 [SMILES: CN1C(=O)CCc2cc(NC(=O)Nc3cccc(F)c3)ccc21]
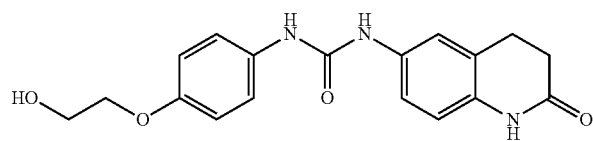 [SMILES: O=C1CCc2cc(NC(=O)Nc3ccc(OCCO)cc3)ccc2N1]
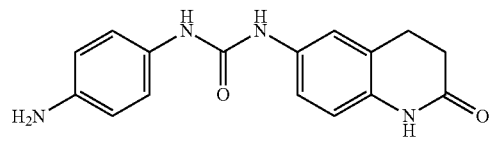 [SMILES: Nc1ccc(NC(=O)Nc2ccc3c(c2)CCC(=O)N3)cc1]
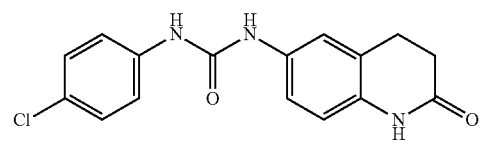 [SMILES: O=C1CCc2cc(NC(=O)Nc3ccc(Cl)cc3)ccc2N1]
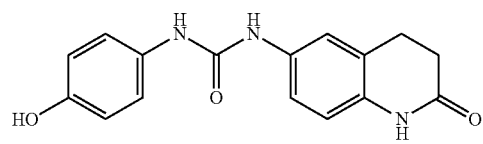 [SMILES: O=C1CCc2cc(NC(=O)Nc3ccc(O)cc3)ccc2N1]
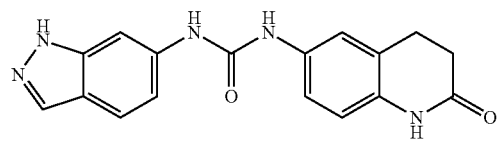 [SMILES: O=C1CCc2cc(NC(=O)Nc3ccc4cn[nH]c4c3)ccc2N1]
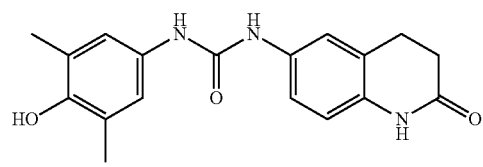 [SMILES: Cc1cc(NC(=O)Nc2ccc3c(c2)CCC(=O)N3)cc(C)c1O]
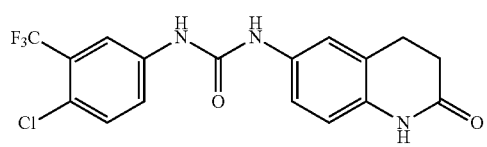 [SMILES: O=C1CCc2cc(NC(=O)Nc3ccc(Cl)c(C(F)(F)F)c3)ccc2N1]
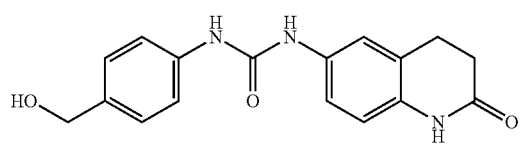 [SMILES: O=C1CCc2cc(NC(=O)Nc3ccc(CO)cc3)ccc2N1]

TABLE 3-continued
The structures of selected molecules.
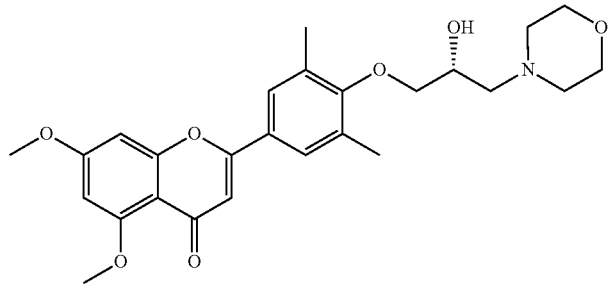 [SMILES: COc1cc(OC)c2c(=O)cc(-c3cc(C)c(OC[C@H](O)CN4CCOCC4)c(C)c3)oc2c1]
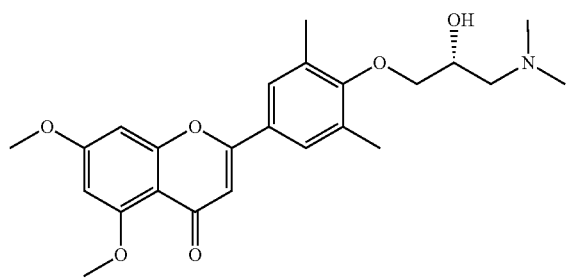
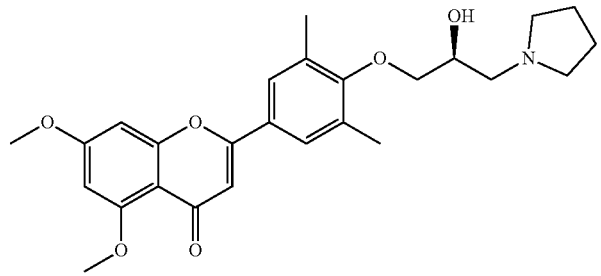 [SMILES: COc1cc(OC)c2c(=O)cc(-c3cc(C)c(OC[C@@H](O)CN4CCCC4)c(C)c3)oc2c1]
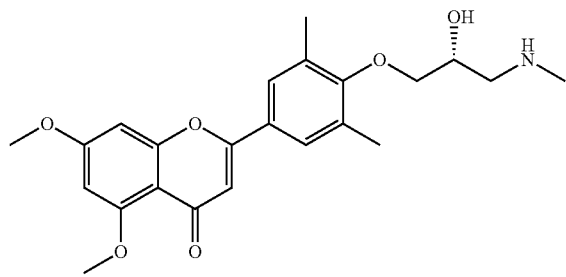
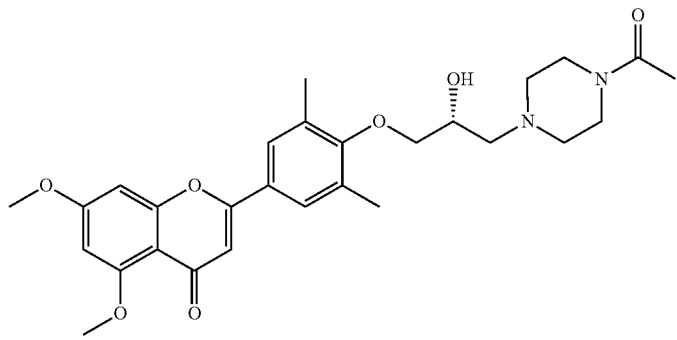 [SMILES: COc1cc(OC)c2c(=O)cc(-c3cc(C)c(OC[C@H](O)CN4CCN(C(C)=O)CC4)c(C)c3)oc2c1]

TABLE 3-continued
The structures of selected molecules.
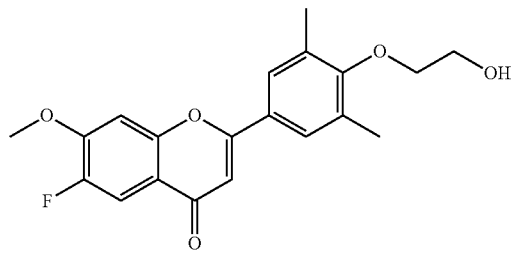 [SMILES: COc1cc2oc(-c3cc(C)c(OCCO)c(C)c3)cc(=O)c2cc1F]
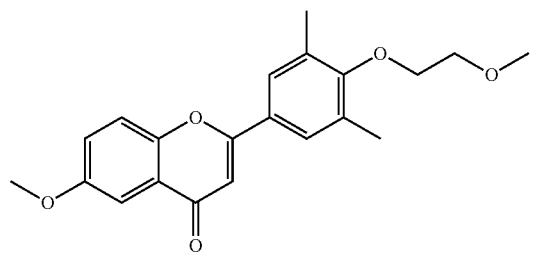
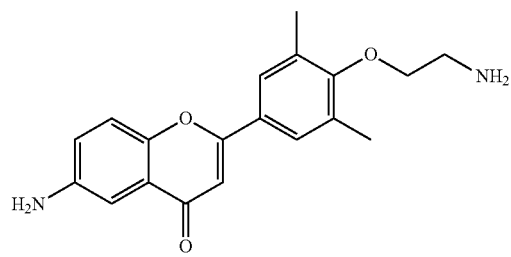 [SMILES: Cc1cc(-c2cc(=O)c3cc(N)ccc3o2)cc(C)c1OCCN]
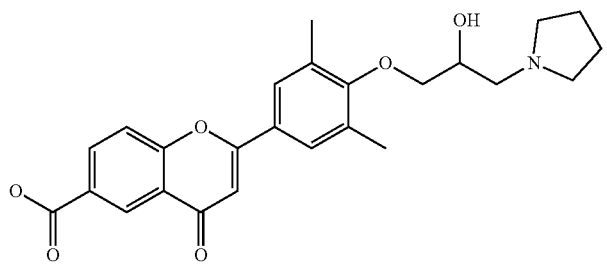 [SMILES: Cc1cc(-c2cc(=O)c3cc(C(=O)O)ccc3o2)cc(C)c1OCC(O)CN1CCCC1]
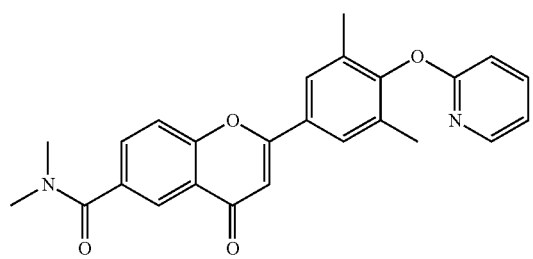 [SMILES: Cc1cc(-c2cc(=O)c3cc(C(=O)N(C)C)ccc3o2)cc(C)c1Oc1ccccn1]
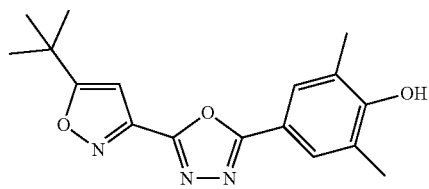 [SMILES: Cc1cc(-c2nnc(-c3cc(C(C)(C)C)on3)o2)cc(C)c1O]

TABLE 3-continued
The structures of selected molecules.
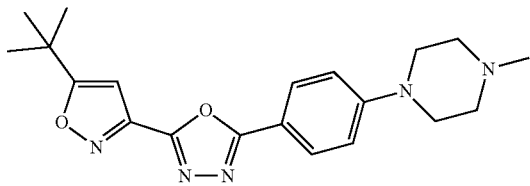 [SMILES: CN1CCN(c2ccc(-c3nnc(-c4cc(C(C)(C)C)on4)o3)cc2)CC1]
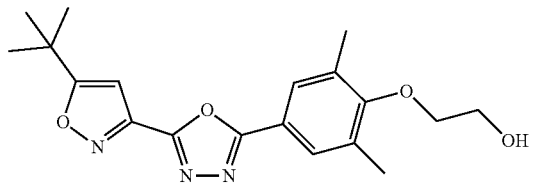 [SMILES: Cc1cc(-c2nnc(-c3cc(C(C)(C)C)on3)o2)cc(C)c1OCCO]
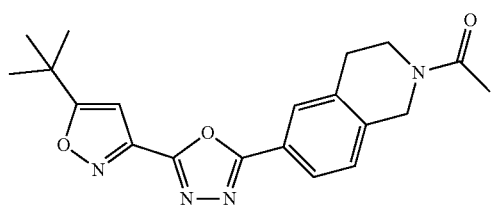 [SMILES: CC(=O)N1CCc2cc(-c3nnc(-c4cc(C(C)(C)C)on4)o3)ccc2C1]
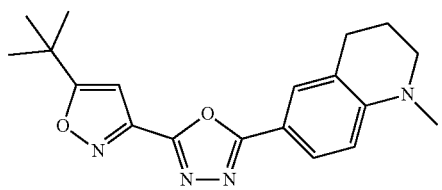 [SMILES: CN1CCCc2cc(-c3nnc(-c4cc(C(C)(C)C)on4)o3)ccc21]
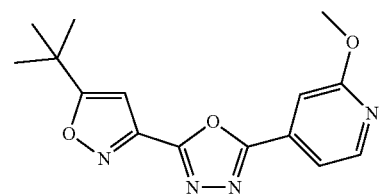 [SMILES: COc1cc(-c2nnc(-c3cc(C(C)(C)C)on3)o2)ccn1]
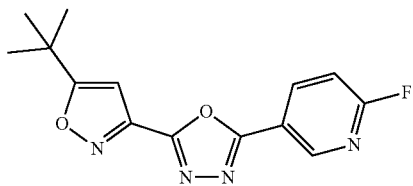 [SMILES: CC(C)(C)c1cc(-c2nnc(-c3ccc(F)nc3)o2)no1]
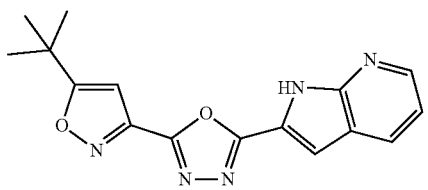 [SMILES: CC(C)(C)c1cc(-c2nnc(-c3cc4cccnc4[nH]3)o2)no1]
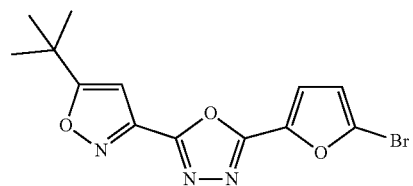 [SMILES: CC(C)(C)c1cc(-c2nnc(-c3ccc(Br)o3)o2)no1]

TABLE 3-continued
The structures of selected molecules.
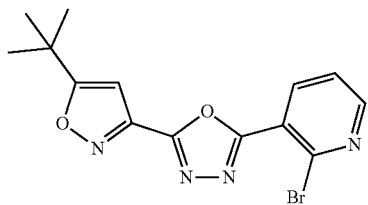 [SMILES: CC(C)(C)c1cc(-c2nnc(-c3cccnc3Br)o2)no1]
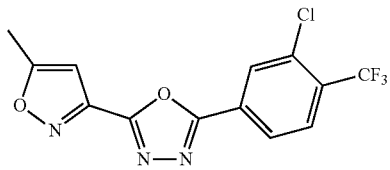 [SMILES: Cc1cc(-c2nnc(-c3ccc(C(F)(F)F)c(Cl)c3)o2)no1]
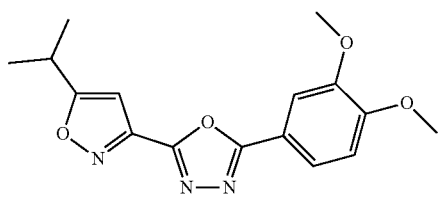 [SMILES: COc1ccc(-c2nnc(-c3cc(C(C)C)on3)o2)cc1OC]
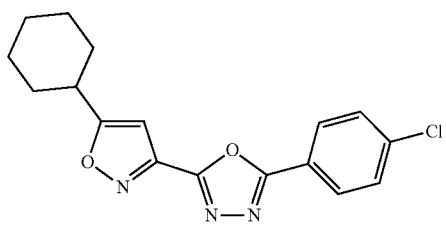 [SMILES: Clc1ccc(-c2nnc(-c3cc(C4CCCCC4)on3)o2)cc1]
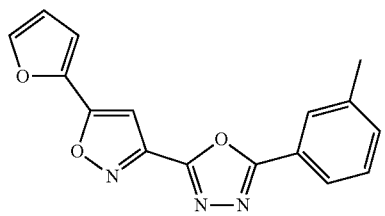 [SMILES: Cc1cccc(-c2nnc(-c3cc(-c4ccco4)on3)o2)c1]
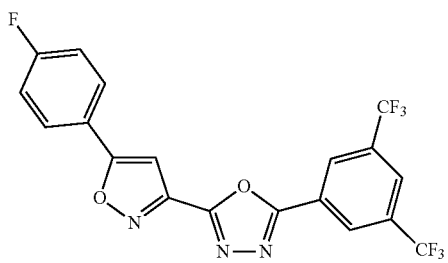 [SMILES: Fc1ccc(-c2cc(-c3nnc(-c4cc(C(F)(F)F)cc(C(F)(F)F)c4)o3)no2)cc1]
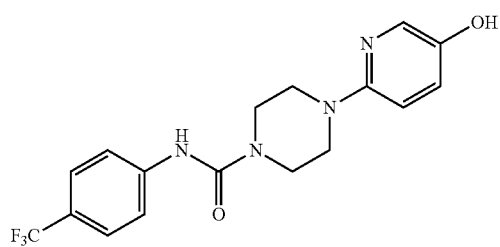 [SMILES: O=C(Nc1ccc(C(F)(F)F)cc1)N1CCN(c2ccc(O)cn2)CC1]

I. Chemical Definitions

Various chemical definitions related to such compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" means that the compound dissolves in water at least to the extent of 0.010 mole/liter or is classified as soluble according to literature precedence.

As used herein, the term "nitro" means $-NO_2$; the term "halo" or "halogen" designates $-F$, $-Cl$, $-Br$ or $-I$; the term "mercapto" means $-SH$; the term "cyano" means $-CN$; the term "azido" means $-N_3$; the term "silyl" means $-SiH_3$; the term "—OTs" means an O-tosyl group; and the term "hydroxyl" means $-OH$.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, $-CH_3$ (Me), $-CH_2CH_3$ (Et), $-CH_2CH_2CH_3$ (n-Pr), $-CH(CH_3)_2$ (iso-Pr), $-CH_2CH_2CH_2CH_3$ (n-Bu), $-CH(CH_3)CH_2CH_3$ (sec-butyl), $-CH_2CH(CH_3)_2$ (iso-butyl), $-C(CH_3)_3$ (tert-butyl), $-CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, $-CH_2F$, $-CH_2Cl$, $-CH_2Br$, $-CH_2OH$, $-CH_2OCH_3$, $-CH_2OCH_2CF_3$, $-CH_2OC(O)CH_3$, $-CH_2NH_2$, $-CH_2NHCH_3$, $-CH_2N(CH_3)_2$, $-CH_2CH_2Cl$, $-CH_2CH_2OH$, $CH_2CH_2OC(O)CH_3$, $-CH_2CH_2NHCO_2C(CH_3)_3$, and $-CH_2Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, piperidyl, piperazinyl, morpholinyl, tetrahydropyranyl, tetrahydrofuranyl, pyrrolidinyl, dithianyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

The term "arylalkyl", used alone or in any combination, refers to an aryl group which may be unsubstituted or substituted as previously defined and which is appended to the parent molecular moiety through an alkyl group.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkylsulfonyl, arylsulfonyl, unsubstituted cycloalkyl, unsubstituted heterocyclyl, unsubstituted aryl, or unsubstituted heteroaryl. Examples of optional substituents include, but are not limited to: $-OH$, oxo ($=O$), $-Cl$, $-F$, Br, $C_{1-4}$alkyl, phenyl, benzyl, $-NH_2$, $-NH(C_{1-4}alkyl)$, $-N(C_{1-4}alkyl)_2$, $-NO_2$, $-S(C_{1-4}alkyl)$, $-SO_2(C_{1-4}alkyl)$, $-CO_2(C_{1-4}alkyl)$, and $-O(C_{1-4}alkyl)$.

The term "ester" as used herein is defined refers to the general formula EOOC; wherein E is alkyl or aryl, as including a group of formula $-COOR$.

The term "alkoxy" means a group having the structure $-OR'$, where R' is an optionally substituted alkyl or cycloalkyl group. The term "heteroalkoxy" similarly means a group having the structure $-OR$, where R is a heteroalkyl or heterocyclyl.

The term "amino" means a group having the structure $-NR'R"$, where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "hydroxyalkyl" as used herein refers to hydroxylated straight or branched chain radicals containing one to ten carbon atoms, as illustrated by, but not limited to 2-propanol, 3-propanol and the like.

The term "alkylamino" as used herein includes mono- and dialkylamino groups, wherein an alkyl group contains from 1 to 6 carbon atoms which may be straight-chained or branched. Typical examples are methylamino, methylethylamino, diethylamino, propylamino, diisopropylamino, and hexylamino.

The term "alkylsulfonyl" as used herein means a moiety having the formula —S(O$_2$)—R', where R' is an alkyl group. R' may have a specified number of carbons (e.g. "C$_{1-4}$ alkylsulfonyl")

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

II. Anti-Inflammatory Agents

In certain aspects of the invention an anti-inflammatory agent may be used in combination with a composition described herein. The anti-inflammatory can be a steroidal or non-steroidal anti-inflammatory.

Steroidal anti-inflammatories for use herein include, but are not limited to fluticasone, beclomethasone, any pharmaceutically acceptable derivative thereof, and any combination thereof. As used herein, a pharmaceutically acceptable derivative includes any salt, ester, enol ether, enol ester, acid, base, solvate or hydrate thereof. Such derivatives may be prepared by those of skill in the art using known methods for such derivatization.

Fluticasone—Fluticasone propionate is a synthetic corticosteroid. Fluticasone propionate is a white to off-white powder and is practically insoluble in water, freely soluble in dimethyl sulfoxide and dimethylformamide, and slightly soluble in methanol and 95% ethanol. In an embodiment, the formulations of the present invention may comprise a steroidal anti-inflammatory (e.g., fluticasone propionate).

Beclomethasone—In certain aspects the steroidal anti-inflammatory can be beclomethasone dipropionate or its monohydrate. The compound may be a white powder and is very slightly soluble in water (Physicians' Desk Reference), very soluble in chloroform, and freely soluble in acetone and in alcohol.

Providing steroidal anti-inflammatories according to the present invention may enhance the compositions and methods of the invention by, for example, attenuating any unwanted inflammation. Examples of other steroidal anti-inflammatories for use herein include, but are not limited to, betamethasone, triamcinolone, dexamethasone, prednisone, mometasone, flunisolide and budesonide.

In accordance with yet another aspect of the invention, the non-steroidal anti-inflammatory agent may include aspirin, sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, ammopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx®, and/or tenoxicam.

III. Antiviral Agents

In certain aspects of the invention an anti-viral agent may be used in combination with a composition described herein. Anti-viral agents include, but are not limited to nucleoside analogs, antisense RNA, or monoclonal antibodies (see for example Hruska et al., 1980, *Antimicrobial Agents and Chemotherapy* 17:770-75; Leaman et al., 2002, *Virology* (New York NY) 292:70-77; Lai et al., 2008, *Mol Ther.* 16:1120-28).

Antiviral agents herein include, but are not limited to synthetic ribonucleosides (ribavirin), anti-sense oligonucleotides, interfering nucleic acids, neutralizing antibodies, interferons or any combination thereof. As used herein, a pharmaceutically acceptable derivative includes any salt, ester, enol ether, enol ester, acid, base, solvate or hydrate thereof. Nucleotides may also be encapsulated into liposomes for more efficient intracellular transfer. These compounds may be administered systemically, via aerosol, or nebulization. Such derivatives may be prepared by those of skill in the art using known methods for such derivatization.

Ribavirin is a nucleoside analog with broad-spectrum inhibitory activities towards RNA viruses used in severe RSV and hemorrhagic fever infections.

Antisense oligonucleodies and modified nucleic acids, such as morpholino oligonucleotides, targeted towards RSV genomic RNA have been used to reduce viral replication.

Humanized monoclonal antibodies (palivizumab, Synagis) raised against RSV structural proteins have been used for the prophylaxis and treatment of patients at high risk for RSV disease.

Interferons—interferons are immune regulating hormones that limit viral replication. These can be used alone or in combination with ribavirin to enhance anti-viral immunity.

IV. Formulation and Administration

The pharmaceutical compositions disclosed herein may be administered, for example, via the respiratory system of a subject. In certain aspects the compositions are deposited in the lung by methods and devices known in the art. Therapeutic compositions described herein may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations contain a preservative to prevent the growth of microorganisms. In certain aspects the compounds described herein can be formulated for extended release as a nanoparticles (NPs) formulation, made from biodegradable and biocompatible polymers. Such therapeutic formulations offer a platform for reducing the number of doses, reduce toxicity without altering its therapeutic effects, protect the drug from inactivation (due to protein binding or metabolism of the drug), and provide a sustained release stable for long periods of time and have greater specificity against target tissues (given by the functionalization of the molecule).

The pharmaceutical forms suitable for inhalation include sterile aqueous solutions or dispersions and sterile powders for the extemporaneous preparation of sterile inhalable solutions or dispersions. In all cases the form is typically sterile and capable of inhalation directly or through some intermediary process or device. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like.

Some variation in dosage will necessarily occur depending on the condition of the subject being treated and the particular circumstances involving exposure or potential exposure. The person responsible for administration will, in any event, determine the appropriate dose for the individual subject. Moreover, for human administration, preparations should meet sterility, pyrogenicity, general safety, and purity standards as required by FDA Office of Biologics standards or other similar organizations.

Sterile compositions are prepared by incorporating the active components in the required amount in the appropriate solvent with various other ingredients enumerated above, as required, followed by, for example, filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some methods of preparation are vacuum-drying and freeze-drying techniques which yield a powder of the component(s) and/or active ingredient(s) plus any additional desired ingredient from a previously sterile-filtered solution.

In certain embodiments the compounds can be associated with the surface of, directly or indirectly conjugated to, encapsulated within, surrounded by, dissolved in, or dispersed throughout a polymeric matrix. The phrase "loaded into", "loaded onto", "incorporated into", or "included in" are used interchangeably to generally describe the association of the compound with the particle without imparting any further meaning as to where or how the compound is associated with the particle.

The amount of compound present in a particle (entrapment efficiency) can be at least about 10% to as high as about 98% w/w. In some embodiments, the entrapment efficiency can be about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 98% (w/w).

A. Nanoparticles

The composition (e.g., encapsulated compound) comprises a nanoparticle, the nanoparticle further comprising a polymer and at least one compound. The term "particle," "nanoparticle," "biodegradable polymeric nanoparticle," or the abbreviation "NP" for nanoparticle, as used herein, can refer to particles between 10, 100, 200, 300, 400, 500, to 600, 700, 800, 900, 1000 nanometers (nm) in diameter, including all values and ranges there between, and are used interchangeably. In certain aspects the NPs can have a diameter of 50 to 150 nm. The compounds described herein can be incorporated into a suitable particle (or nanoparticle) to aid in the delivery of the drug to target cells, to increase the stability of the composition, to minimize potential toxicity of the composition, and/or a combination thereof. A variety of nanoparticles are suitable for delivering a compound.

The size of the particle can influence the ability of the particle to rapidly penetrate through mucosal barriers. For instance, the nanoparticle can have small particle size for successful delivery through a mucosal barrier. In some embodiments, the diameter of a nanoparticle can be at least 10 nm, at least 20 nm, at least 30 nm, at least 40 nm, at least 50, at least 60 nm, at least 70 nm, at least 80 nm, at least 90 nm, or at least 100 nm. In other embodiments, the particle can be greater than about 100 nm in diameter. For example, the diameter of the nanoparticle can be at least 110 nm, at least 120 nm, at least 130 nm, at least 140 nm, at least 150 nm, at least 160 nm at least 170 nm, at least 180 nm, at least 190 nm, or at least 200 nm. In an exemplary embodiment, the nanoparticle can be less than 220 nm in diameter. In still other embodiments, the particle can be about or less than about 100 nm in diameter.

In some embodiments, the particle can have a surface charge that is positive or negative. For example, in certain embodiments where a nanoparticle has a negative surface charge, the surface charge can be at least −40 millivolts (mV), at least −35 mV, at least −30 mV, at least −25 mV, at least −20 mV, no greater than −10 mV, no greater than −15 mV, no greater than −20 mV, no greater than −25 mV, or any combination thereof. In one example, a nanoparticle can have a negative surface charge of at least −30 mV to no greater than −10 mV. In other examples a nanoparticle has a positive surface charge, the surface charge can be at least 2 millivolts (mV), at least 15 mV, at least 20 mV, at least 25 mV, or at least 30 mV, no greater than 40 mV, no greater than 35 mV, no greater than 30 mV, no greater than 25 mV, or any combination thereof.

In some embodiments, the particle can have an osmolarity of less than about 1000 mOsm/kg. In other embodiments, the particle can have an osmolarity less than about 500 mOsm/kg. For example, the particle can have an osmolarity of about 50 mOsm/kg, about 100 mOsm/kg, about 150 mOsm/kg, about 200 mOsm/kg, about 250 mOsm/kg, about 300 mOsm/kg, about 350 mOsm/kg, about 400 mOsm/kg, about 410 mOsm/kg, about 420 mOsm/kg, about 430 mOsm/kg, about 440 mOsm/kg, about 450 mOsm/kg, about 460 mOsm/kg, about 470 mOsm/kg, about 480 mOsm/kg, or about 490 mOsm/kg. In another embodiment, the particle can have an osmolarity of at least 500 mOsm/kg to no greater than 1000 mOsm/kg. For example, the particle can have an osmolarity of about 500 mOsm/kg, about 600 mOsm/kg, about 700 mOsm/kg, about 800 mOsm/kg, about 900 mOsm/kg, or about 1000 mOsm/kg.

B. Biodegradable Polymer

Each particle can include one or more biodegradable polymers. An example of such a particle comprising a biodegradable polymer and methods of making the particle is disclosed in patent application publication number US 2011/0236437, which is incorporated herein by reference in its entirety. Briefly, a "polymer," as used herein, is given its ordinary meaning as used in the art, i.e., a molecular structure including one or more repeat units (monomers), connected by covalent bonds. The repeat units can all be identical, or in some cases, there can be more than one type of repeat unit present within the polymer. A polymer can be natural (e.g., biologically derived) or unnatural (e.g., synthetically derived). Polymers can be homopolymers or copolymers including two or more monomers. Copolymers can be random, block, or can include a combination of random and block sequences. If more than one type of repeat unit is present within the polymer, then the polymer is said to be a "copolymer." It is to be understood that in any aspect employing a polymer, the polymer can be a copolymer.

A biodegradable polymer is able to degrade, chemically and/or biologically, within a physiological environment, such as within the body. For instance, the polymer can be one that hydrolyzes spontaneously upon exposure to water (e.g., within a subject), or degrades upon exposure to heat (e.g., at temperatures of 42° C.). Degradation of a polymer can occur at varying rates, depending on the polymer or copolymer used. For example, the half-life of the polymer (the time at which 50% of the polymer is degraded into monomers and/or other nonpolymeric moieties) can be on the order of days or weeks, depending on the polymer. The polymers can be biologically degraded, e.g., by enzymatic activity or cellular machinery. In some cases, the polymers can be broken down into monomers and/or other nonpolymeric moieties that cells can either reuse or dispose of without significant toxic effect on the cells (for example, polylactide can be hydrolyzed to form lactic acid, polyglycolide can be hydrolyzed to form glycolic acid, etc.).

In some embodiments, the biodegradable polymer can be a natural polymer. In other embodiments, biodegradable the polymer can be a synthetic polymer. Non-limited examples of natural and synthetic polymers useful in the preparation of biodegradable particles can include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids. poly(ortho esters), and polyesters. Non-limiting examples of polyesters can include polymers including, but not limited to, polycaprolactone, or copolymers including, but not limited to, lactic acid and glycolic acid units, such as poly(lactic acid-coglycolic acid) and poly(lactide-co-glycolide), collectively referred to herein as "PLGA"; and homopolymers including glycolic acid units, and lactic acid units, such as poly-L-lactic acid, poly-D-lactic acid, poly-D,L-lactic acid, poly-L-lactide, poly-D-lactide, and poly-D,L-lactide. In some embodiments, the polymer can be PLGA.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258; 6,794,357; 6,737,045; and 6,488,953—all of which are incorporated by reference. According to the invention, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), Aerotech II® or the like.

All such inhalation devices can be used for the administration of a pharmaceutical composition in an aerosol. Such aerosols may comprise either solutions (both aqueous and non-aqueous) or solid particles. Metered dose inhalers typically use a propellant gas and require actuation during inspiration. See, e.g., WO 98/35888 and WO 94/16970. Dry powder inhalers use breath-actuation of a mixed powder. See U.S. Pat. Nos. 5,458,135 and 4,668,218; PCT publications WO 97/25086, WO 94/08552 and WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a composition described herein.

A spray comprising a pharmaceutical composition described herein can be produced by forcing a suspension or solution of a composition through a nozzle under pressure.

The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition described herein can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer.

In an ultrasonic nebulizer, high-frequency electrical energy is used to create vibrational, mechanical energy, typically employing a piezoelectric transducer. This energy is transmitted to the composition creating an aerosol.

In a metered dose inhaler (MDI) or in other device that us propellant, a propellant, a composition, and any excipients or other additives are contained in a canister as a mixture with a compressed gas. Actuation of the metering valve releases the mixture as an aerosol. Pharmaceutical compositions for use with a metered-dose inhaler device will generally include a finely divided powder containing a composition of the invention as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a subject. The preparation of an aqueous composition that contains a polypeptide or peptide as an active ingredient is well understood in the art.

Certain aspects are directed to methods of treating a subject with an inflammatory condition comprising administering an effective amount of a BRD4 inhibitor, such as the compounds described herein. The method can further include administering an anti-inflammatory compound. In a particular aspect the inflammatory condition is a virus induced inflammatory condition. The virus can be a respiratory virus, and in particular a respiratory syncytial virus (RSV). The methods can further include administering an anti-viral compound.

A method of treating a subject with an inflammatory bowel disease comprising administering an effective amount of a BRD4 inhibitor such as the compounds described herein. The inflammatory bowel disease can be acute ulcerative colitis (UC), anti-TNF resistant UC, crohns disease, and/or crohn's induced fibrosis.

Certain aspects are directed to methods of treating a subject with airway inflammation comprising administering an effective amount of a BRD4 inhibitor, such as those compounds described herein. The airway inflammation is associated with a lung disease. The lung disease can be a chronic obstructive lung disease (OLD). In certain aspects the OLD is chronic obstructive pulmonary disease (COPD), asthma, cystic fibrosis (CF), or bronchiectasis.

V. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A. Materials and Methods

Synthetic ds RNA analog polyinosinic-polycytidylic acid (poly(I:C) was used at 10 μg/ml (Sigma Aldrich) and TGFβ was used at 10 ng/ml in cell culture medium (PeproTech, Rocky Hill, N.J.). (+)-JQ1 was commercially available. New selective BRD4 inhibitors ZL0420 and ZL0454 were designed and synthesized in house with details presented in the ensuing discussions.

hSAEC cell culture. A human telomerase-immortalized small airway epithelial cell (hSAEC) line was grown in small airway epithelial cell growth medium (SAGM) (Lonza, Walkersville, Md.) in a humidified 5% $CO_2$ atmosphere.

Ethics statement. Animal experiments were performed according to the NIH Guide for Care and Use of Experimental Animals and approved by the University of Texas Medical Branch (UTMB) Animal Care and Use Committee (approval no. 1312058). Mice were housed under pathogen-free conditions with food and water ad libitum.

Construction of the RelA conditional knockout. Construction of the floxxed (fl) RelA$^{fl/fl}$ mouse containing loxP sites inserted in Introns 3 and 9 was described (Ijaz et al. *BMC Developmental Biology* 2016, 16:32). RelA$^{fl/fl}$ mice were crossed with mice with a taxmofen-inducible CRE inserted into the 3' UTR of the secretoglobin, family 1A, member 1 (Scgb1a1) gene (Scgb1a1-CreER®) in the C57BL/6JN background (Rawlins et al. *Cell Stem Cell.* 2009, 4(6):525-34). For reporter studies, RelA$^{fl/fl}$/Scgb1a1-CreER™ mice were crossed into the B6.129(Cg)-Gt(ROSA)26Sortm4 (ACTB-tdTomato-EGFP)Luo/J (Jackson Labs, stock #007676).

Presence of RelA$^{CKO}$ alleles was determined by PCR using RelAFlx F, TGCAAACAGACCTCCTTTGTCTTGA (SEQ ID NO:1), and RelAFlx R, TCCTGAGACCAGACTCCTCCTCC (SEQ ID NO:2), primers which provides a 450 bp product if the floxxed (knockout) allele is present or 270 bp product for a WT allele.

Tamoxifen treatment. 3-4 week old mice, were injected with Tamoxifen (Sigma T5648) 1 mg/day intraperitoneally for 10 days. Tamoxifen was dissolved in 10% ethanol and 90% corn oil for 10 mg/ml working solution. After 3 weeks, mice were challenged with poly(I:C) intraperitoneally, euthanized and tissues were harvested for characterization.

Poly(I:C) challenge. Under mild anesthesia, mice were given poly(I:C) challenges (500 μg/dose in 50 μL PBS) via the intranasal (IN) route.

Quantitative real-time reverse transcription-PCR (Q-RT-PCR). Total RNA was extracted using acid guanidinium phenol extraction (Tri Reagent; Sigma). Quality of the total RNA was confirmed spectrophotometrically using the 260/280 nm ratio. 1 μg of RNA was reverse-transcribed using SuperScript III in a 20-μl reaction mixture (Brasier et al. *J Virol.* 2011, 85(22):11752-69; Tian et al. *J Virol.* 2013, 87(12):7075-92). Relative changes in gene expression were quantified using gene specific primers and the ΔΔCT method (Brasier et al. *J Virol.* 2011, 85(22):11752-69; Tian et al. *J Virol.* 2013, 87(12):7075-92). Data shown is the fold-change in mRNA abundance normalized to cyclophilin.

Confocal Immunofluorescence Microscopy. For immunofluorescence staining, hSAECs were plated on rat tail collagen-treated cover glasses and stimulated as indicated. The cells were fixed with 4% paraformaldehyde in PBS and incubated with 0.1 M ammonium chloride for 10 min. Cells were permeabilized with 0.5% Triton X-100 in PBS, followed by incubation in blocking buffer (5% goat serum, 0.1% IGEPAL CA-630, 0.05% NaN$_3$, and 1% BSA) and incubated with anti-RelA (Santa Cruz) in incubation buffer (0.1% IGEPAL CA-630, 0.05% NaN$_3$, and 2% BSA) overnight at 4° C. After washing, cells were stained with Alexa Fluor conjugated goat anti-rabbit IgG (Life Technologies) in incubation buffer for 1 h. Where indicated, nuclei were counter-stained with 4',6-diamidino-2-phenylindole (DAPI, Thermofisher Scientific). The cells were visualized with a LSM510 fluorescence confocal microscope at a magnification of 63× (Kalita et al. *BioMed Research International.* 2013, 2013:505864; Tian et al. *BMC Genomics.* 2015, 16(1):529).

Immunofluorescence of Lung Sections. Formalin-fixed, paraffin-embedded sections from lungs of mice were rehydrated using serial concentrations of ethanol. For immunohistochemistry (IHC), antigen retrieval was performed with antigen unmasking solution based on recommendations from Abcam (TE buffer, PH 9.0). Paraffin-embedded sections were blocked in blocking buffer (5% goat serum, 0.1% IGEPAL CA-630, 0.05% NaN3, and 1% BSA) followed incubated with rabbit anti-RelA, anti-CC10, or anti-acetyl H3K122 Abs (Abcam) in incubation buffer (0.1% IGEPAL CA-630, 0.05% NaN3, and 2% BSA) overnight at 4° C. Normal anti-rabbit IgG were used as staining specificity controls. After washing, cells were stained with Alexa Fluor 488- or 568-conjugated goat anti-rabbit IgG (Life Technologies) in incubation buffer for 1 h, then visualized with a LSM510 fluorescence confocal microscope, magnification 63× (Kalita et al. *BioMed Research International.* 2013, 2013:505864; Tian et al. *BMC Genomics.* 2015, 16(1):529).

Evaluation of airway inflammation. Cellular recruitment into the airway lumen was assessed in the bronchoalveolar lavage fluid (BALF). Lungs were perfused twice with 1 mL of sterile PBS (pH 7.4) to obtain the BALF. Total cell counts were determined by trypan blue staining 50 μl of BALF and counting viable cells using a hemocytometer. Differential cell counts were performed on cytocentrifuge preparations (Cytospin 3; Thermo Shandon, Pittsburgh, Pa.) stained with Wright-Giemsa. A total of 300 cells were counted per sample using light microscopy. Formalin-fixed lungs were embedded in paraffin, sectioned at a 4 μm thickness, and stained with hematoxylin and eosin or Masson's trichrome. Microscopy was performed on a NIKON Eclipse Ti System.

Cytokine Bio-Plex assay. BALF samples were centrifuged (800× g for 5 min at 4° C.) and the cytokines quantitated in the supernatant using Bio-Plex Pro™ Mouse Cytokine Assay (Bio-Rad, Hercules, Calif.) with recombinant cytokine standards (in triplicate). Readings were performed on a Bioplex® 200™ system (Bio-Rad). Data analysis was performed using Bio-Plex Manager™ Software Version 6.0 Build 617 (Bio-Rad).

TABLE 4

IC$_{50}$ values of selected compounds

|  | JQ1 | MS436 | RVX | ZJ392 | ZL420 | ZL454 | H510 | ZL468 |
|---|---|---|---|---|---|---|---|---|
| IL-6 IC$_{50}$ (μM) | 1.02 | 1.14 | 3.29 | 1.88 | 0.45 | 0.69 | 3.2 | 2.8 |
| CIG5 IC$_{50}$ (μM) | 0.95 | 1.62 | 1.66 | 1.34 | 0.42 | 0.6 | 3.5 | 2.6 |

TABLE 5

IC$_{50}$ values of selected new compounds

| Compound | IC$_{50}$-IL-6 (μM) | IC$_{50}$-CIG5 (μM) |
|---|---|---|
| ZL0591 | 0.24 | 0.4 |
| ZL0590 | 0.39 | 0.18 |
| ZL0556 | 2.4 | 0.85 |
| ZL0518 (aka ZL0420) | 0.29 | 2.4 |
| ZL0513 | 1.1 | 0.52 |
| ZL0165 | 4.8 | 8.6 |
| ZL0482 (positive control) | 1.4 | 1.7 |
| ZL0516 | 0.31 | 0.28 |
| ZL0586 | 4.4 | 10.6 |
| ZL0589 | 20.3 | 25.8 |

BRD4 inhibitor synthesis and characterization.

(E)-6-((2-Amino-4-hydroxy-5-methylphenyl)diazenyl)-3,4-dihydroquinolin-2(1H)-one (ZL0420). To a solution of 6-amino-3,4-dihydroquinolin-2(1H)-one (168 mg, 1.04 mmol) and HCl (concentrated aq, 416 μL, 6.24 mmol) in MeOH (6 mL) and CH$_3$CN (6 mL) at 0° C. (pre-cooled for 15 min) under N$_2$, tert-butyl nitrite (107 mg, 1.04 mmol) was added over 15 min and then stirred at 0° C. for 45 min to get a reaction solution. Meanwhile, 5-amino-2-methylphenol (128 mg, 1.04 mmol) and K$_2$CO$_3$ (718 mg, 5.2 mmol) were dissolved in MeOH (2.5 mL) and H$_2$O (18 mL) and degassed for 15 min. To this mixture, the previous reaction solution was added over 15 min and stirred at 0° C. for 1 h. The reaction was monitored by the TLC analysis, and after its completion, 10% HCl (aq) was added to adjust pH=1. The precipitate was filtered to provide the desired product (250 mg, yield 81%) as a dark red solid. HPLC purity 98.3% ($t_R$=16.59 min). $^1$H NMR (300 MHz, DMSO-d$_6$) δ 10.25 (s, 1H), 7.64 (s, 1H), 7.59 (d, J=8.6 Hz, 2H), 7.36 (s, 1H), 6.93 (d, J=8.3 Hz, 1H), 6.25 (s, 1H), 2.95 (t, J=7.4 Hz, 2H), 2.47 (m, 2H), 2.03 (s, 3H). $^{13}$C NMR (75 MHz, DMSO-d$_6$) δ 170.64, 160.39, 148.35, 145.73, 139.21, 130.98, 126.96, 124.67, 121.85, 120.73, 115.83, 114.51, 101.07, 30.75, 25.31, 15.66. ESI-MS (M+H)$^+$ m/z 297.1. HRMS (M+H)$^+$ m/z=297.1342 (calcd for C$_{16}$H$_{17}$N$_4$O$_2$: 297.1352).

(E)-4-((2-Amino-4-hydroxy-5-methylphenyl)diazenyl)-N-cyclopentylbenzene sulfonamide (ZL0454). To a solution of 4-amino-N-cyclopentylbenzenesulfonamide (96 mg, 0.4 mmol) and HCl (concentrated aq, 160 μL, 2.4 mmol) in MeOH (3 mL) and CH$_3$CN (3 mL) at 0° C. (pre-cooled for 15 min) under N$_2$, tert-butyl nitrite (48 mg, 0.4 mmol) was added over 15 min and then stirred at 0° C. for 45 min to get a reaction solution. Meanwhile, 5-amino-2-methylphenol (52 mg, 0.4 mmol) and K$_2$CO$_3$ (276 mg, 2.0 mmol) were dissolved in MeOH (1 mL) and H$_2$O (8 mL) and degassed for 15 min. To this mixture, the previous reaction solution was added over 15 min and stirred at 0° C. for 1 h. The reaction was monitored by the TLC analysis, and after its completion, 10% HCl was added to adjust pH=1. The precipitate was filtered to provide the desired product (117 mg, yield 78%) as a red solid. HPLC purity 98.1% ($t_R$=18.38 min). $^1$H NMR (300 MHz, DMSO-d$_6$) δ 8.03 (t, J=7.2 Hz, 2H), 7.85 (d, J=8.7 Hz, 2H), 7.68 (d, J=6.6 Hz, 1H), 6.42 (d, J=6.3 Hz, 1H), 3.42 (m, 1H), 2.05 (s, 3H), 1.65-1.48 (m, 4H), 1.44-1.24 (m, 4H). $^{13}$C NMR (75 MHz, DMSO-d$_6$) δ 166.55, 139.65, 130.75, 128.27, 119.99, 100.15, 54.95, 32.90, 23.27, 16.10. MS (M+H)$^+$ m/z 375.1. HR ESI-MS (M+H)$^+$ m/z=375.1530 (calcd for C$_{18}$H$_{23}$N$_4$O$_3$S: 375.1538).

EC$_{50S}$ were determined in cultured hSAECs measuring inhibition of poly(I:C) induced FN1 gene expression in Q-RT-PCR assays.

Time resolved (TR)-fluorescence resonance energy transfer (TR-FRET). Binding affinities to the bromodomains of BRD-4 and BRD-2 were quantitated using commercially available TR-FRET Assay kit (Cayman chemicals). The 'donor' fluorophore is human BD1 or BD2 of BRD-4 and BRD-2 (amino acids 49-170) directly labeled with a europium (Eu3+) chelate. A biotinylated peptide containing target acetylated lysine serves as the ligand for BD1 or BD2 of BRD4 and BRD2. Allophycocyanin (APC)-labeled avidin binds with high affinity to the peptide substrate via the biotin moiety and serves as the 'acceptor' fluorophore. Inhibitory concentration at 50% (IC$_{50}$) was estimated from the TR-FRET curve vs log of inhibitor concentration.

TABLE 6

IC$_{50}$ for BRD-2 and -4 bromodomains BD1 and BD2. Affinities determined by TR-FRET (values are in nM).

| Bromodomain | JQ1 | ZL420 | ZL454 |
|---|---|---|---|
| BRD4-BD1 | 92 | 27 | 49 |
| BRD4-BD2 | 62 | 32 | 32 |
| BRD2-BD1 | 78 | 803 | 772 |
| BRD2-BD2 | 52 | 1736 | 1836 |

Abbreviations:
BD, bromodomain.

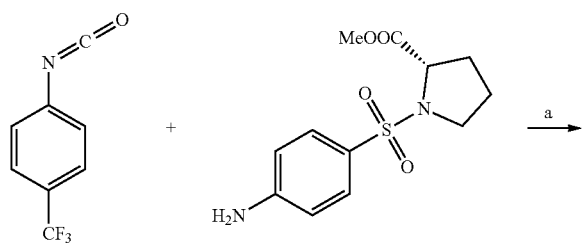

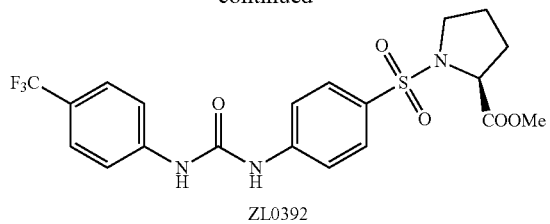

ZL0392

Reagents and conditions: (a) DCM, rt, 96%.

Synthesis of Methyl ((4-(3-(4-(trifluoromethyl)phenyl)ureido)phenyl)sulfonyl)-L-prolinate (ZL0392). A solution of methyl ((4-aminophenyl)sulfonyl)-L-prolinate (ZL0387) (50 mg, 0.176 mmol) and 1-isocyanato-4-(trifluoromethyl) benzene (40 mg, 0.212 mmol) in 5 mL of DCM was stirred at rt overnight. Then the mixture was concentrated directly and the residue was purified by PTLC (DCM/MeOH=100:1) to give the desired product (40 mg, 96%) as a white solid. HPLC purity 99.9% ($t_R$=19.33 min). $^1$H NMR (300 MHz, CDCl$_3$) δ 8.02 (s, 1H), 7.96 (s, 1H), 7.77 (d, J=8.8 Hz, 2H), 7.68-7.51 (m, 6H), 4.27 (dd, J=7.7 Hz, 5.1 Hz, 1H), 3.72 (s, 3H), 3.52 (dd, J=5.8 Hz, 3.5 Hz, 1H), 3.32-3.19 (m, 1H), 2.13-1.90 (m, 3H), 1.77 (dd, J=10.8, 5.4 Hz, 1H). $^{13}$C NMR (75 MHz, CDCl$_3$) δ 173.03, 152.24, 143.98, 141.66, 129.90, 128.64, 126.24, 126.19, 119.05, 119.00, 60.72, 52.74, 48.75, 30.92, 24.66. ESI-MS (M+H)$^+$ m/z 472.1. HR ESI-MS (M+H)$^+$ m/z=472.1166 (calcd for C$_{20}$H$_{21}$F$_3$N$_3$O$_5$S: 472.1154)

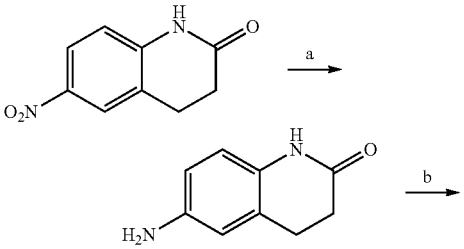

ZL0417

Reagents and conditions:
(a) Zn, NH$_4$Cl, MeOH/H$_2$O, 80° C., quant.
(b) 2,6-dimethylphenol, tert-butyl formate, 38% HCl (aq), K$_2$CO$_3$, MeOH/CH$_3$CN/H$_2$O, 0° C., 40%.

Synthesis of 6-Amino-3,4-dihydroquinolin-2(1H)-one (ZL0394). 6-Nitro-3,4-dihydroquinolin-2(1H)-one (1.0 g, 5.2 mmol) was dissolved in 40 mL of EtOH, and then NH$_4$Cl (2.76 g, 52 mmol) in 20 mL of H$_2$O and Zn dust (2.37 g, 36.4 mmol) were added. After refluxing at 80° C. for 1 h, the mixture was filtered to remove Zn dust. The filtration was concentrated to give the desired product (1.8 g, including partial NH$_4$Cl) as a gray solid. $^1$H NMR (300 MHz, DMSO-d$_6$) δ 9.67 (s, 1H), 6.55 (d, J=8.2 Hz, 1H), 6.42-6.31 (m, 2H), 2.70 (t, J=7.5 Hz, 2H), 2.33 (dd, J=8.5 Hz, 6.5 Hz, 2H).

Synthesis of (E)-6-((4-hydroxy-3,5-dimethylphenyl)diazenyl)-3,4-dihydroquinolin-2(1H)-one (ZL0417). Compound ZL0417 was prepared in 40% yield by a procedure similar to that used to prepare compound ZL0404. The title compound was obtained as a red solid. HPLC purity 97.0% ($t_R$=17.82 min). $^1$H NMR (300 MHz, DMSO-$d_6$) δ 10.38 (s, 1H), 9.01 (s, 1H), 7.65 (s, 2H), 7.50 (s, 2H), 7.14 (s, 1H), 7.00 (d, J=7.8 Hz, 1H), 2.98 (s, 2H), 2.26 (s, 6H), 1.94 (d, J=7.4 Hz, 2H). $^{13}$C NMR (75 MHz, DMSO-$d_6$) δ 170.80, 156.82, 147.74, 145.42, 140.83, 139.31, 136.59, 134.42, 125.29, 123.40, 121.35, 115.92, 30.60, 25.19, 17.17. ESI-MS (M+H)$^+$ m/z 296.1. HR ESI-MS (M+H)$^+$ m/z=296.1391 (calcd for $C_{17}H_{18}N_3O_2$:296.1399)

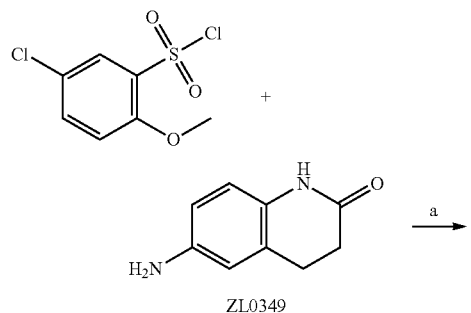

Reagents and conditions: (a) Et$_3$N, DMF, rt, 29%.

Synthesis of 5-chloro-2-methoxy-N-(2-oxo-1,2,3,4-tetrahydroquinolin-6-yl)benzenesulfonamide (ZL0419). To a solution of ZL0349 (70 mg, 0.43 mmol) and Et$_3$N (87 mg, 0.86 mmol) in 5 mL DMF, 5-chloro-2-methoxybenzenesulfonyl chloride (156 mg, 0.65 mmol) was added. After stirring at rt for 1 h, the mixture was poured into 20 mL ice-water. The precipitate was filtered to get the desired product (45 mg, 29%) as a white solid. HPLC purity 98.9% ($t_R$=16.18 min). $^1$H NMR (300 MHz, DMSO-$d_6$) δ 9.97 (s, 1H), 9.85 (s, 1H), 7.61 (s, 1H), 7.24 (dd, J=10.2, 6.8 Hz, 2H), 6.94-6.79 (m, 2H), 6.67 (d, J=8.4 Hz, 1H), 3.91 (s, 3H), 2.81-2.71 (m, 2H), 2.36 (t, J=7.5 Hz, 2H). $^{13}$C NMR (75 MHz, DMSO-$d_6$) δ 170.38, 155.70, 135.72, 134.90, 133.70, 131.74, 129.59, 128.53, 127.45, 124.68, 124.05, 121.63, 120.67, 115.80, 115.36, 57.00, 30.58, 25.25. ESI-MS (M+H)$^+$ m/z 367.1. HR ESI-MS (M+H)$^+$ m/z=367.0506 (calcd for $C_{16}H_{16}N_2O_4$SCl:367.0519).

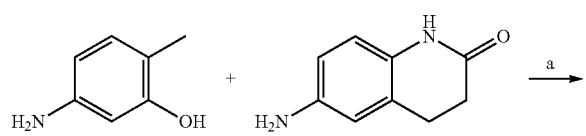

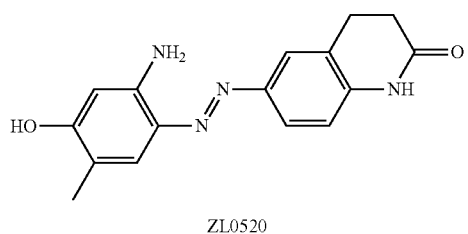

Reagents and conditions:
(a) tert-butyl formate, 38% HCl (aq), K$_2$CO$_3$, MeOH/CH$_3$CN/H$_2$O, 0° C., 81%.

Synthesis of (E)-6-((2-amino-4-hydroxy-5-methylphenyl)diazenyl)-3,4-dihydroquinolin-2(1H)-one (ZL0420). Compound ZL0420 was prepared in 81% yield by a procedure similar to that used to prepare compound ZL0404. The title compound was obtained as a red solid. $^1$H NMR (300 MHz, DMSO-$d_6$) δ 10.40 (s, 1H), 7.74 (d, J=30.7 Hz, 3H), 7.06 (s, 1H), 6.66 (s, 1H), 3.48 (s, 2H), 3.02 (s, 2H), 2.21 (s, 3H). $^{13}$C NMR (75 MHz, DMSO-$d_6$) δ 183.78, 170.69, 151.88, 139.55, 137.00, 136.70, 133.96, 127.59, 125.52, 119.44, 119.00, 116.24, 111.71, 30.44, 25.22, 17.70. ESI-MS (M+H)$^+$ m/z 297.1. HR ESI-MS (M+H)$^+$ m/z=297.1345 (calcd for $C_{16}H_{17}N_4O_2$:297.1352).

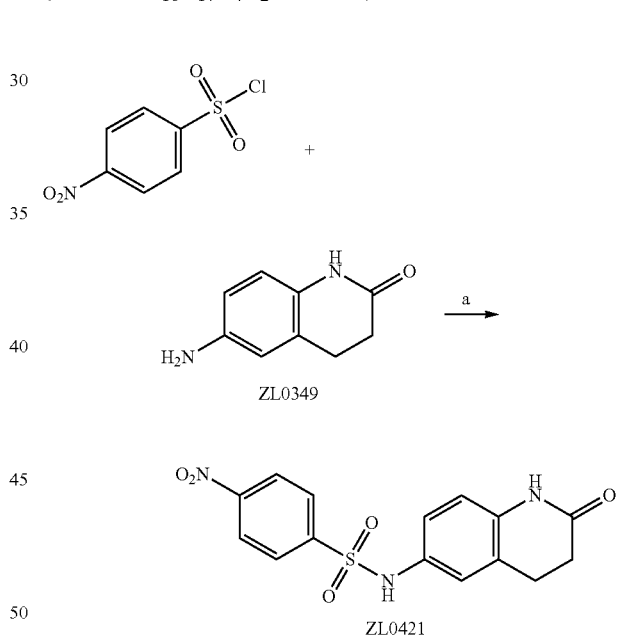

Reagents and conditions: (a) Et$_3$N, DMF, rt, 13%.

Synthesis of 4-Nitro-N-(2-oxo-1,2,3,4-tetrahydroquinolin-6-yl)benzenesulfonamide (ZL0421). Compound ZL0421 was prepared in 13% yield by a procedure similar to that used to prepare compound ZL0419. The title compound was obtained as a yellow solid. HPLC purity 98.9% ($t_R$=15.60 min). $^1$H NMR (300 MHz, DMSO-$d_6$) δ 10.02 (s, 1H), 8.36 (d, J=8.7 Hz, 2H), 7.94 (d, J=8.8 Hz, 2H), 6.89 (s, 1H), 6.79 (s, 1H), 6.69 (d, J=8.4 Hz, 1H), 2.78 (d, J=7.1 Hz, 2H), 2.37 (dd, J=8.5, 6.6 Hz, 2H). $^{13}$C NMR (75 MHz, DMSO-$d_6$) δ 170.34, 149.99, 136.06, 128.73, 124.86, 115.84, 30.60, 25.23. ESI-MS (M+H)$^+$ m/z 348.1. HR ESI-MS (M+H)$^+$ m/z=348.0646 (calcd for $C_{15}H_{14}N_3O_5$S:348.0654).

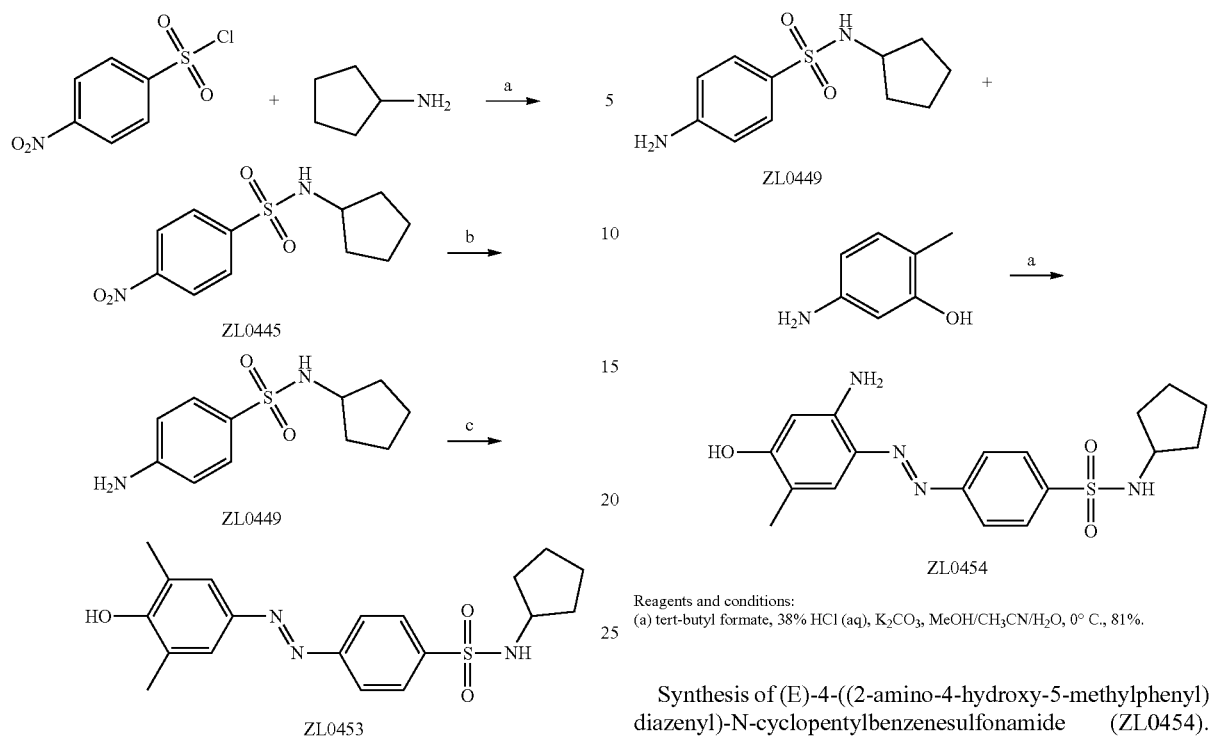

Reagents and conditions:
(a) DIPEA, DCM, 96%;
(b) Zn, NH₄Cl, EtOH/H₂O, 91%;
(c) tert-butyl formate, 38% HCl (aq), K₂CO₃, MeOH/CH₃CN/H₂O, 0° C., 82%.

Synthesis of N-cyclopentyl-4-nitrobenzenesulfonamide (ZL0445). Compound ZL0445 was prepared in 96% yield by a procedure similar to that used to prepare compound ZL0386. The title compound was obtained as a yellow solid. $^1$H NMR (300 MHz, CDCl$_3$) δ 8.39 (d, J=9.0 Hz, 2H), 8.10 (d, J=9.0 Hz, 2H), 4.80 (d, J=7.4 Hz, 1H), 3.76-3.62 (m, 1H), 1.85 (dd, J=12.4, 5.5 Hz, 2H), 1.70-1.50 (m, 4H), 1.40 (dt, J=11.9, 5.3 Hz, 2H). $^{13}$C NMR (75 MHz, CDCl$_3$) δ 166.64, 146.88, 128.31, 124.39, 55.47, 33.55, 23.10.

Synthesis of 4-amino-N-cyclopentylbenzenesulfonamide (ZL0449). Compound ZL0449 was prepared in 91% yield by a procedure similar to that used to prepare compound ZL0387. The title compound was obtained as a yellow solid. $^1$H NMR (300 MHz, CDCl$_3$) δ 7.57 (d, J=8.7 Hz, 2H), 6.64 (d, J=8.7 Hz, 2H), 5.21 (d, J=7.1 Hz, 1H), 4.36 (s, 1H), 3.46 (dd, J=13.2, 6.6 Hz, 1H), 2.64 (s, 2H), 1.79-1.64 (m, 2H), 1.56 (dd, J=7.0, 3.6 Hz, 2H), 1.38 (ddd, J=19.6, 9.5, 5.3 Hz, 4H). $^{13}$C NMR (75 MHz, CDCl$_3$) δ 150.80, 129.05, 128.29, 128.24, 114.02, 54.84, 33.24, 33.20, 23.14.

Synthesis of (E)-N-cyclopentyl-4-((4-hydroxy-3,5-dimethylphenyl)diazenyl) benzenesulfonamide (ZL0453). Compound ZL0453 was prepared in 82% yield by a procedure similar to that used to prepare compound ZL0404. The title compound was obtained as a red solid. HPLC purity 98.8% (t$_R$=20.44 min). $^1$H NMR (300 MHz, MeOD) δ 7.97 (q, J=8.2 Hz, 4H), 7.63 (s, 2H), 3.65-3.51 (m, 1H), 2.31 (s, 6H), 1.82-1.60 (m, 4H), 1.54-1.31 (m, 4H). $^{13}$C NMR (75 MHz, MeOD) δ 157.74, 154.91, 145.77, 142.12, 127.74, 124.75, 123.84, 122.30, 54.85, 32.66, 22.82, 15.38. ESI-MS (M+H)$^+$ m/z 374.1. HR ESI-MS (M+H)$^+$ m/z=374.1530 (calcd for C$_{19}$H$_{24}$N$_3$O$_3$S:374.1538)

Reagents and conditions:
(a) tert-butyl formate, 38% HCl (aq), K₂CO₃, MeOH/CH₃CN/H₂O, 0° C., 81%.

Synthesis of (E)-4-((2-amino-4-hydroxy-5-methylphenyl)diazenyl)-N-cyclopentylbenzenesulfonamide (ZL0454). Compound ZL0454 was prepared in 81% yield by a procedure similar to that used to prepare compound ZL0404. The title compound was obtained as a red solid. HPLC purity 98.1% (t$_R$=18.38 min). $^1$H NMR (300 MHz, DMSO) δ 8.03 (d, J=7.2 Hz, 2H), 7.85 (d, J=8.7 Hz, 2H), 7.68 (d, J=6.6 Hz, 1H), 6.42 (d, J=6.3 Hz, 1H), 3.42 (d, J=6.1 Hz, 1H), 2.05 (s, 3H), 1.65-1.48 (m, 4H), 1.44-1.24 (m, 4H). $^{13}$C NMR (75 MHz, DMSO-d$_6$) δ 166.55, 139.65, 130.75, 128.27, 119.99, 100.15, 54.95, 32.90, 23.27, 16.10. MS (M+H)$^+$ m/z 375.1. HR ESI-MS (M+H)$^+$ m/z=375.1530 (calcd for C18H$_{23}$N$_4$O$_3$S:375.1538)

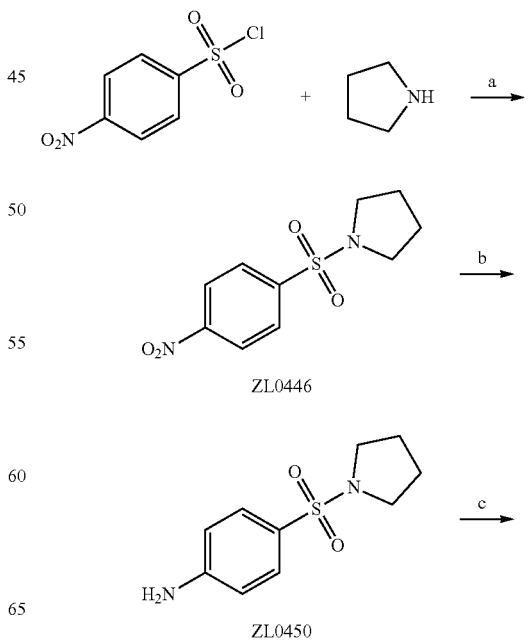

-continued

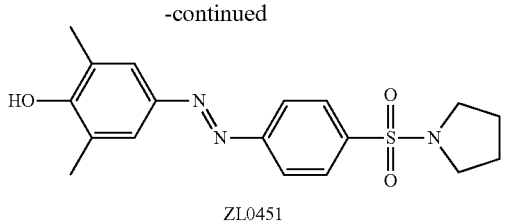

ZL0451

Reagents and conditions:
(a) DIPEA, DCM, quant;
(b) Zn, NH₄Cl, EtOH/H₂O, 68%;
(c) tert-butyl formate, 38% HCl (aq), K₂CO₃, MeOH/CH₃CN/H₂O, 0° C., 90%.

Synthesis of 1-((4-Nitrophenyl)sulfonyl)pyrrolidine (ZL0446). Compound ZL0446 was prepared in quant. yield by a procedure similar to that used to prepare compound ZL0386. The title compound was obtained as a yellow solid. $^1$H NMR (300 MHz, CDCl$_3$) δ 8.39 (d, J=8.6 Hz, 2H), 8.03 (d, J=8.6 Hz, 2H), 3.30 (t, J=6.7 Hz, 4H), 1.86-1.78 (m, 4H). $^{13}$C NMR (75 MHz, CDCl$_3$) δ 150.05, 143.12, 128.52, 124.33, 48.05, 25.38.

Synthesis of 4-(Pyrrolidin-1-ylsulfonyl)aniline (ZL0450). Compound ZL0450 was prepared in 68% yield by a procedure similar to that used to prepare compound ZL0387. The title compound was obtained as a yellow solid. $^1$H NMR (300 MHz, CDCl$_3$) δ 7.71-7.45 (m, 2H), 6.86-6.61 (m, 2H), 3.52 (d, J=5.6 Hz, 2H), 3.32-3.06 (m, 4H), 1.76 (d, J=1.7 Hz, 4H). $^{13}$C NMR (75 MHz, CDCl$_3$) δ 155.23, 133.43, 127.72, 117.81, 51.80, 28.96.

Synthesis of (E)-2,6-dimethyl-4-((4-(pyrrolidin-1-ylsulfonyl)phenyl)diazenyl)phenol (ZL0451). Compound ZL0451 was prepared in 90% yield by a procedure similar to that used to prepare compound ZL0404. The title compound was obtained as a red solid. HPLC purity 98.0% (t$_R$=20.33 min). $^1$H NMR (300 MHz, MeOD) δ 7.99 (s, 4H), 7.65 (s, 2H), 3.31-3.24 (m, 4H), 2.32 (s, 6H), 1.78 (t, J=6.6 Hz, 4H). $^{13}$C NMR (75 MHz, MeOD) δ 157.85, 155.25, 145.81, 137.22, 128.36, 124.79, 123.88, 122.39, 47.78, 24.85, 15.35. MS (M+H)⁺ m/z 360.1. HR ESI-MS (M+H)⁺ m/z=360.1373 (calcd for C$_{18}$H$_{22}$N$_3$O$_3$S:360.1382)

Synthesis of (E)-5-Amino-2-methyl-4-((4-(pyrrolidin-1-ylsulfonyl)phenyl)diazenyl) phenol (ZL0452). Compound ZL0452 was prepared in 92% yield by a procedure similar to that used to prepare compound ZL0404. The title compound was obtained as a black solid. HPLC purity 94.1% (t$_R$=18.08 min). $^1$H NMR (300 MHz, DMSO-d$_6$) δ 8.05 (d, J=8.5 Hz, 2H), 7.84 (d, J=8.7 Hz, 2H), 7.75 (t, J=12.8 Hz, 1H), 6.38 (s, 1H), 3.16 (t, J=6.6 Hz, 4H), 2.04 (s, 3H), 1.65 (dd, J=8.1, 5.1 Hz, 4H). $^{13}$C NMR (75 MHz, DMSO-d$_6$) δ 166.60, 134.11, 131.06, 129.04, 120.43, 100.11, 48.31, 25.18, 16.02. MS (M+H)⁺ m/z 361.1. HR ESI-MS (M+H)⁺ m/z=361.1328 (calcd for C$_{17}$H$_{21}$N$_4$O$_3$S:361.1334).

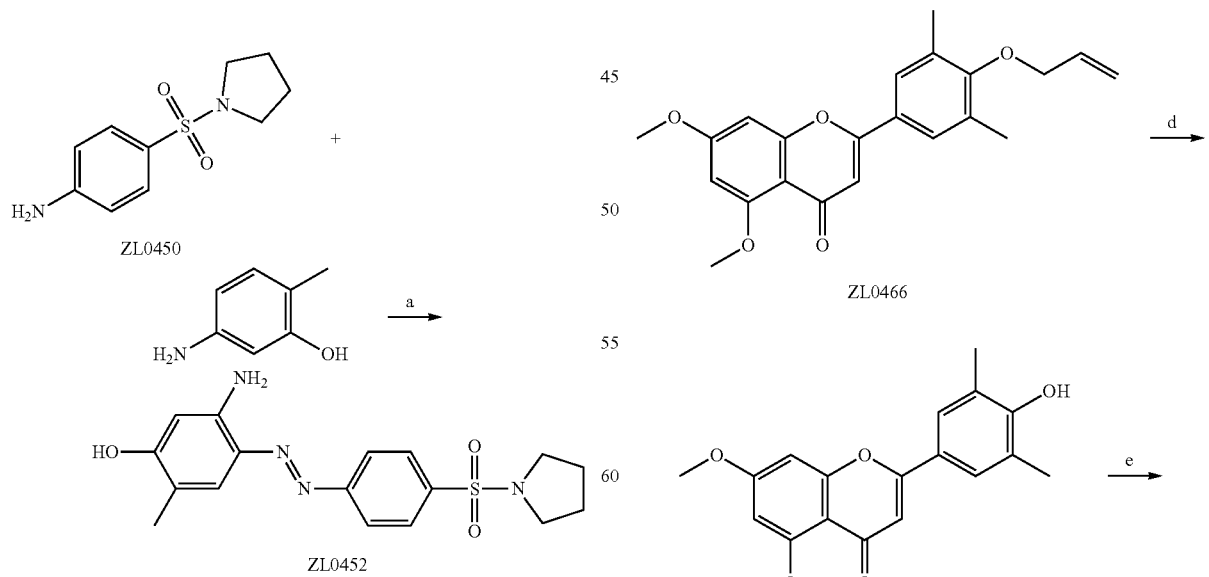

Reagents and conditions:
(a) tert-butyl formate, 38% HCl (aq), K₂CO₃, MeOH/CH₃CN/H₂O, 0° C., 92%.

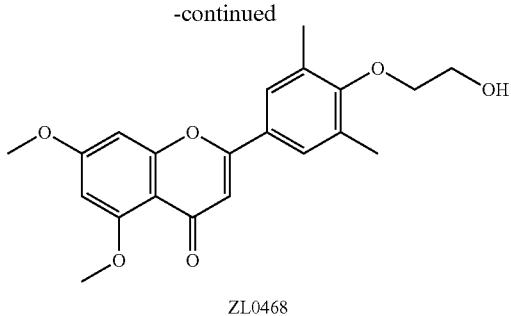

ZL0468

Reagents and conditions:
(a) 3-bromoprop-1-ene, K$_2$CO$_3$, acetone, 70° C., quant;
(b) 1-(2-hydroxy-4,6-dimethoxyphenyl)ethan-1-one, 50% KOH, EtOH, rt;
(c) I$_2$, DMSO, 140° C., 36%;
(d) Pd(PPh$_3$)$_4$, K$_2$CO$_3$, CH$_3$OH, 90° C., 75%;
(e) 2-bromoethan-1-ol, K$_2$CO$_3$, DMF, 80° C., 55%.

Synthesis of 4-(Allyloxy)-3,5-dimethylbenzaldehyde (ZL0463). To a solution of 4-hydroxy-3,5-dimethylbenzaldehyde (1.5 g, 10 mmol) and K$_2$CO$_3$ (2.07 g, 15 mmol) in 40 mL acetone, 3-bromoprop-1-ene (1.21 g, 10 mmol) was added. After stirring at 70° C. for 5 h, the mixture was poured into H$_2$O and extracted by EA. The organic extract was washed with saturated NaHCO$_3$ (aq), brine and dried over anhydrous Na$_2$SO$_4$. The resulting solution was evaporated, and the residue was put into next step directly.

Synthesis of (E)-3-(4-(Allyloxy)-3,5-dimethylphenyl)-1-(2-hydroxy-4,6-dimethoxyphenyl)prop-2-en-1-one (ZL0464). To a solution of ZL0463 (1406 mg 7.4 mmol) and 1-(2-hydroxy-4,6-dimethoxyphenyl)ethan-1-one (1450 mg, 7.4 mmol) in 20 mL EtOH, 50% KOH (829 mg, 14.8 mmol) was added. After stirring at rt overnight, the mixture was concentrated and extracted with DCM. The organic extract was washed with saturated NaHCO$_3$ (aq), brine and dried over anhydrous Na$_2$SO$_4$. The resulting solution was evaporated, and the residue was put into next step directly.

Synthesis of 2-(4-(Allyloxy)-3,5-dimethylphenyl)-5,7-dimethoxy-4H-chromen-4-one (ZL0466). To a solution of ZL0464 (1.5 g, 5 mmol) in 10 mL DMSO, I$_2$ (130 mg, 0.5 mmol) was added. After stirring at 140° C. for 4 h, the mixture was poured into H$_2$O and extracted with DCM. The organic extract was washed with saturated NaHCO$_3$ (aq), brine and dried over anhydrous Na$_2$SO$_4$. The resulting solution was evaporated, and the residue was purified by silica gel column (DCM/CH$_3$OH=50:1) to give the desired product (650 mg, 36%) as a brown foam. HPLC purity 93.4% ($t_R$=21.53 min). $^1$H NMR (300 MHz, CDCl$_3$) δ 7.50 (s, 2H), 6.57 (s, 1H), 6.55 (d, J=2.3 Hz, 1H), 6.34 (d, J=2.2 Hz, 1H), 6.19-6.02 (m, 1H), 5.44 (dd, J=17.2, 1.5 Hz, 1H), 5.28 (dd, J=10.4, 1.2 Hz, 1H), 4.35 (d, J=5.6 Hz, 2H), 3.91 (d, J=9.8 Hz, 6H), 2.34 (s, 6H). $^{13}$C NMR (75 MHz, CDCl$_3$) δ 177.58, 163.94, 160.84, 160.66, 159.86, 158.60, 133.62, 131.81, 126.77, 126.58, 117.61, 109.17, 108.37, 96.09, 92.79, 73.23, 56.34, 55.74, 16.62. MS (M+H)$^+$ m/z 367.2. HR ESI-MS (M+H)$^+$ m/z=367.1548 (calcd for C$_{22}$H$_{23}$O$_5$: 367.1545).

Synthesis of 2-(4-Hydroxy-3,5-dimethylphenyl)-5,7-dimethoxy-4H-chromen-4-one (ZL0467). To a solution of ZL0466 (630 mg, 1.72 mmol) in 10 mL CH$_3$OH, Pd(PPh$_3$)$_4$ (60 mg, 0.05 mmol) and K$_2$CO$_3$ (949 mg, 6.88 mmol) were added. After stirring at 90° C. for 7 h, the mixture was poured into 1 N HCl and extracted with n-BuOH. The organic extract was concentrated and DCM was added to precipitate. The precipitate was filtered to get the desired product (420 mg, 75%) as a yellow solid. HPLC purity 97.4% ($t_R$=17.96 min). $^1$H NMR (300 MHz, DMSO-d$_6$) δ 7.64 (s, 2H), 6.86 (d, J=2.1 Hz, 1H), 6.57 (s, 1H), 6.49 (d, J=2.1 Hz, 1H), 3.90 (s, 3H), 3.82 (s, 3H), 2.25 (s, 6H). $^{13}$C NMR (75 MHz, DMSO-d$_6$) δ 176.15, 164.03, 160.88, 160.64, 159.64, 157.11, 126.70, 125.34, 121.63, 108.74, 106.59, 96.70, 93.80, 56.55, 49.01, 17.16. MS (M+H)$^+$ m/z 327.1. HR ESI-MS (M+H)$^+$ m/z=327.1234 (calcd for C$_{19}$H$_{19}$O$_5$:327.1232)

Synthesis of 2-(4-(2-Hydroxyethoxy)-3,5-dimethylphenyl)-5,7-dimethoxy-4H-chromen-4-one (ZL0468). Compound ZL0468 was prepared in 55% yield by a procedure similar to that used to prepare compound ZL0458. The title compound was obtained as a white solid. $^1$H NMR (300 MHz, MeOD) δ 7.54 (s, 2H), 6.67 (d, J=2.3 Hz, 1H), 6.51 (s, 1H), 6.43 (d, J=2.2 Hz, 1H), 3.92 (d, J=2.2 Hz, 7H), 3.88 (s, 3H), 2.35 (s, 6H). MS (M+H)$^+$ m/z 371.1. HR ESI-MS (M+H)$^+$ m/z=371.1483 (calcd for C$_{21}$H$_{23}$O$_6$:371.1495)

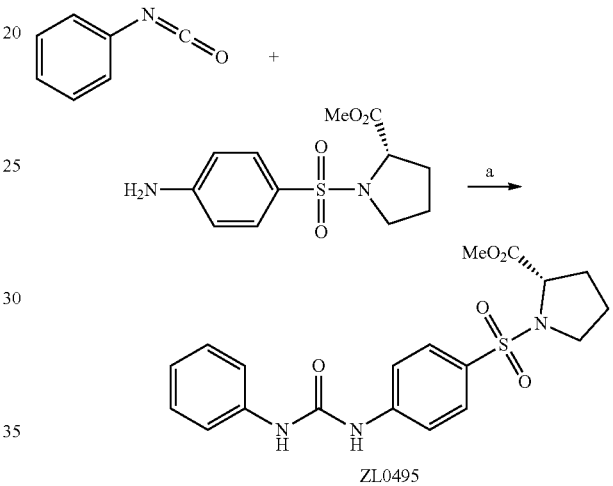

ZL0495

Reagents and conditions: (a) DCM

Synthesis of Methyl ((4-(3-phenylureido)phenyl)sulfonyl)-L-prolinate (ZL0495). Isocyanatobenzene (25 mg, 0.21 mmol) and methyl ((4-aminophenyl)sulfonyl)-L-prolinate (50 mg, 0.176 mmol) were mixed together and stirred at rt for overnight. Then the solution was concentrated and purified by silica gel column (DCM:CH$_3$OH=100:1 to 50:1) to give ZL0495 (70 mg, 99%) as a colorless oil. $^1$H NMR (300 MHz, CDCl$_3$) δ 8.01 (s, 1H), 7.78-7.68 (m, 3H), 7.55 (d, J=8.8 Hz, 2H), 7.40 (d, J=7.8 Hz, 2H), 7.28 (d, J=2.8 Hz, 2H), 7.05 (t, J=7.3 Hz, 1H), 4.24 (t, J=6.3 Hz, 1H), 3.71 (s, 3H), 3.55-3.43 (m, 1H), 3.22 (dd, J=11.9, 4.8 Hz, 1H), 2.02-1.92 (m, 3H), 1.78-1.67 (m, 1H). $^{13}$C NMR (75 MHz, CDCl$_3$) δ 172.94, 152.95, 143.99, 138.03, 130.03, 129.07, 128.63, 123.90, 120.34, 118.81, 60.63, 52.62, 48.67, 30.89, 24.64.

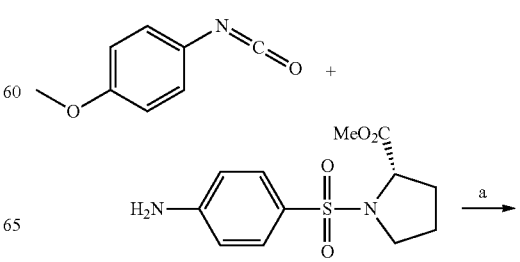

-continued

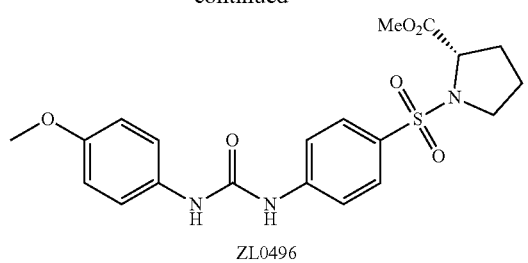

ZL0496

Reagents and conditions: (a) DCM

Synthesis of Methyl ((4-(3-(4-methoxyphenyl)ureido) phenyl)sulfonyl)-L-prolinate (ZL0496). 1-Isocyanato-4-methoxybenzene (32 mg, 0.21 mmol) and methyl ((4-aminophenyl)sulfonyl)-L-prolinate (50 mg, 0.176 mmol) were mixed together and stirred at rt for overnight. Then the solution was concentrated and purified by silica gel column (DCM:CH$_3$OH=100:1 to 50:1) to give ZL0496 (98 mg, quant.) as a yellow oil. $^1$H NMR (300 MHz, CDCl$_3$) δ 8.00 (s, 1H), 7.69 (d, J=8.8 Hz, 2H), 7.62 (s, 1H), 7.50 (d, J=8.8 Hz, 2H), 7.24 (d, J=8.9 Hz, 2H), 6.79 (d, J=9.0 Hz, 2H), 4.23 (dd, J=7.2, 5.3 Hz, 1H), 3.71 (d, J=6.1 Hz, 6H), 3.53-3.41 (m, 1H), 3.27-3.15 (m, 1H), 1.98 (tt, J=17.2, 6.4 Hz, 3H), 1.73 (dd, J=11.8, 6.7 Hz, 1H). $^{13}$C NMR (75 MHz, CDCl$_3$) δ 172.92, 156.61, 153.58, 143.97, 130.53, 130.07, 128.62, 123.12, 118.70, 114.31, 60.59, 55.45, 52.58, 48.65, 30.88, 24.63.

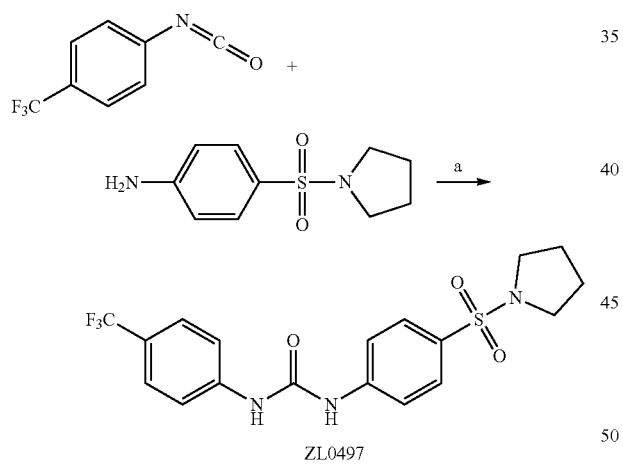

ZL0497

Reagents and conditions: (a) DCM

Synthesis of 1-(4-(Pyrrolidin-1-ylsulfonyl)phenyl)-3-(4-(trifluoromethyl)phenyl)urea (ZL0497). 1-Isocyanato-4-(trifluoromethyl)benzene (50 mg, 0.265 mmol) and 4-(pyrrolidin-1-ylsulfonyl)aniline (50 mg, 0.22 mmol) were mixed together and stirred at rt for overnight. Then the solution was concentrated and purified by silica gel column (DCM:CH$_3$OH=100:1 to 50:1) to give ZL0497 (35 mg, 34%) as a white solid. $^1$H NMR (300 MHz, MeOD) δ 7.69 (ddd, J=29.7, 21.9, 8.9 Hz, 8H), 3.28-3.20 (m, 4H), 1.81-1.72 (m, 4H). $^{13}$C NMR (75 MHz, MeOD) δ 152.75, 143.65, 142.52, 129.68, 128.50, 125.75, 125.70, 124.78, 124.35, 123.92, 123.49, 118.35, 118.17, 47.74, 24.80.

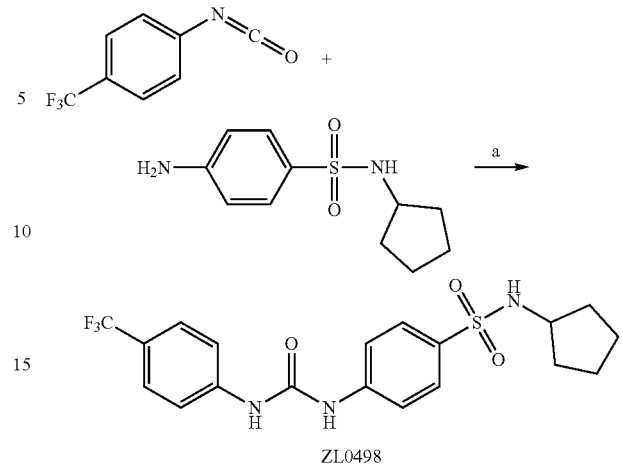

ZL0498

Reagents and conditions: (a) DCM

Synthesis of N-Cyclopentyl-4-(3-(4-(trifluoromethyl) phenyl)ureido) benzenesulfonamide (ZL0498). 1-Isocyanato-4-(trifluoromethyl)benzene (47 mg, 0.25 mmol) and 4-amino-N-cyclopentylbenzenesulfonamide (50 mg, 0.21 mmol) were mixed together and stirred at rt for overnight. Then the solution was concentrated and purified by silica gel column (DCM:CH$_3$OH=100:1 to 50:1) to give ZL0498 (69 mg, 77%) as a white solid. $^1$H NMR (300 MHz, DMSO-d$_6$) δ 9.24 (d, J=2.4 Hz, 2H), 7.72 (t, J=5.5 Hz, 2H), 7.66 (dd, J=6.8, 5.4 Hz, 6H), 7.48 (d, J=7.1 Hz, 1H), 3.42-3.36 (m, 1H), 1.56 (ddd, J=12.7, 11.2, 6.4 Hz, 4H), 1.43-1.23 (m, 4H). $^{13}$C NMR (75 MHz, DMSO-d$_6$) δ 152.53, 143.55, 143.30, 134.81, 128.24, 126.56, 118.59, 118.35, 54.86, 32.91, 23.28.

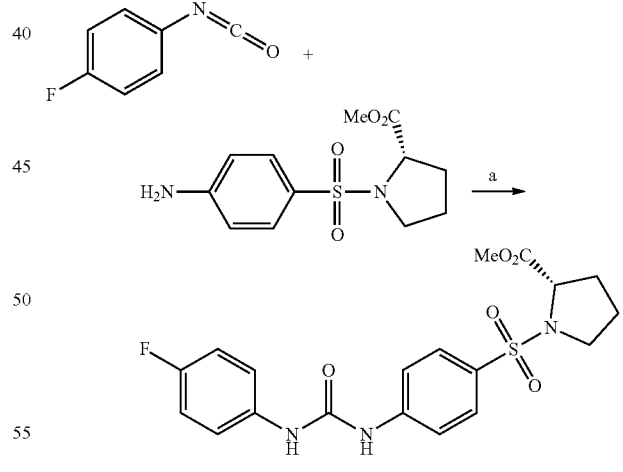

ZL0505

Reagents and conditions: (a) DCM

Synthesis of Methyl ((4-(3-(4-fluorophenyl)ureido)phenyl)sulfonyl)-L-prolinate (ZL0505). 1-Fluoro-4-isocyanatobenzene (29 mg, 0.21 mmol) and methyl ((4-aminophenyl)sulfonyl)-L-prolinate (50 mg, 0.176 mmol) were mixed together and stirred at rt for overnight. Then the solution was concentrated and purified by silica gel column (DCM:CH$_3$OH=100:1 to 50:1) to give ZL0505 (97 mg, quant.) as a yellow oil. ¹H NMR (300 MHz, CDCl₃) δ 8.04 (s, 1H), 7.78 (s, 1H), 7.72 (d, J=8.8 Hz, 2H), 7.55 (d, J=8.8 Hz, 2H), 7.38-7.30 (m, 2H), 6.95 (t, J=8.6 Hz, 2H), 4.24 (dd, J=7.4, 5.2 Hz, 1H), 3.70 (s, 3H), 3.48 (dt, J=9.4, 5.9 Hz, 1H), 3.28-3.15 (m, 1H), 1.99 (qd, J=13.0, 7.7 Hz, 3H), 1.79-1.66 (m, 1H). ¹³C NMR (75 MHz, CDCl₃) δ 173.02, 166.63, 160.82, 157.60, 153.09, 144.05, 134.02, 129.86, 128.63, 122.27, 122.16, 118.82, 115.77, 115.47, 60.65, 52.66, 48.72, 30.90, 24.64.

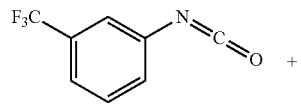

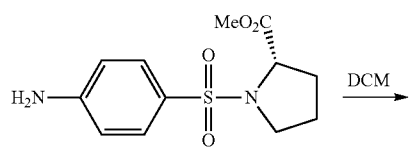

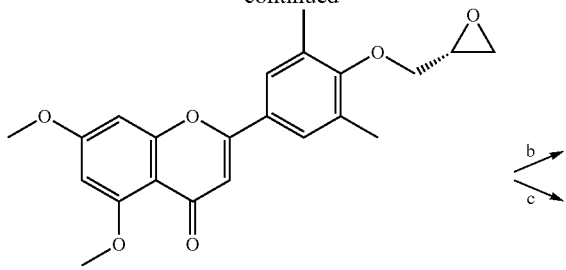

ZL0508

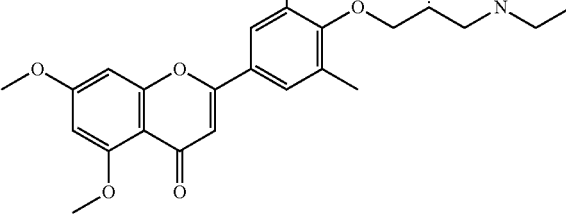

ZL0513

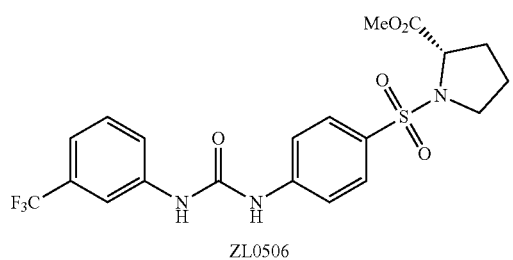

ZL0506

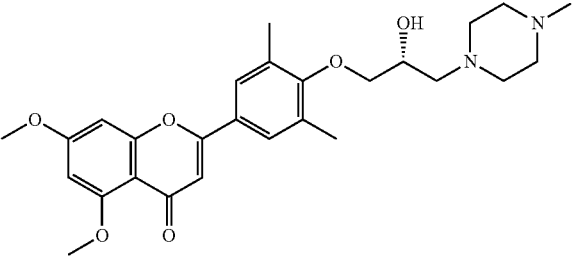

ZL0516

Reagents and conditions: (a) (R)-(-)-Epichlorohydrin, K₂CO₃, acetone, reflux, 24 hrs; (b) piperidine, K₂CO₃, EtOH/DMF, reflux, overnight, 18% for two steps; (c) 1-methylpiperazine, K₂CO₃, DMF, reflux, overnight, 20% for two steps.

Synthesis of Methyl ((4-(3-(3-(trifluoromethyl)phenyl)ureido)phenyl)sulfonyl)-L-prolinate (ZL0506). 1-Isocyanato-3-(trifluoromethyl)benzene (39 mg, 0.21 mmol) and methyl ((4-aminophenyl)sulfonyl)-L-prolinate (50 mg, 0.176 mmol) were mixed together and stirred at rt for overnight. Then the solution was concentrated and purified by PTLC (DCM:CH₃OH=50:1) to give ZL0506 (101 mg, quant.) as a yellow oil. ¹H NMR (300 MHz, CDCl₃) δ 8.11 (s, 1H), 8.01 (s, 1H), 7.75 (d, J=8.9 Hz, 3H), 7.63 (d, J=8.9 Hz, 3H), 7.38 (t, J=7.9 Hz, 1H), 7.27 (d, J=6.5 Hz, 1H), 4.25 (dd, J=7.4, 5.4 Hz, 1H), 3.71 (s, 3H), 3.50 (dt, J=9.6, 6.1 Hz, 1H), 3.29-3.17 (m, 1H), 2.10-1.89 (m, 3H), 1.80-1.66 (m, 1H). ¹³C NMR (75 MHz, CDCl₃) δ 173.09, 152.56, 143.99, 138.96, 131.01, 129.83, 129.49, 128.62, 122.80, 118.98, 116.32, 60.72, 52.71, 48.75, 30.89, 24.62.

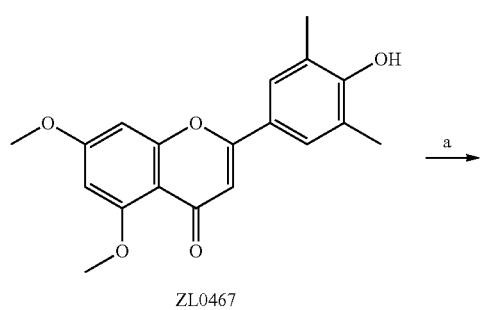

ZL0467

Synthesis of (R)-2-(3,5-dimethyl-4-(oxiran-2-ylmethoxy)phenyl)-5,7-dimethoxy-4H-chromen-4-one (ZL0508). To a solution of ZL0467 (100 mg, 0.31 mmol) in 5 mL acetone, (R)-(-)-Epichlorohydrin (285 mg, 3.1 mmol) and K₂CO₃ (211 mg, 1.53 mmol) were added. The mixture was refluxed for 24 hours and then poured into H₂O. The solution was extracted with DCM (20 mL×3). The organic layer was washed with saturated NaHCO₃ (aq), brine and dried over anhydrous Na₂SO₄. The resulting solution was filtered and concentrated to give a crude solid. The crude product was put into next step directly.

Synthesis of (R)-2-(4-(2-hydroxy-3-(piperidin-1-yl)propoxy)-3,5-dimethylphenyl)-5,7-dimethoxy-4H-chromen-4-one (ZL0513). To a solution of ZL0508 (48 mg, 0.164 mmol) in 2 mL EtOH and 2 mL DMF, piperidine (139 mg, 1.64 mmol) and K₂CO₃ (226 mg, 1.64 mmol) were added. The mixture was refluxed for 24 hours and then poured into H₂O. The solution was extracted with DCM (20 mL×3). The organic layer was washed with saturated NaHCO₃ (aq), brine and dried over anhydrous Na₂SO₄. The resulting solution was filtered and concentrated to give a crude solid. The crude product was purified by PTLC (DCM:CH₃OH=20:1) to give ZL0513 (13 mg, 18% for two steps) as a white solid. ¹H NMR (300 MHz, MeOD) δ 7.50 (s, 2H), 6.63 (s, 1H), 6.44 (d, J=21.6 Hz, 2H), 4.00-3.77 (m, 9H), 2.73 (s, 6H), 2.32 (s, 6H), 1.63 (d, J=43.9 Hz, 6H). ¹³C NMR (75 MHz, MeOD) δ 178.43, 164.90, 161.54, 160.51, 159.75, 158.51, 131.69, 126.46, 126.15, 107.81, 106.60, 95.94, 92.71, 74.39, 66.94, 61.00, 55.15, 54.56, 24.82, 23.31, 15.30.

Synthesis of (R)-2-(4-(2-hydroxy-3-(4-methylpiperazin-1-yl)propoxy)-3,5-dimethylphenyl)-5,7-dimethoxy-4H-chromen-4-one (ZL0516). To a solution of ZL0508 (48 mg, 0.164 mmol) in 5 mL DMF, 1-methylpiperazine (164 mg, 1.64 mmol) and K$_2$CO$_3$ (226 mg, 1.64 mmol) were added. The mixture was refluxed for 24 hours and then poured into H$_2$O. The solution was extracted with DCM (20 mL×3). The organic layer was washed with saturated NaHCO$_3$ (aq), brine and dried over anhydrous Na$_2$SO$_4$. The resulting solution was filtered and concentrated to give a crude solid. The crude product was purified by PTLC (DCM:CH$_3$OH=20:1) to give ZL0516 (16 mg, 20% for two steps) as a white solid. $^1$H NMR (300 MHz, CDCl$_3$) δ 7.45 (s, 2H), 6.49 (d, J=6.4 Hz, 2H), 6.29 (s, 1H), 4.02 (s, 1H), 3.82 (s, 8H), 2.49 (dd, J=39.7, 24.1 Hz, 10H), 2.25 (d, J=6.1 Hz, 9H). $^{13}$C NMR (75 MHz, CDCl$_3$) δ 182.49, 168.36, 165.44, 164.67, 163.88, 162.29, 135.69, 130.78, 112.62, 111.68, 100.18, 96.80, 78.13, 70.60, 64.26, 59.94, 59.68, 58.62, 56.59, 49.31, 20.23.

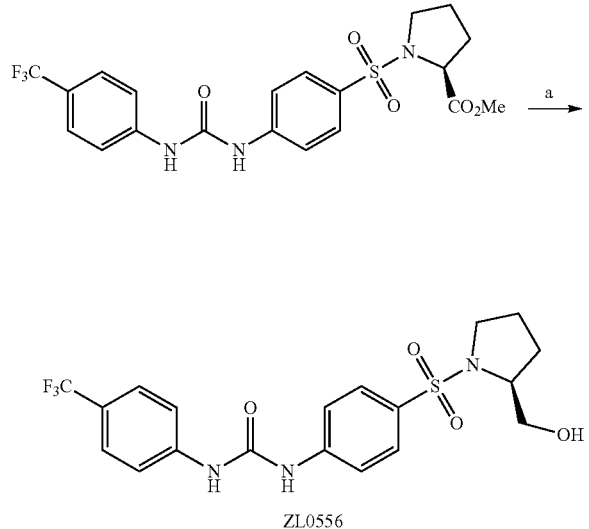

ZL0556

Reagents and conditions: (a) LiAlH$_4$, THF, 0° C., 30 min, quant.

Synthesis of (S)-1-(4-((2-(Hydroxymethyl)pyrrolidin-1-yl)sulfonyl)phenyl)-3-(4-(trifluoromethyl)phenyl)urea (ZL0556). To a solution of ZL0392 (50 mg, 0.1 mmol) in 4 mL THF, LiAlH$_4$ (11 mg, 0.3 mmol) was added under N$_2$. After 30 min, the mixture was poured into H$_2$O, and extracted with DCM. After drying over anhydrous Na$_2$SO$_4$, the solution was concentrated and purified with silica gel column (DCM/CH$_3$OH=20/1) to obtain the desired product (46 mg, quant.) as an white solid. $^1$H NMR (300 MHz, CDCl$_3$) δ 7.86 (s, 1H), 7.80 (s, 1H), 7.74 (s, 1H), 7.72 (s, 1H), 7.57 (s, 1H), 7.55 (s, 4H), 3.70 (d, J=3.3 Hz, 3H), 3.47 (dt, J=12.0, 6.2 Hz, 1H), 3.36-3.16 (m, 2H), 1.90-1.77 (m, 1H), 1.74 (s, 1H), 1.62-1.48 (m, 1H). $^{13}$C NMR (75 MHz, CDCl$_3$) δ 152.06, 143.60, 141.32, 129.75, 128.82, 126.41, 126.37, 126.27, 119.13, 118.99, 65.68, 61.90, 50.12, 28.74, 24.23.

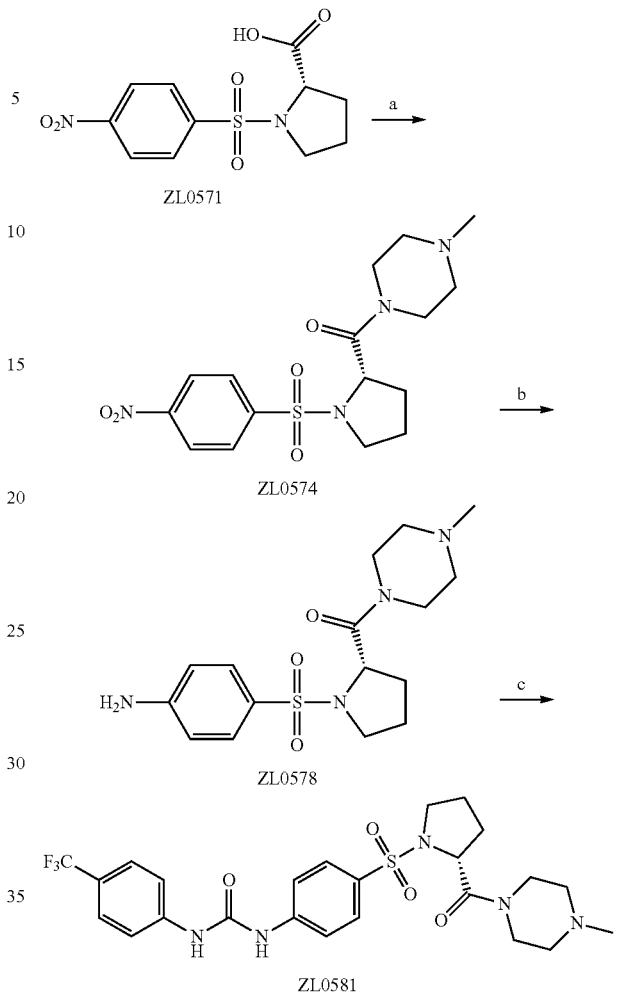

Reagents and conditions: (a) 1-methylpiperazine, HBTU, DIEA, DCM, rt, 84%; (b) Zn, NH$_4$Cl, EtOH/H$_2$O, reflux; (c) 1-isocyanato-4-(trifluoromethyl)benzene, DCM, rt, 60% for two steps.

Synthesis of (S)-1-Methyl-4-(((4-nitrophenyl)sulfonyl)prolyl)piperazine (ZL0574). ZL0574 (106 mg, 84 mg) was obtained as a yellow solid followed the procedure of ZL0573. $^1$H NMR (300 MHz, CDCl$_3$) δ 8.25 (d, J=8.5 Hz, 2H), 8.00 (d, J=8.5 Hz, 2H), 4.84 (dd, J=8.1, 3.2 Hz, 1H), 3.47 (dd, J=18.7, 10.5 Hz, 5H), 3.32 (dd, J=13.8, 8.0 Hz, 1H), 2.46-2.26 (m, 4H), 2.19-2.08 (m, 1H), 2.04-1.79 (m, 3H). $^{13}$C NMR (75 MHz, CDCl$_3$) δ 169.10, 149.80, 145.16, 128.72, 123.88, 58.54, 54.94, 54.59, 48.13, 45.91, 45.45, 42.06, 30.91, 24.76.

Synthesis of (S)-1-(((4-Aminophenyl)sulfonyl)prolyl)-4-methylpiperazine (ZL0578). ZL0578 was obtained following the procedure of ZL0576. $^1$H NMR (300 MHz, CDCl$_3$) δ 7.61 (d, J=8.5 Hz, 2H), 6.67 (d, J=8.6 Hz, 2H), 4.61 (dd, J=7.5, 4.8 Hz, 1H), 4.37 (s, 1H), 3.67 (dd, J=15.7, 10.0 Hz, 4H), 3.37 (dd, J=10.9, 6.1 Hz, 2H), 2.53 (d, J=23.4 Hz, 4H), 2.36 (s, 3H), 2.07-1.84 (m, 3H).

Synthesis of (R)-1-(4-((2-(4-Methylpiperazine-1-carbonyl)pyrrolidin-1-yl)sulfonyl) phenyl)-3-(4-(trifluoromethyl)phenyl)urea (ZL0581). ZL0581 (76 mg, 60% for two steps) was obtained following the procedure of ZL0580. $^1$H NMR (300 MHz, MeOD) δ 7.82 (d, J=8.7 Hz, 2H), 7.69 (dd, J=11.7, 8.9 Hz, 4H), 7.59 (d, J=8.5 Hz, 2H), 4.70 (dd, J=7.9, 4.7 Hz, 1H), 3.79-3.41 (m, 6H), 2.47 (d, J=20.7 Hz, 4H), 2.32 (s, 3H), 2.05 (dd, J=11.2, 7.8 Hz, 1H), 1.94 (dd, J=12.4, 6.3 Hz, 1H), 1.88-1.77 (m, 1H), 1.64 (dt, J=12.3, 6.2 Hz, 1H). $^{13}$C NMR (75 MHz, MeOD) δ 171.14, 152.63, 143.83, 142.59, 131.00, 129.35, 128.55, 125.81, 125.76, 125.71, 125.66, 118.35, 118.21, 113.12, 58.36, 54.48, 54.03, 48.50, 44.88, 44.57, 41.70, 30.59, 24.42.

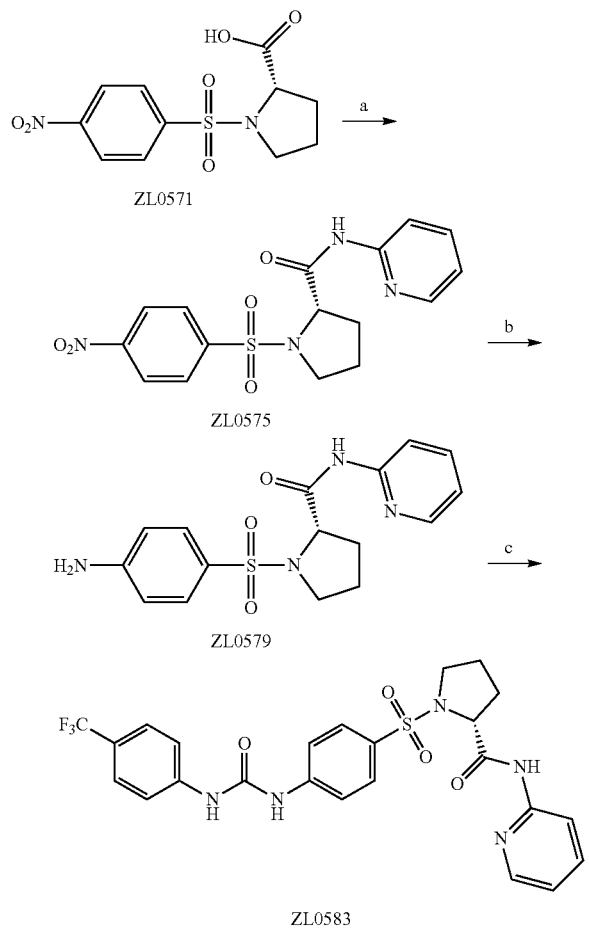

Reagents and conditions: (a) 1-methylpiperazine, HBTU, DIEA, DCM, rt, 69%; (b) Zn, NH$_4$Cl, EtOH/H$_2$O, reflux; (c) 1-isocyanato-4-(trifluoromethyl)benzene, DCM, rt, 17% for two steps.

Synthesis of (S)-1-((4-Nitrophenyl)sulfonyl)-N-(pyridin-2-yl)pyrrolidine-2-carboxamide (ZL0575). ZL0575 (85 mg, 69%) was obtained as a white foam following the procedure of ZL0573. $^1$H NMR (300 MHz, CDCl$_3$) δ 9.15 (s, 1H), 8.36 (d, J=8.4 Hz, 2H), 8.28 (d, J=4.1 Hz, 1H), 8.11 (dd, J=14.0, 8.6 Hz, 3H), 7.69 (t, J=7.6 Hz, 1H), 7.12-6.99 (m, 1H), 4.31 (d, J=4.8 Hz, 1H), 3.64 (s, 1H), 3.32 (dd, J=16.0, 7.7 Hz, 1H), 2.23 (d, J=7.9 Hz, 1H), 1.89 (t, J=18.4 Hz, 2H), 1.77 (dd, J=10.7, 4.2 Hz, 1H). $^{13}$C NMR (75 MHz, CDCl$_3$) δ 169.40, 150.72, 150.46, 148.01, 142.09, 138.40, 129.12, 124.58, 120.36, 113.98, 63.06, 49.88, 30.64, 24.58.

Synthesis of (S)-1-((4-Aminophenyl)sulfonyl)-N-(pyridin-2-yl)pyrrolidine-2-carboxamide (ZL0579). ZL0579 was obtained following the procedure of ZL0576.

Synthesis of (R)—N-(Pyridin-2-yl)-1-((4-(3-(4-(trifluoromethyl)phenyl)ureido)phenyl) sulfonyl)pyrrolidine-2-carboxamide (ZL0583). ZL0583 (20 mg, 17% for two steps) was obtained as a white solid following the procedure of ZL0580. $^1$H NMR (300 MHz, MeOD) δ 8.32 (d, J=4.2 Hz, 1H), 8.15 (d, J=8.3 Hz, 1H), 7.87 (d, J=8.8 Hz, 2H), 7.84-7.77 (m, 1H), 7.74 (d, J=8.8 Hz, 2H), 7.68 (d, J=8.7 Hz, 2H), 7.60 (d, J=8.8 Hz, 2H), 7.15 (dd, J=7.0, 5.1 Hz, 1H), 4.32 (dd, J=7.9, 4.0 Hz, 1H), 3.68-3.58 (m, 1H), 3.39-3.33 (m, 1H), 2.15-2.03 (m, 1H), 1.98-1.84 (m, 2H), 1.68 (dd, J=11.0, 5.4 Hz, 1H). $^{13}$C NMR (75 MHz, MeOD) δ 171.46, 152.61, 151.00, 147.65, 144.26, 142.53, 138.37, 129.26, 128.91, 125.79, 125.74, 125.69, 125.64, 120.03, 118.35, 118.24, 114.05, 62.70, 49.44, 30.51, 24.28.

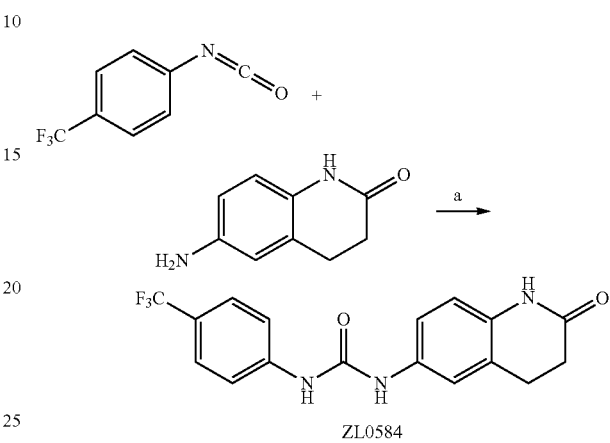

Reagents and conditions: (a) DCM, rt, 41%.

Synthesis of 1-(2-Oxo-1,2,3,4-tetrahydroquinolin-6-yl)-3-(4-(trifluoromethyl) phenyl)urea (ZL0584). ZL0584 (85 mg, 41%) was obtained as a white solid following the procedure of ZL0498. $^1$H NMR (300 MHz, DMSO-d$_6$) δ 9.98 (s, 1H), 9.01 (s, 1H), 8.61 (s, 1H), 7.63 (q, J=9.0 Hz, 4H), 7.31 (s, 1H), 7.18 (d, J=7.2 Hz, 1H), 6.79 (d, J=8.4 Hz, 1H), 2.85 (t, J=7.4 Hz, 2H), 2.42 (t, J=7.4 Hz, 2H). $^{13}$C NMR (75 MHz, DMSO-d$_6$) δ 170.36, 152.83, 144.04, 134.03, 133.79, 126.83, 126.51, 126.47, 126.42, 124.47, 123.24, 122.71, 122.28, 121.86, 121.44, 119.06, 118.21, 115.68, 30.86, 25.54.

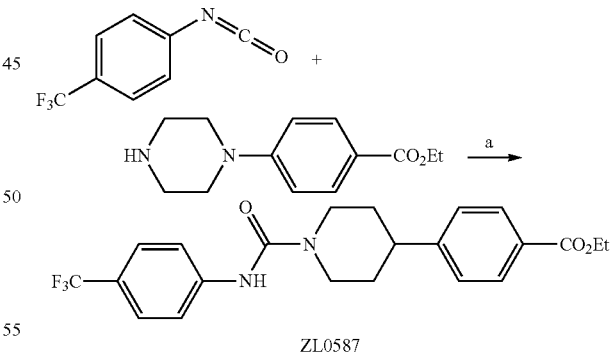

Reagents and conditions: (a) DCM, rt, 72%.

Synthesis of Ethyl 4-(1-((4-(trifluoromethyl)phenyl)carbamoyl)piperidin-4-yl)benzoate (ZL0587). ZL0587 (63 mg, 72%) was obtained as a white solid following the procedure of ZL0498. $^1$H NMR (300 MHz, DMSO-d$_6$) δ 9.01 (s, 1H), 7.81 (d, J=8.7 Hz, 2H), 7.71 (d, J=8.6 Hz, 2H), 7.59 (d, J=8.7 Hz, 2H), 7.02 (d, J=8.8 Hz, 2H), 4.24 (q, J=7.0 Hz, 2H), 3.63 (d, J=5.1 Hz, 4H), 3.39 (s, 4H), 1.29 (t, J=7.1 Hz, 3H). $^{13}$C NMR (75 MHz, DMSO-d$_6$) δ 166.13, 155.01, 154.09, 144.78, 131.14, 126.88, 126.14, 126.10, 126.05, 126.00, 123.28, 122.36, 121.94, 119.43, 119.18, 113.94, 60.36, 46.95, 43.75, 14.76.

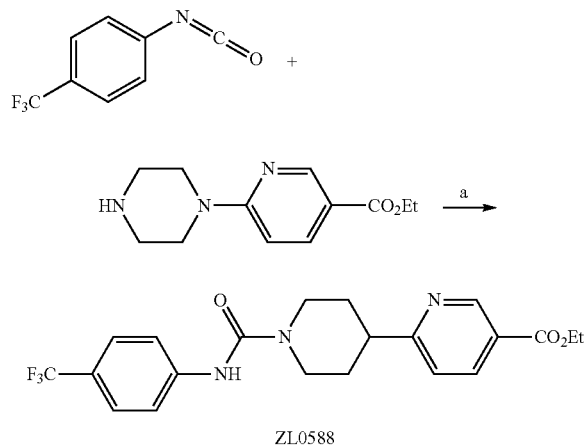

Reagents and conditions: (a) DCM, rt, quant.

Synthesis of Ethyl 6-(1-((4-(trifluoromethyl)phenyl)carbamoyl)piperidin-4-yl)nicotinate (ZL0588). ZL0588 (101 mg, quant.) was obtained as a white solid following the procedure of ZL0498. $^1$H NMR (300 MHz, DMSO-$d_6$) δ 9.01 (s, 1H), 8.67 (d, J=2.0 Hz, 1H), 7.97 (dd, J=9.0, 2.1 Hz, 1H), 7.71 (d, J=8.6 Hz, 2H), 7.59 (d, J=8.7 Hz, 2H), 6.91 (d, J=9.1 Hz, 1H), 4.26 (q, J=7.0 Hz, 2H), 3.73 (d, J=5.3 Hz, 4H), 3.61 (d, J=5.1 Hz, 4H), 1.29 (t, J=7.1 Hz, 3H). $^{13}$C NMR (75 MHz, DMSO-$d_6$) δ 165.50, 160.66, 155.02, 150.63, 144.77, 138.50, 126.04, 119.44, 114.65, 106.30, 60.53, 44.33, 43.72, 14.70.

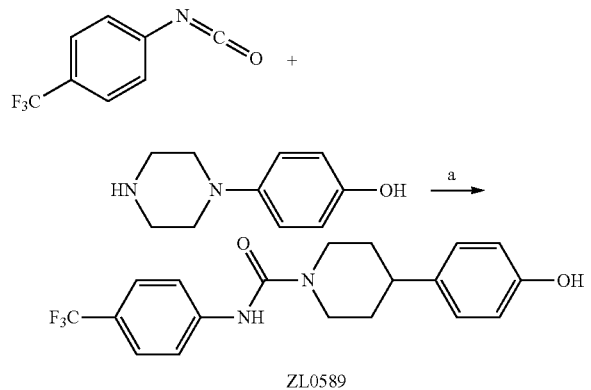

Reagents and conditions: (a) DCM, rt, 84%.

Synthesis of 4-(4-hydroxyphenyl)-N-(4-(trifluoromethyl)phenyl)piperidine-1-carboxamide (ZL0589). ZL0589 (92 mg, 84%) was obtained as a white solid following the procedure of ZL0498. $^1$H NMR (300 MHz, DMSO-$d_6$) δ 8.98 (s, 1H), 8.90 (s, 1H), 7.71 (d, J=8.5 Hz, 2H), 7.58 (d, J=8.6 Hz, 2H), 6.84 (d, J=8.7 Hz, 2H), 6.68 (d, J=8.6 Hz, 2H), 3.60 (s, 4H), 2.98 (s, 4H). $^{13}$C NMR (75 MHz, DMSO-$d_6$) δ 166.63, 154.99, 151.80, 144.85, 144.47, 126.03, 119.37, 118.87, 115.95, 50.74, 44.37.

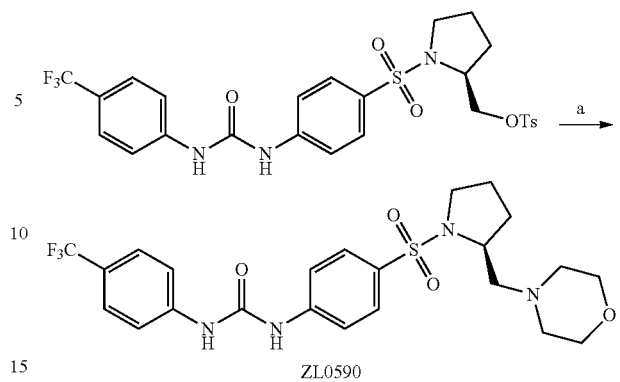

Reagents and conditions: (a) Morpholine, K$_2$CO$_3$, CH$_3$CN, 50° C., 57%.

Synthesis of (S)-1-(4-((2-(morpholinomethyl)pyrrolidin-1-yl)sulfonyl)phenyl)-3-(4-(trifluoromethyl) phenyl)urea (ZL0590). To a solution of (S)-(1-((4-(3-(4-(trifluoromethyl)phenyl)ureido)phenyl)sulfonyl)pyrrolidin-2-yl)methyl 4-methylbenzenesulfonate (50 mg, 0.1 mmol) in 5 mL CH$_3$CN, K$_2$CO$_3$ (41 mg, 0.3 mmol) was added. The mixture was allowed to stir at 50° C. for overnight. Then the mixture was poured into H$_2$O and extracted by DCM. The organic layer was washed with saturated NaHCO$_3$ (aq), brine and dried over anhydrous Na$_2$SO$_4$. The resulting solution was evaporated, and the residue was purified by PTLC (DCM/MeOH=50:1) to give the desired product (29 mg, 57%) as a white solid. $^1$H NMR (300 MHz, MeOD) δ 7.80 (d, J=8.8 Hz, 2H), 7.71 (d, J=8.5 Hz, 2H), 7.67 (d, J=8.9 Hz, 2H), 7.59 (d, J=8.7 Hz, 2H), 3.79 (d, J=4.9 Hz, 1H), 3.73-3.63 (m, 4H), 3.38 (d, J=7.6 Hz, 1H), 3.24-3.14 (m, 1H), 2.70-2.24 (m, 7H), 1.84 (d, J=5.6 Hz, 2H), 1.66-1.48 (m, 2H). $^{13}$C NMR (75 MHz, MeOD) δ 152.68, 143.72, 142.57, 130.40, 128.62, 128.52, 126.25, 125.79, 125.74, 125.69, 124.69, 124.26, 123.83, 123.40, 122.67, 118.33, 118.18, 66.51, 63.38, 57.69, 54.06, 48.76, 29.47, 23.47.

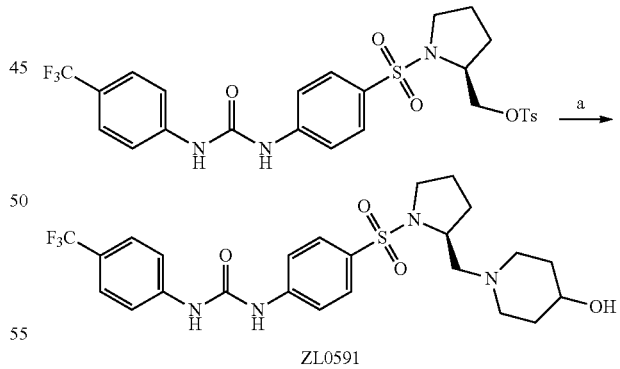

Reagents and conditions: (a) piperidin-4-ol, K$_2$CO$_3$, CH$_3$CN, 50° C., 34%.

Synthesis of (S)-1-(4-((2-((4-Hydroxypiperidin-1-yl)methyl)pyrrolidin-1-yl)sulfonyl) phenyl)-3-(4-(trifluoromethyl)phenyl)urea (ZL0491). ZL0591 (18 mg, 34%) was synthesized as a white solid following the procedure of ZL0590. $^1$H NMR (300 MHz, MeOD) δ 7.81 (d, J=8.7 Hz, 2H), 7.70 (dd, J=12.6, 8.9 Hz, 4H), 7.60 (d, J=8.7 Hz, 2H), 3.78 (s, 1H), 3.70-3.58 (m, 1H), 3.37 (d, J=4.4 Hz, 1H), 3.25-3.14 (m, 1H), 3.02-2.83 (m, 2H), 2.69 (dd, J=12.6, 3.8

Hz, 1H), 2.39 (ddd, J=38.3, 19.0, 9.8 Hz, 3H), 1.94-1.76 (m, 4H), 1.60 (dd, J=18.1, 9.0 Hz, 4H). $^{13}$C NMR (75 MHz, MeOD) δ 152.71, 143.77, 142.57, 130.31, 128.52, 126.25, 125.78, 125.73, 125.68, 125.63, 124.70, 124.27, 123.84, 123.41, 122.66, 118.33, 118.19, 66.84, 62.85, 57.99, 52.18, 51.19, 48.72, 33.50, 33.40, 29.70, 23.44.

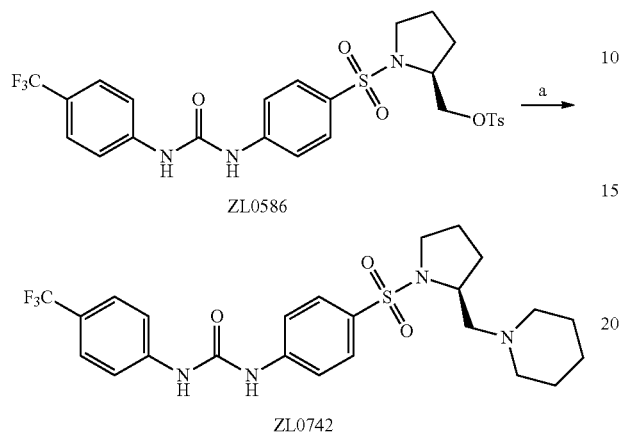

Reagents and conditions: (a) piperidine, K$_2$CO$_3$, NaI, Et$_3$N, CH$_3$CN, 75° C., 73%.

Synthesis of (S)-1-(4-((2-(morpholinomethyl)pyrrolidin-1-yl)sulfonyl)phenyl)-3-(4-(trifluoromethyl) phenyl)urea (ZL0742). To a solution of ZL0586 (58 mg, 0.1 mmol) in 5 mL CH$_3$CN, K$_2$CO$_3$ (41 mg, 0.3 mmol) and piperidine (17 mg, 0.2 mmol) were added. The mixture was allowed to stir at 50° C. for overnight. No reaction was happened. Then NaI (7.5 mg, 0.05 mmol) and two drops of Et3N were added and the mixture was allowed to reflux overnight under N$_2$. Then the mixture was poured into H$_2$O and extracted by DCM. The organic layer was washed with saturated NaHCO$_3$ (aq), brine and dried over anhydrous Na$_2$SO$_4$. The resulting solution was evaporated, and the residue was purified by PTLC (DCM/MeOH=50:1) to give the desired product (30 mg, 73%) as a yellow oil and 10 mg of ZL0586 was recovered. $^1$H NMR (300 MHz, CDCl$_3$) δ 8.90 (s, 1H), 8.73 (s, 1H), 7.66 (s, 4H), 7.60 (d, J=8.5 Hz, 2H), 7.49 (d, J=8.7 Hz, 2H), 3.75 (d, J=6.9 Hz, 1H), 3.39 (dd, J=6.5, 3.0 Hz, 1H), 3.11 (d, J=7.8 Hz, 1H), 2.54 (dtd, J=19.9, 12.7, 4.5 Hz, 6H), 1.80 (dd, J=10.5, 5.4 Hz, 2H), 1.66-1.51 (m, 6H), 1.46 (d, J=5.1 Hz, 2H). $^{13}$C NMR (75 MHz, CDCl$_3$) δ 152.50, 144.13, 141.96, 129.30, 128.59, 126.20, 126.15, 126.10, 126.05, 124.97, 124.53, 122.43, 118.75, 118.62, 63.71, 58.03, 55.48, 49.33, 29.75, 25.62, 23.88, 23.78.

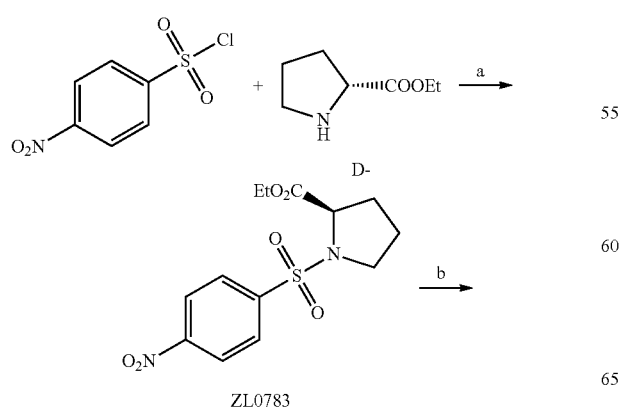

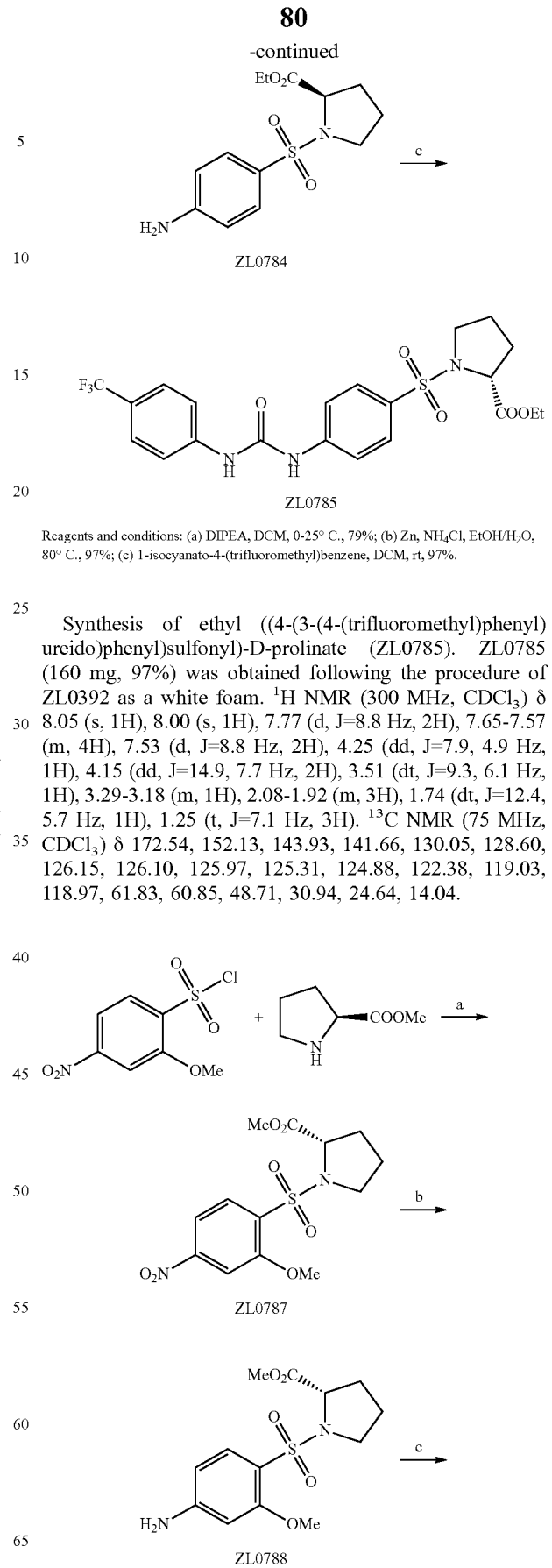

Reagents and conditions: (a) DIPEA, DCM, 0-25° C., 79%; (b) Zn, NH$_4$Cl, EtOH/H$_2$O, 80° C., 97%; (c) 1-isocyanato-4-(trifluoromethyl)benzene, DCM, rt, 97%.

Synthesis of ethyl ((4-(3-(4-(trifluoromethyl)phenyl) ureido)phenyl)sulfonyl)-D-prolinate (ZL0785). ZL0785 (160 mg, 97%) was obtained following the procedure of ZL0392 as a white foam. $^1$H NMR (300 MHz, CDCl$_3$) δ 8.05 (s, 1H), 8.00 (s, 1H), 7.77 (d, J=8.8 Hz, 2H), 7.65-7.57 (m, 4H), 7.53 (d, J=8.8 Hz, 2H), 4.25 (dd, J=7.9, 4.9 Hz, 1H), 4.15 (dd, J=14.9, 7.7 Hz, 2H), 3.51 (dt, J=9.3, 6.1 Hz, 1H), 3.29-3.18 (m, 1H), 2.08-1.92 (m, 3H), 1.74 (dt, J=12.4, 5.7 Hz, 1H), 1.25 (t, J=7.1 Hz, 3H). $^{13}$C NMR (75 MHz, CDCl$_3$) δ 172.54, 152.13, 143.93, 141.66, 130.05, 128.60, 126.15, 126.10, 125.97, 125.31, 124.88, 122.38, 119.03, 118.97, 61.83, 60.85, 48.71, 30.94, 24.64, 14.04.

-continued

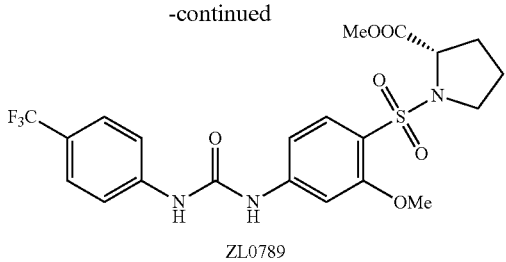

ZL0789

Reagents and conditions: (a) DIPEA, DCM, 0-25° C., 93%; (b) Zn, NH₄Cl, EtOH/H₂O, 80° C., 87%; (c) 1-isocyanato-4-(trifluoromethyl)benzene, DCM, rt, quant.

Synthesis of methyl ((2-methoxy-4-(3-(4-(trifluoromethyl)phenyl)ureido)phenyl)sulfonyl)-L-prolinate (ZL0789). ZL0789 (150 mg, quant.) was obtained following the procedure of ZL0392 as a yellow solid. $^{1}$H NMR (300 MHz, CDCl₃) δ 8.12 (s, 1H), 8.01 (s, 1H), 7.77 (t, J=5.5 Hz, 2H), 7.64 (d, J=8.6 Hz, 2H), 7.55 (d, J=8.8 Hz, 2H), 6.79 (dd, J=8.7, 1.8 Hz, 1H), 4.65 (dd, J=8.1, 4.1 Hz, 1H), 3.90 (s, 3H), 3.67 (s, 3H), 3.61-3.51 (m, 1H), 3.26-3.16 (m, 1H), 2.21-1.99 (m, 3H), 1.91-1.79 (m, 1H). $^{13}$C NMR (75 MHz, CDCl₃) δ 173.32, 157.76, 152.18, 146.24, 141.86, 132.38, 126.20, 126.16, 126.11, 126.06, 125.56, 125.13, 124.70, 124.27, 122.46, 118.96, 118.08, 110.00, 102.26, 61.26, 56.09, 52.57, 48.12, 30.78, 24.86.

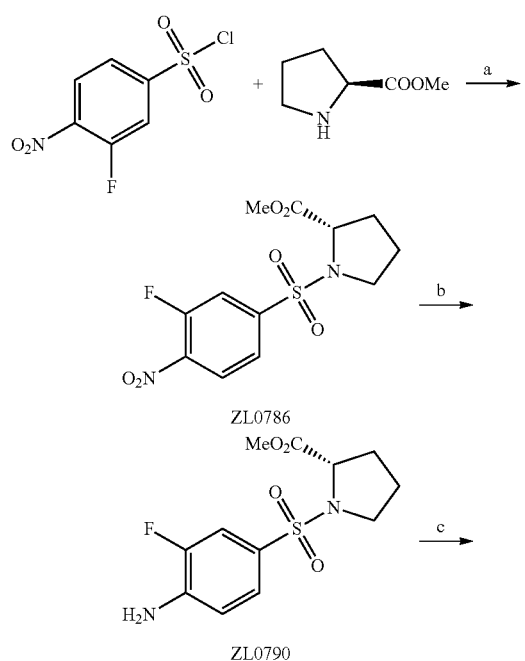

ZL0791

Reagents and conditions: (a) DIPEA, DCM, 0-25° C., 90%; (b) Zn, NH₄Cl, EtOH/H₂O, 80° C., 88%; (c) 1-isocyanato-4-(trifluoromethyl)benzene, DCM, rt, 66%.

Synthesis of methyl ((3-fluoro-4-(3-(4-(trifluoromethyl)phenyl)ureido)phenyl)sulfonyl)-L-prolinate (ZL0791). ZL0791 (96 mg, 66%) was obtained following the procedure of ZL0392 as an off-white solid. $^{1}$H NMR (300 MHz, CDCl₃) δ 8.52 (dd, J=8.7, 7.9 Hz, 1H), 8.13 (s, 1H), 7.94 (d, J=3.5 Hz, 1H), 7.64 (dd, J=9.4, 6.2 Hz, 4H), 7.55 (d, J=8.8 Hz, 2H), 4.31 (dd, J=7.8, 4.6 Hz, 1H), 3.73 (s, 3H), 3.54 (dt, J=9.2, 6.0 Hz, 1H), 3.29 (dt, J=9.1, 7.1 Hz, 1H), 2.13-1.94 (m, 3H), 1.82 (dd, J=11.6, 6.6 Hz, 1H). $^{13}$C NMR (75 MHz, CDCl₃) δ 172.79, 152.82, 151.69, 149.55, 141.37, 132.51, 132.38, 130.53, 130.45, 126.26, 126.21, 125.96, 125.50, 125.07, 124.63, 124.38, 124.35, 122.36, 120.55, 118.99, 114.49, 114.19, 60.71, 52.71, 48.69, 30.94, 24.64.

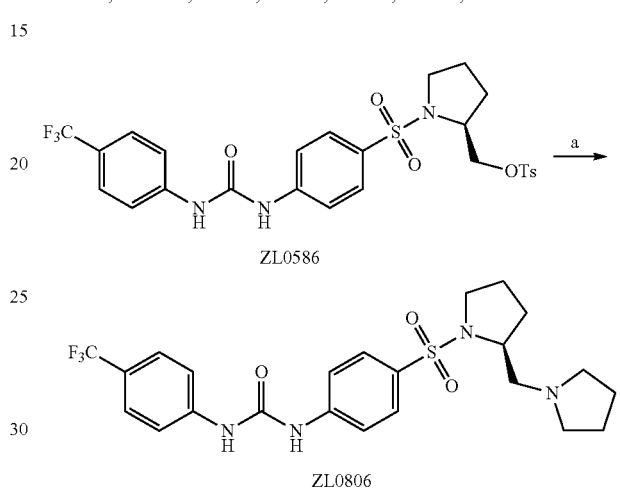

Reagents and conditions: (a) pyrrolidine, Et₃N, CH₃CN, 90° C., 37%.

Synthesis of (S)-1-(4-((2-(pyrrolidin-1-ylmethyl)pyrrolidin-1-yl)sulfonyl)phenyl)-3-(4-(trifluoromethyl) phenyl) urea (ZL0806). ZL0806 (18 mg, 37%) was obtained as a yellow oil following the procedure of ZL0742. $^{1}$H NMR (300 MHz, CDCl₃) δ 8.90 (s, 1H), 8.70 (s, 1H), 7.72-7.54 (m, 6H), 7.49 (d, J=8.5 Hz, 2H), 3.74 (s, 1H), 3.55 (d, J=14.2 Hz, 1H), 3.37 (s, 1H), 3.14 (dd, J=15.4, 8.4 Hz, 1H), 2.81-2.69 (m, 5H), 1.82 (s, 6H), 1.62-1.47 (m, 2H). $^{13}$C NMR (75 MHz, CDCl₃) δ 152.48, 144.11, 141.92, 129.35, 128.60, 126.20, 126.15, 126.10, 126.05, 126.02, 125.43, 125.00, 124.56, 124.13, 122.42, 118.73, 118.58, 61.24, 59.05, 54.98, 49.23, 29.76, 23.93, 23.44.

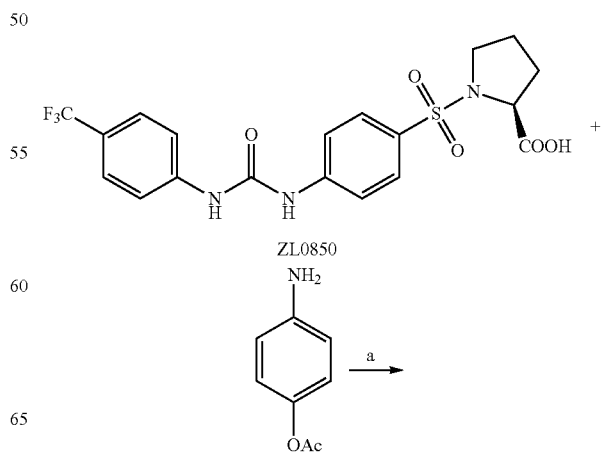

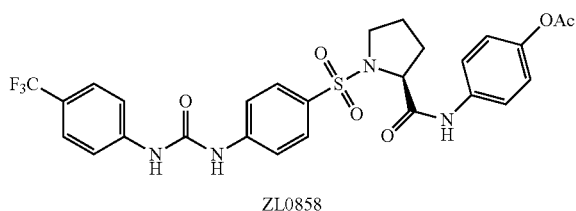

ZL0858

Reagents and conditions: (a) HBTU, DIEA, DCM, rt., quant.

Synthesis of (S)-4-(1-((4-(3-(4-(trifluoromethyl)phenyl) ureido)phenyl)sulfonyl) pyrrolidine-2-carboxamido)phenyl acetate (ZL0858). ZL0858 (59 mg, quant.) was obtained as a white powder following the procedure of ZL07100. $^1$H NMR (300 MHz, DMSO-$d_6$) δ 10.00 (s, 1H), 9.31 (d, J=20.4 Hz, 2H), 7.81 (d, J=7.9 Hz, 2H), 7.74-7.61 (m, 8H), 7.13-7.04 (m, 2H), 4.18 (d, J=7.3 Hz, 1H), 3.48 (s, 1H), 3.23 (s, 1H), 2.68 (d, J=2.0 Hz, 1H), 2.25 (d, J=3.3 Hz, 3H), 1.88 (s, 3H), 1.55 (s, 1H). $^{13}$C NMR (75 MHz, DMSO-$d_6$) δ 170.54, 169.72, 152.47, 146.56, 144.28, 143.45, 136.70, 130.01, 129.13, 126.74, 126.60, 126.54, 122.36, 120.95, 118.64, 118.44, 62.33, 49.59, 31.51, 24.76, 21.25.

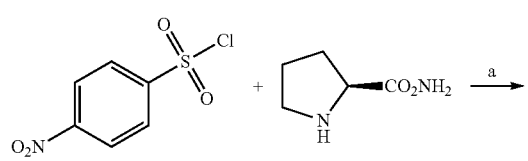

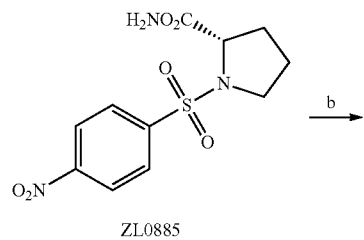

ZL0885

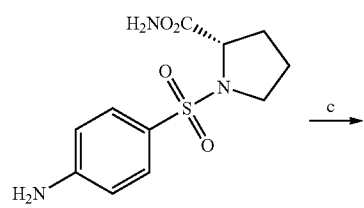

ZL0887

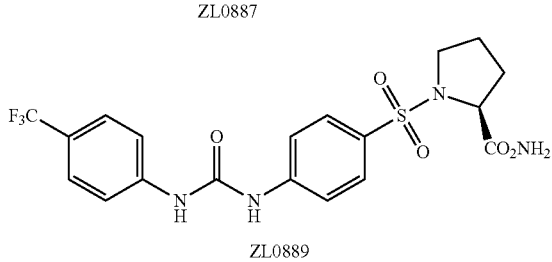

ZL0889

Reagents and conditions: (a) DIPEA, DCM, 0-25° C., 89%; (b) Zn, NH$_4$Cl, EtOH/H$_2$O, 80° C., 68%; (c) 1-isocyanato-4-(trifluoromethyl)benzene, DCM, rt, 39%.

Synthesis of (S)-1-(4-((2-((aminooxy)carbonyl)pyrrolidin-1-yl)sulfonyl)phenyl)-3-(4-(trifluoromethyl)phenyl) urea (ZL0889). ZL0889 (90 mg, 39%) was obtained as a white solid following the procedure of ZL0848. $^1$H NMR (300 MHz, MeOD) δ 7.84 (d, J=8.9 Hz, 2H), 7.78-7.71 (m, 2H), 7.68 (d, J=8.6 Hz, 2H), 7.61 (d, J=8.8 Hz, 2H), 4.08 (dd, J=8.1, 3.9 Hz, 1H), 3.63-3.51 (m, 1H), 3.30-3.20 (m, 1H), 2.03-1.78 (m, 3H), 1.71-1.57 (m, 1H). $^{13}$C NMR (75 MHz, MeOD) δ 176.32, 152.65, 144.14, 142.52, 129.41, 129.41, 128.76, 126.22, 125.76, 125.71, 125.66, 125.61, 124.75, 124.32, 123.89, 123.46, 122.64, 118.34, 118.21, 62.04, 49.31, 30.68, 24.11.

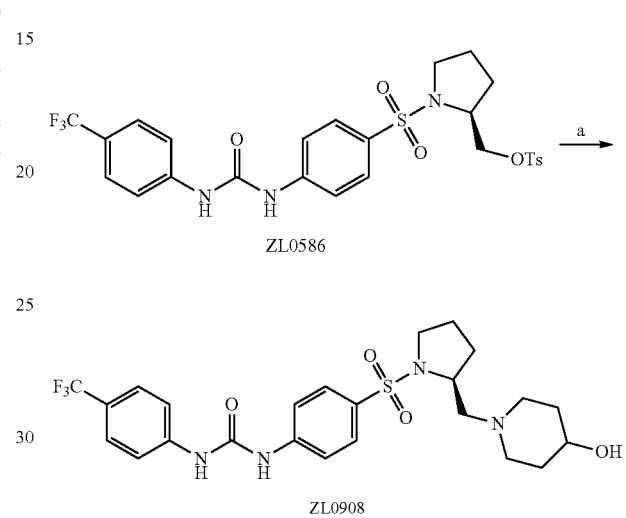

ZL0586

ZL0908

Reagents and conditions: (a) piperidine-4-ol, K$_2$CO$_3$, DMF, 50° C., 73%.

Synthesis of (S)-1-(4-((2-((4-hydroxypiperidin-1-yl)methyl)pyrrolidin-1-yl)sulfonyl)phenyl)-3-(4-(trifluoromethyl)phenyl)urea (ZL0908). ZL0908 (180 mg, 73%) was obtained as a white solid following the procedure of ZL0590. $^1$H NMR (300 MHz, MeOD) δ 7.81 (d, J=8.5 Hz, 2H), 7.75-7.64 (m, 4H), 7.60 (d, J=8.6 Hz, 2H), 3.81-3.70 (m, 1H), 3.62 (dt, J=9.4, 4.9 Hz, 1H), 3.37 (dd, J=9.6, 5.7 Hz, 1H), 3.23-3.12 (m, 1H), 2.89 (ddt, J=32.7, 10.4, 4.5 Hz, 2H), 2.66 (dd, J=12.6, 3.8 Hz, 1H), 2.47-2.16 (m, 3H), 1.84 (p, J=6.1, 5.1 Hz, 4H), 1.58 (q, J=11.5, 7.9 Hz, 4H). $^{13}$C NMR (75 MHz, MeOD) δ 152.68, 143.69, 142.54, 130.37, 128.49, 126.22, 125.76, 125.72, 125.67, 125.62, 124.70, 124.27, 123.83, 123.40, 122.64, 118.32, 118.17, 67.10, 62.97, 58.14, 52.25, 51.24, 48.69, 33.65, 33.54, 29.73, 23.44.

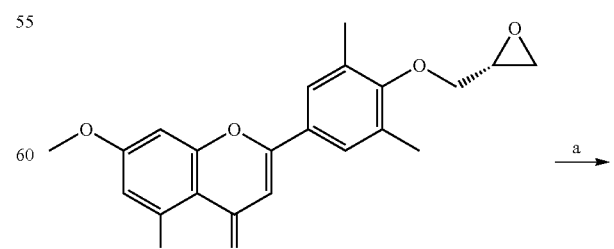

ZL0508

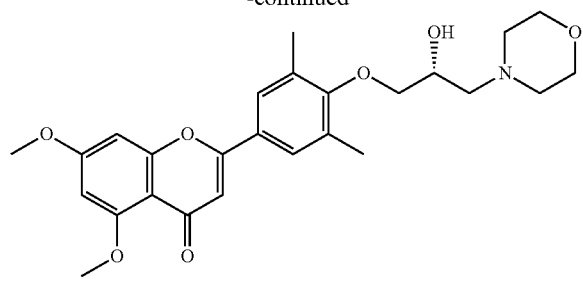

ZL0912

Reagents and conditions: (a) morpholine, K₂CO₃, DMF, refulx, overnight, 65%.

Synthesis of (R)-2-(4-(2-hydroxy-3-morpholinopropoxy)-3,5-dimethylphenyl)-5,7-dimethoxy-4H-chromen-4-one (ZL0912). ZL0912 (76 mg, 65%) was obtained as a white solid following the procedure of ZL0513. ¹H NMR (300 MHz, MeOD) δ 7.42 (d, J=3.3 Hz, 2H), 6.55 (d, J=2.3 Hz, 1H), 6.41 (s, 1H), 6.34 (d, J=2.4 Hz, 1H), 4.14 (dd, J=7.7, 4.6 Hz, 1H), 3.88 (s, 3H), 3.84 (s, 3H), 3.80 (dd, J=4.8, 3.0 Hz, 2H), 3.74 (t, J=4.7 Hz, 3H), 3.67 (t, J=4.8 Hz, 1H), 3.33 (t, J=1.7 Hz, 1H), 2.61 (td, J=8.5, 7.7, 4.0 Hz, 5H), 2.29 (s, 6H). ¹³C NMR (75 MHz, MeOD) δ 178.26, 164.73, 161.32, 160.41, 159.60, 158.52, 131.61, 126.34, 125.96, 107.76, 106.51, 95.84, 92.64, 74.30, 67.35, 66.46, 61.02, 55.10, 55.04, 53.98, 15.31.

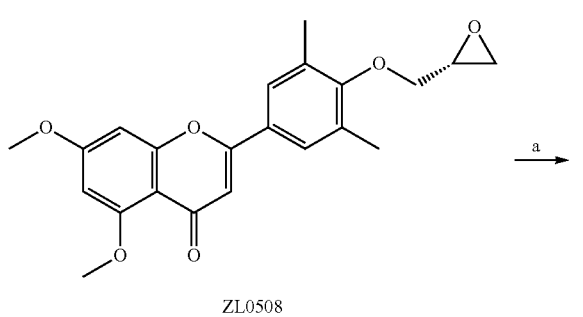

ZL0508

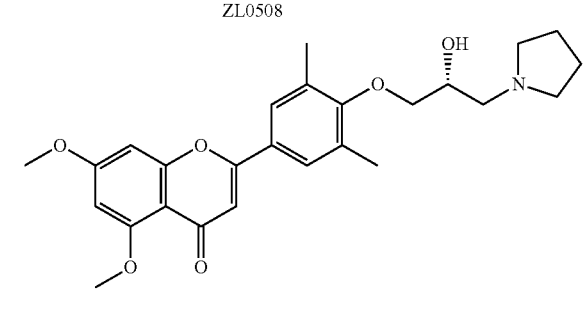

ZL0913

Reagents and conditions: (a) pyrrolidine, K₂CO₃, DMF, refulx, overnight, 27%.

Synthesis of (R)-2-(4-(2-hydroxy-3-(pyrrolidin-1-yl)propoxy)-3,5-dimethylphenyl)-5,7-dimethoxy-4H-chromen-4-one (ZL0913). ZL0913 (30 mg, 27%) was obtained as a white solid following the procedure of ZL0513. ¹H NMR (300 MHz, MeOD) δ 7.49 (s, 2H), 6.62 (d, J=2.3 Hz, 1H), 6.47 (s, 1H), 6.39 (d, J=2.3 Hz, 1H), 4.15 (dd, J=8.8, 4.5 Hz, 1H), 3.97-3.75 (m, 9H), 2.88 (dd, J=12.6, 4.2 Hz, 1H), 2.74 (t, J=6.2 Hz, 4H), 2.32 (s, 6H), 1.86 (p, J=3.1 Hz, 4H). ¹³C NMR (75 MHz, MeOD) δ 178.34, 164.82, 161.44, 160.46, 159.69, 158.56, 131.64, 126.40, 126.05, 107.80, 106.56, 95.89, 92.67, 74.53, 68.94, 58.68, 55.11, 55.06, 54.28, 22.90, 15.29.

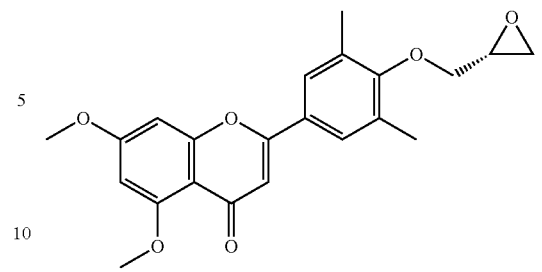

ZL0508

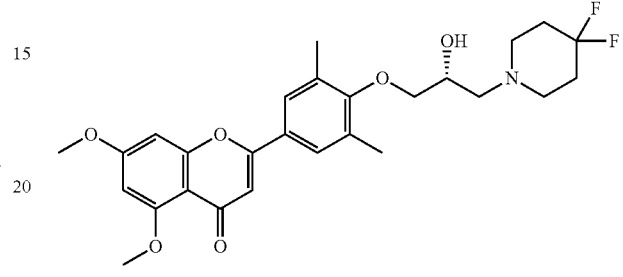

ZL0914

Reagents and conditions: (a) 4,4-difluoropiperidine, K₂CO₃, DMF, refulx, overnight, 60%.

Synthesis of (R)-2-(4-(3-(4,4-difluoropiperidin-1-yl)-2-hydroxypropoxy)-3,5-dimethylphenyl)-5,7-dimethoxy-4H-chromen-4-one (ZL0914). ZL0914 (75 mg, 60%) was obtained as a white solid following the procedure of ZL0513. ¹H NMR (300 MHz, CDCl₃) δ 7.51 (s, 2H), 6.60-6.52 (m, 2H), 6.35 (d, J=2.3 Hz, 1H), 4.10 (dd, J=8.9, 4.6 Hz, 1H), 3.92 (d, J=9.6 Hz, 6H), 3.84 (d, J=5.6 Hz, 2H), 2.85-2.75 (m, 2H), 2.65 (td, J=8.5, 5.6 Hz, 4H), 2.35 (s, 6H), 2.12-1.95 (m, 4H). ¹³C NMR (75 MHz, CDCl₃) δ 177.51, 163.93, 160.84, 160.54, 159.84, 158.09, 131.57, 126.98, 126.70, 124.81, 121.61, 118.41, 109.18, 108.44, 96.10, 92.78, 77.26, 74.08, 66.75, 59.51, 56.35, 55.73, 50.42, 50.35, 50.28, 34.35, 34.04, 33.74, 16.49.

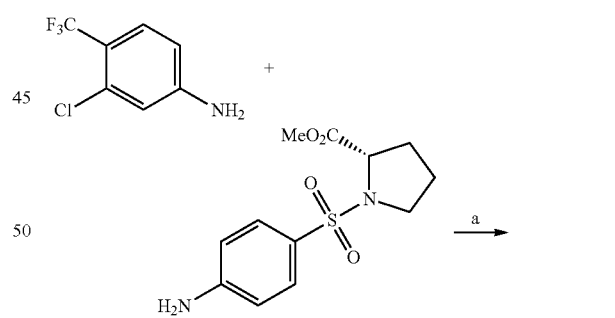

ZL0924

Reagents and conditions: (a) triphosgene, tolene, 120° C., overnight, 41%.

Synthesis of methyl ((4-(3-(3-chloro-4-(trifluoromethyl)phenyl)ureido)phenyl)sulfonyl)-L-prolinate (ZL0924). To a solution of triphosgene (50 mg, 0.17 mmol) in 5 mL tolene under N₂, 3-chloro-4-(trifluoromethyl)aniline (98 mg, 0.5 mmol) was added. After stirring at 120° C. for 2 h, methyl ((4-aminophenyl)sulfonyl)-L-prolinate (50 mg, 0.175 mmol) was added. Then the solution was allowed to stir at 120° C. for overnight before concentration. The residue was purified by PTLC to get ZL0924 (35 mg, 41%) as a white solid. ¹H NMR (300 MHz, MeOD) δ 7.91 (d, J=2.1 Hz, 1H), 7.85-7.79 (m, 2H), 7.74-7.66 (m, 3H), 7.49 (dd, J=8.6, 2.0 Hz, 1H), 4.26 (dd, J=8.0, 4.0 Hz, 1H), 3.75 (s, 3H), 3.54-3.43 (m, 1H), 3.29 (d, J=2.8 Hz, 1H), 2.07-1.91 (m, 3H), 1.73 (dd, J=7.2, 5.0 Hz, 1H). ¹³C NMR (75 MHz, MeOD) δ 173.13, 152.39, 143.71, 143.65, 132.24, 130.89, 128.42, 128.03, 127.93, 127.86, 127.79, 127.72, 124.97, 121.49, 121.37, 121.07, 120.24, 118.30, 116.08, 60.51, 51.51, 48.41, 30.49, 24.21.

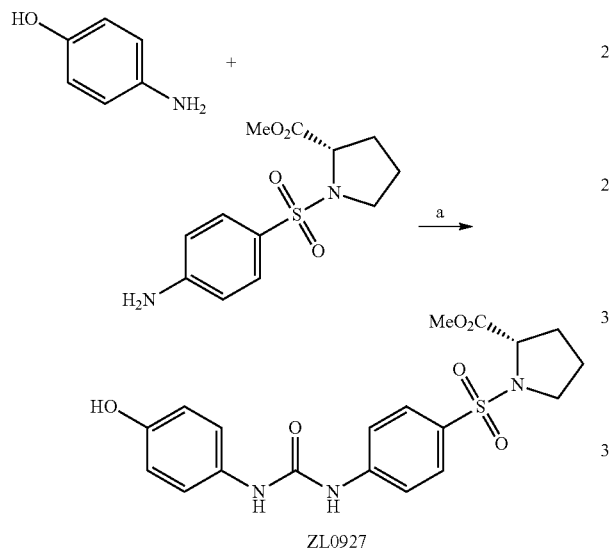

ZL0927

Reagents and conditions: (a) triphosgene, tolene, 120° C., overnight, 44%.

Synthesis of methyl ((4-(3-(4-hydroxyphenyl)ureido)phenyl)sulfonyl)-L-prolinate (ZL0927). ZL0927 (46 mg, 44%) was obtained following the procedure of ZL0924. ¹H NMR (300 MHz, MeOD) δ 7.77 (d, J=8.8 Hz, 2H), 7.66 (d, J=8.9 Hz, 2H), 7.24 (d, J=8.8 Hz, 2H), 6.77 (d, J=8.8 Hz, 2H), 4.24 (dd, J=8.0, 4.1 Hz, 1H), 3.74 (s, 3H), 3.53-3.43 (m, 1H), 3.32-3.22 (m, 1H), 1.98 (dddt, J=16.3, 12.1, 8.2, 4.3 Hz, 3H), 1.72 (td, J=7.1, 4.8 Hz, 1H). ¹³C NMR (75 MHz, MeOD) δ 173.14, 153.80, 153.62, 144.37, 130.13, 130.05, 128.38, 122.06, 117.92, 115.02, 60.50, 51.49, 48.42, 30.48, 24.21.

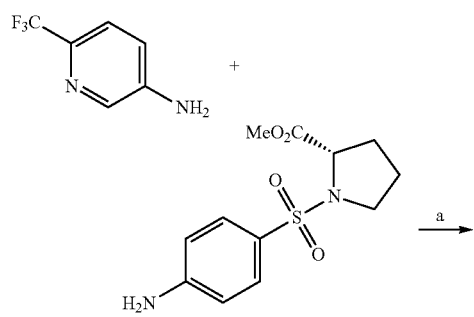

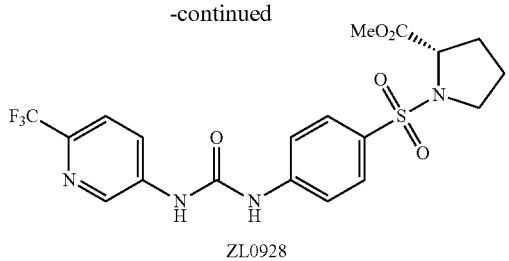

ZL0928

Reagents and conditions: (a) triphosgene, tolene, 120° C., overnight, quant.

Synthesis of methyl ((4-(3-(6-(trifluoromethyl)pyridin-3-yl)ureido)phenyl)sulfonyl)-L-prolinate (ZL0928). ZL0928 (183 mg, quant.) was obtained following the procedure of ZL0924. ¹H NMR (300 MHz, CDCl₃) δ 8.64 (d, J=6.7 Hz, 1H), 8.38-8.30 (m, 1H), 8.21 (q, J=12.2, 10.5 Hz, 2H), 7.77 (d, J=8.3 Hz, 2H), 7.65 (d, J=8.9 Hz, 3H), 4.35-4.20 (m, 1H), 3.72 (s, 3H), 3.53 (dt, J=12.1, 6.0 Hz, 1H), 3.25 (q, J=7.9 Hz, 1H), 2.02 (dh, J=15.2, 7.7 Hz, 3H), 1.84-1.69 (m, 1H). ¹³C NMR (75 MHz, CDCl₃) δ 173.04, 151.96, 151.87, 151.79, 143.79, 143.74, 142.01, 141.55, 141.08, 140.37, 138.35, 130.10, 128.62, 126.37, 126.30, 123.46, 121.03, 119.84, 119.00, 118.94, 60.73, 52.76, 48.75, 30.91, 24.65.

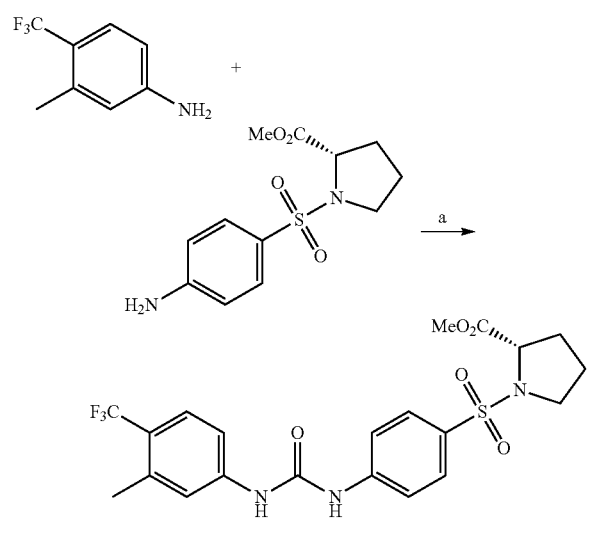

ZL0929

Reagents and conditions: (a) triphosgene, tolene, 120° C., overnight, 30%.

Synthesis of methyl ((4-(3-(3-methyl-4-(trifluoromethyl)phenyl)ureido)phenyl)sulfonyl)-L-prolinate (ZL0929). ZL0929 (25 mg, 30%) was obtained following the procedure of ZL0924. ¹H NMR (300 MHz, CDCl₃) δ 7.98 (s, 1H), 7.80 (s, 1H), 7.74 (d, J=8.4 Hz, 2H), 7.65 (s, 1H), 7.56 (dd, J=16.6, 8.4 Hz, 3H), 7.18 (d, J=8.3 Hz, 1H), 4.26 (t, J=6.4 Hz, 1H), 3.72 (s, 3H), 3.50 (dt, J=11.7, 5.6 Hz, 1H), 3.24 (q, J=7.8 Hz, 1H), 2.39 (s, 3H), 2.00 (tt, J=13.7, 6.4 Hz, 3H), 1.75 (d, J=15.3 Hz, 1H). ¹³C NMR (75 MHz, CDCl₃) δ 172.94, 152.60, 143.90, 136.13, 132.50, 131.48, 130.09, 129.38, 128.98, 128.60, 126.04, 123.00, 122.41, 118.83, 117.52, 117.44, 60.65, 52.61, 48.66, 30.87, 24.61, 18.58.

hSAEC culture and induction of the mesenchymal transition. An immortalized human small airway epithelial cell (hSAEC) line established by infecting primary hSAECs with human telomerase (hTERT) and cyclin-dependent kinase (CDK)-4 retrovirus constructs was obtained from Dr. John Minna, UTSW. The immortalized hSAECs were grown in SAGM small airway epithelial cell growth medium (Lonza, Walkersville, Md.) in a humidified 5% $CO_2$ atmosphere. Poly(I:C) was obtained from Sigma (St. Louis, Mo.) and used at 10 µg/ml in cell culture. JQ1 was purchased from Cayman Chemical (Ann Arbor, Mich.).

In vitro efficacy of BRD4 inhibitors on poly(I:C) induced innate immune response. hSAECs were pretreated with a series final concentrations of BRD4 inhibitors from 0.01 nM to 100 µM for 24 hours and were added Poly(I:C) at 10 µg/ml in cell culture for another 4 hours prior to harvesting the cells. The harvested cells were first washed with PBS twice and the total RNA was extracted using acid guanidinium phenol extraction (Tri Reagent; Sigma). The total RNA was reverse-transcribed for gene expression analysis by Q-RT-PCR. The inhibitory effect of BRD4 inhibitors on poly(I:C) induced NFkB gene and ISGs gene expression were compared with that of poly (I:C) alone and inhibitory percentage of each treatment was obtained. For comparison with the compounds, In vitro efficacy of these BRD4 inhibitors on poly(I:C) induced innate immune response were presented as the IC50 values of these compounds.

Quantitative Real-Time PCR (Q-RT-PCR). For gene expression analyses, 1 µg of RNA was reverse transcribed using Super Script III in a 20 µl reaction mixture. One µ of cDNA product was diluted 1:2, and 2 µL of diluted product was amplified in a 20 µL reaction mixture containing 10 µL of SYBR Green Supermix (Bio-Rad) and 0.4 µM each of forward and reverse gene-specific primers. The reaction mixtures were aliquoted into Bio-Rad 96-well clear PCR plate and the plate was sealed by Bio-Rad Microseal B film before putting into PCR machine. The plates were denatured for 90 s at 95° C. and then subjected to 40 cycles of 15 s at 94° C., 60 s at 60° C., and 1 min at 72° C. in an iCycler (BioRad). PCR products were subjected to melting curve analysis to assure that a single amplification product was produced. Quantification of relative changes in gene expression was calculated using the ΔΔCt method and expression as the fold change between experimental and control samples.

Plate-based time-resolved fluorescence energy transfer (TR-FRET) assays to determine the binding ability of BRD4 compounds to bromodomains of BRD2 and BRD4. 96 well plate based commercial TR-FRET Assay kits (Cayman Chemical, Ann Arbor, Mich.) were used to determine the binding ability of tested BRD4 inhibitors to the BRD4 bromodomains (BD) using the two recombinant BRD4 BDs using time-resolved fluorescence energy transfer (TR-FRET) assays. A series concentrations of BRD4 inhibitors from 0.01 nM to 100 µM for 24 hours and were added into 96 well test plate and mixed with other reaction components based on the instructions from vendor followed by incubation 1 h at room temperature. The commercially available BRD inhibitor JQ1 was used as the positive control. The plate were read in time-resolved format by exciting the sample at 340 nm and reading emissions at 620 and 670 nm, using a 100 µs delay and a 500 µs window at a Tecan M1000 pro reader. A plot of the TR-FRET ratio (670 nm emission/ 620 nm emission0 versus inhibitor concentration on semi-log axes results in a sigmoidal dose-response curve typical of competitive assays. These data were further calculated out the IC50 values of tested BRD4 inhibitors to the bromodomains of BRD2 and BRD4 respectively.

In vivo efficacy of BRD4 inhibitors on acute poly(I:C) exposure-induces airway inflammation. Animal experiments were performed according to the NIH Guide for Care and Use of Experimental Animals and approved by the University of Texas Medical Branch (UTMB) Animal Care and Use Committee (approval no. 1312058). Male C57BL6/J mice (18 weeks old) were purchased from The Jackson Laboratory (Bar Harbor, Me.) and housed under pathogen-free conditions with food and water ad libitum. C57BL/6 mice were pretreated with or without BRD4 inhibitors (50 mg/kg) intraperitoneal (IP) route. 24 h later, mice were given another administration of BRD4 inhibitors via the IP route and stimulated intranasally with either 50 µL of PBS or 50 µL PBS+300 µg poly(I:C) for 24 h. Afterwards, the mice were sacrificed to obtain bronchoalveolar lavage fluid (BALF), and lungs were harvested for histology and to isolate total RNA. For histological examination, whole lungs were inflated under 25 cm H2O pressure with 10% (v/v) neutral buffered formalin through a tracheal cannula and were immersed in formalin for at least 24 h. After being processed into paraffin blocks, the lungs were cut into 5-µm sections and were either stained stained with H&E to assess airway inflammation of mice.

In vivo efficacy of BRD4 inhibitors on chronic poly(I:C) treatment-induced pulmonary fibrosis model of mice. Animal experiments were performed according to the NIH Guide for Care and Use of Experimental Animals and approved by the University of Texas Medical Branch (UTMB) Animal Care and Use Committee (approval no. 1312058). Male C57BL6/J mice (18 weeks old) were purchased from The Jackson Laboratory (Bar Harbor, Me.) and housed under pathogen-free conditions with food and water ad libitum. Under mild anesthesia, mice were given repetitive poly(I:C) challenges every other days for a total of 15 administrations (500 µg/dose in 50 µL PBS). In parallel, mice were pre-treated with or without BRD4 inhibitors (50 mg/kg body weight, i. p.) prior to poly(I:C) challenge. 12 days after last poly(I:C) treatment, the mice were sacrificed, 12 days after last poly(I:C) treatment, the mice were sacrificed to obtain bronchoalveolar lavage fluid (BALF), and lungs were harvested for histology and to isolate total RNA. For histological examination, whole lungs were inflated under 25 cm $H_2O$ pressure with 10% (v/v) neutral buffered formalin through a tracheal cannula and were immersed in formalin for at least 24 h. After being processed into paraffin blocks, the lungs were cut into 5-µm sections and were either stained stained with Masson Trichrome or H&E to assess fibrotic changes in the lungs.

Assessment of levels of pulmonary fibrosis. Pulmonary fibrosis was graded using the Ashcroft scoring method as described. In brief, to determine the fibrosis histopathology score for the lung of each mouse, the entire left and right longitudinal lung sections were scored separately (score range, 0 to 9) at ×100 magnification, and the scores were combined (total score range, 0 to 18) (33). Grades 2, 4, 6, and 8 were intermediate grades assigned on the basis of the predominant histology changes if features described for two distinct grades (as described) were present in the section, to account for the progressive nature of the fibrotic lesion.

Statistical analysis. One-way analysis of variance (ANOVA) was performed when looking for time differences, followed by Tukey's post hoc test to determine significance. Mann-Whitney tests were used for nonparametric data. All data subjected to statistical analysis are the mean±S.D. from n=3 experiments. A P value of <0.05 was considered significant.

B. Results

Figure 1B:
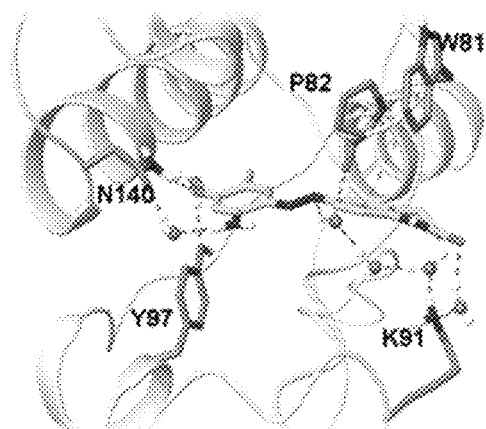
Figure 1C:
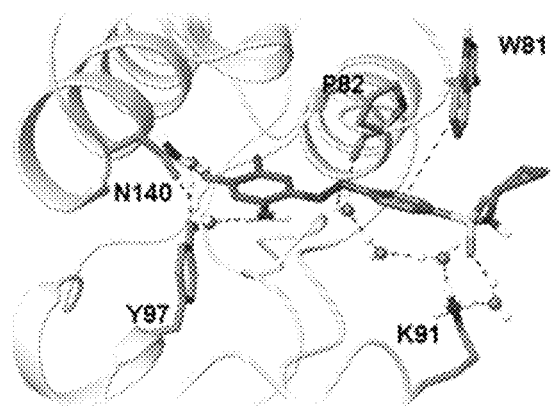
Figure 1D:
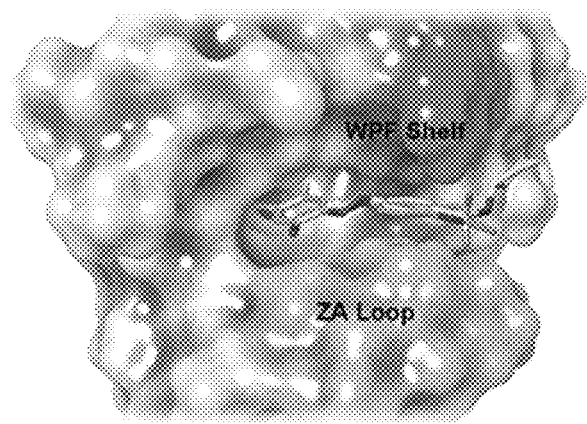
Figure 2:
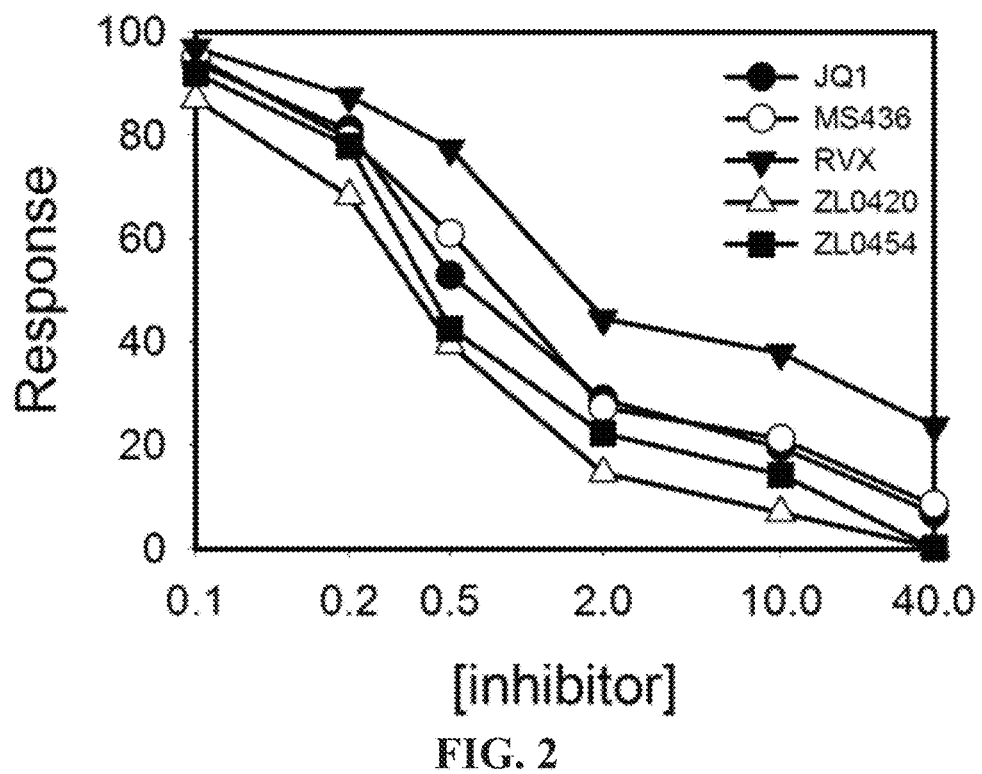
FIG. 2. Dose response profiles of BRD4 inhibitors. Shown are JQ1, MS436, RVX208, ZL0420 and ZL0454 inhibitors in a cell based assay for effect on IL-6 gene expression. Data are presented as % inhibition of untreated cells.

Design and synthesis of BRD4 inhibitors. Analysis of the crystal structures of BRD4 bromodomain reveals that the acetylated lysine (KAc) binding pocket is anchored by the conserved residue Asn140 and Tyr97 and surrounded by hydrophobic WPF shelf and ZA loop. New BRD4 inhibitors ZL0420 and ZL0454 (chemical structures shown in FIG. 1a) were designed by taking advantage of substituted amino phenol moiety as the polar head of our ligand, diazene as the linker and dihydroquinolin-2(1H)-one or N-cyclopentylbenzenesulfonamide as the binding tails to fit into BRD4 BD1 domain. As depicted in FIGS. 1b and 1c, docking studies utilizing in-house Cybertron i7-4770K 3.5 GHz workstation with the Schrödinger Advanced Drug Discovery Suite demonstrated that these two inhibitors can be well docked into BRD4 BD1 in a similar binding mode. Both compounds can well interact with Asn140 directly through the hydroxyl group of phenol ring and form hydrogen bonds with Tyr97 mediated by a water molecule. In addition, the phenyl ring of both molecules on their tails can form a T shape $\pi$-$\pi$ interaction with Trp81, while the diazene linker interacts with Lys91 mediated by water molecules. These two inhibitors are sandwiched by the WPF shelf and residues from ZA loop (FIG. 1d), thereby allowing strong interactions of the ligand and high binding affinities with the protein.

Figure 3:
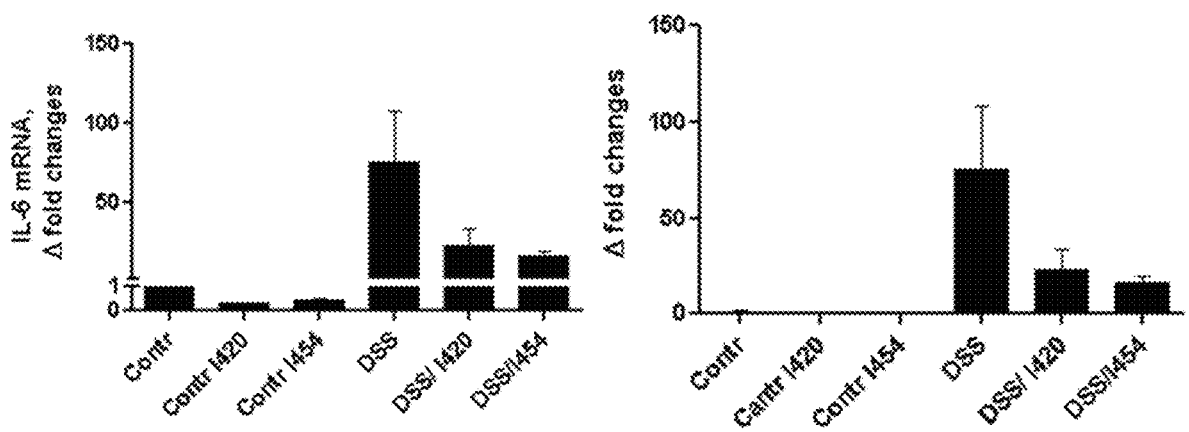
FIG. 3. BRD4 inhibitors suppress IL-6 inflammatory response during initiation of the colonic inflammation in murine model of acute DSS colitis. Colitis was induced in C57Bl6 mice by supplementation of the drinking water with 3% DSS. BRD4 inhibitors ZL0420 (I420) and ZL0454 (I454) were administrated by i.p. injection daily. Animals were euthanized on day 7 after initiation of colitis and RNA was isolated from colonic mucosa. The IL-6 mRNA expression was analyzed by using real time RT-PCR and reported as the DDCt fold-difference relative to the murine housekeeping gene, b-actin mRNA, One way Anova with Turkey post-test for the multiple comparison was used to calculate statistical significance, n=4 mice per group, *=p<0.05.
Figure 4:
FIG. 4. BRD4 inhibitors reduce colonic inflammation in murine model of acute DSS colitis. H&E analysis, partial normalization of the colonic architecture and decrease in the lymphocyte infiltration was observed when DSS treated animals received BRD4 inhibitors treated with in the animal groups treated with ZL0420 (I420) or ZL0454 (I454).
Figure 6:
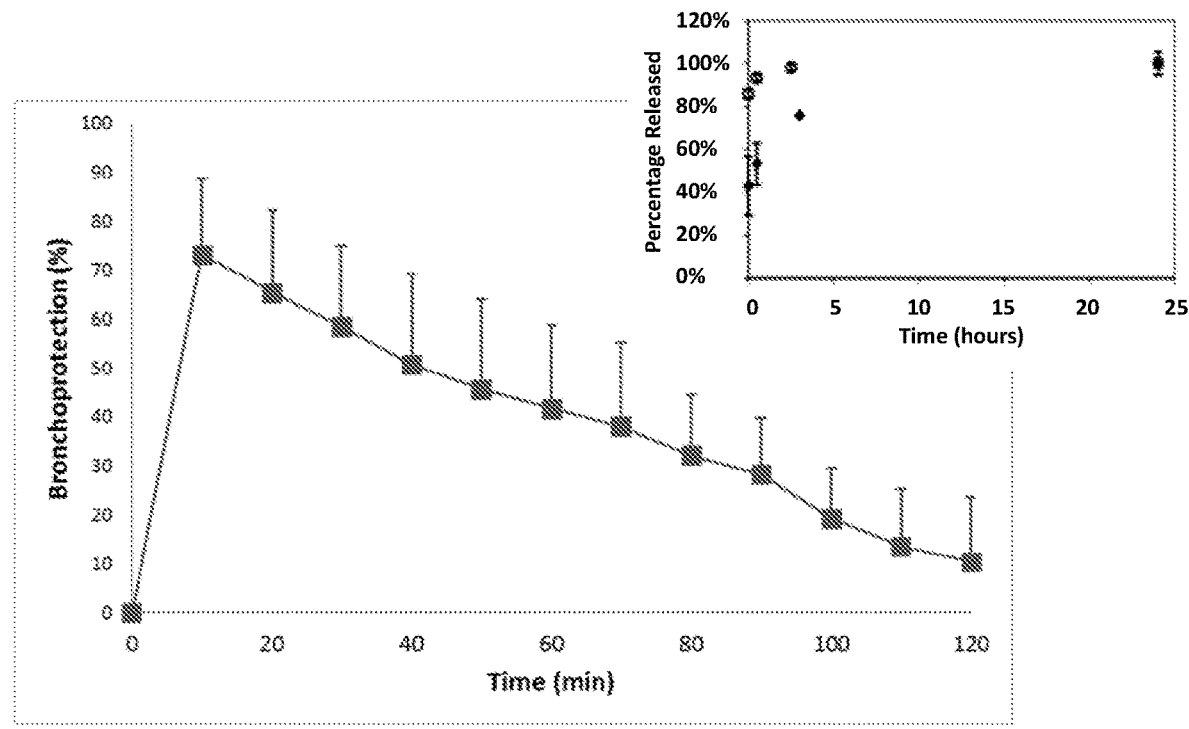
FIG. 6. In vivo bronchoprotection against acetylcholine-induced bronchospasm in guinea pigs following nebulization of polymeric nanoparticles loaded with salbutamol (Rytting et al. *Expert Opinion on Drug Delivery*, 5:629-39, 2008).
Figure 7:
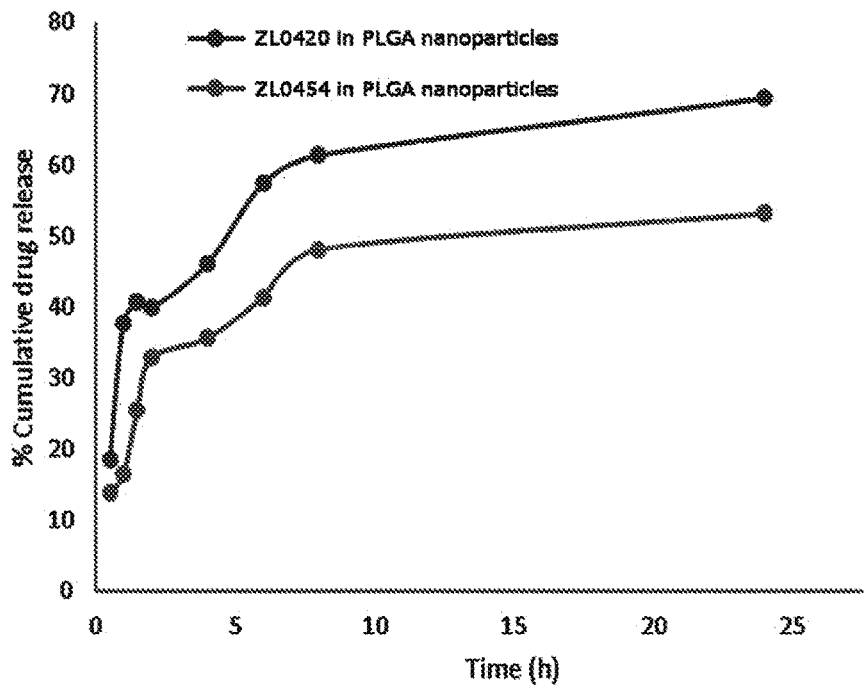
FIG. 7. Drug release from nanoparticles.

The in vivo efficacy of compounds ZL0420 and ZL0454 on inhibiting colonic inflammation in murine model of acute DSS colitis have been carried out (FIG. 3 to FIG. 5). These two compounds significantly suppress IL-6 inflammatory response during initiation of the colonic inflammation in murine model of acute DSS colitis (FIG. 3). Partial normalization of the colonic architecture and decrease in the lymphocyte infiltration were observed when DSS treated animals received the treatment of BRD4 inhibitors ZL0420 and ZL0454 (FIG. 4). It was observed that, in solvent only-treated controls, poly(I:C) induced a dramatic neutrophilia in airway bronchoalveolar lavage (BALF) and enhanced IL-6 secretion (FIGS. 5A and 5B). Histologically, poly(I:C) produced a marked infiltration of neutrophils in the lung tissue (FIG. 5, middle panel). All of these responses were nearly completely inhibited by the administration of JQ1, ZL0420 and ZL0454 compounds (FIGS. 5A and 5B).

Example 2

Figure 8:
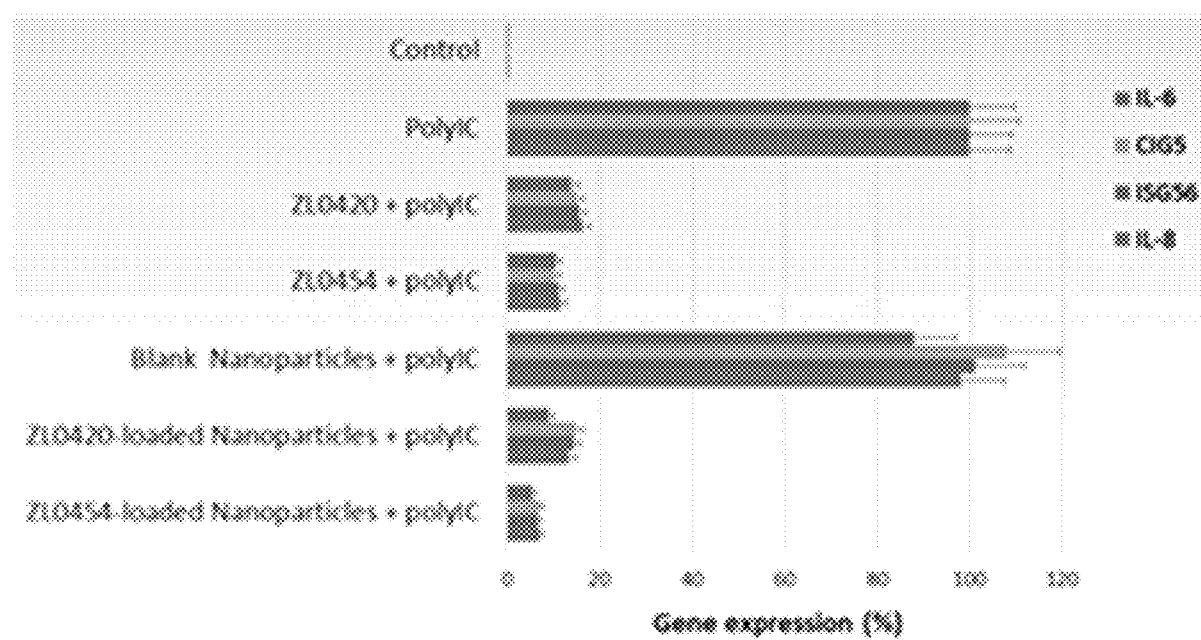
FIG. 8. Effect of nanoparticles on BRD4 pathway.
Figure 9:
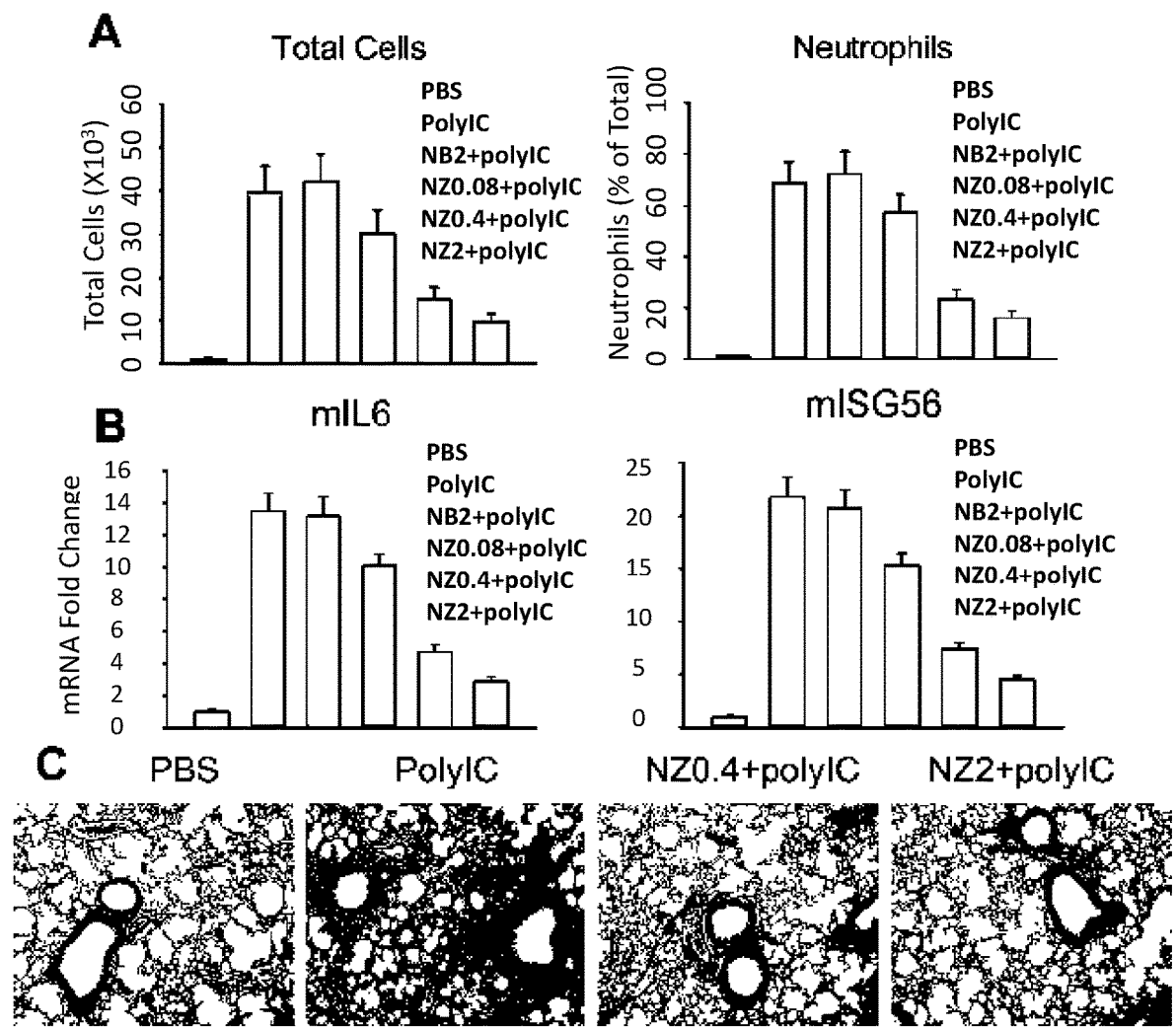
FIGS. 9A-C. In vivo efficacy of ZL0420-nanoparticles. Illustrates the effects of nanoparticles at 0.4 mg/kg and at 2 mg/kg on (9A) total cells and neutrophils, and (9B) mRNA level for mIL6 and mISG56, and (9C) cellular infiltration.
Figure 10:
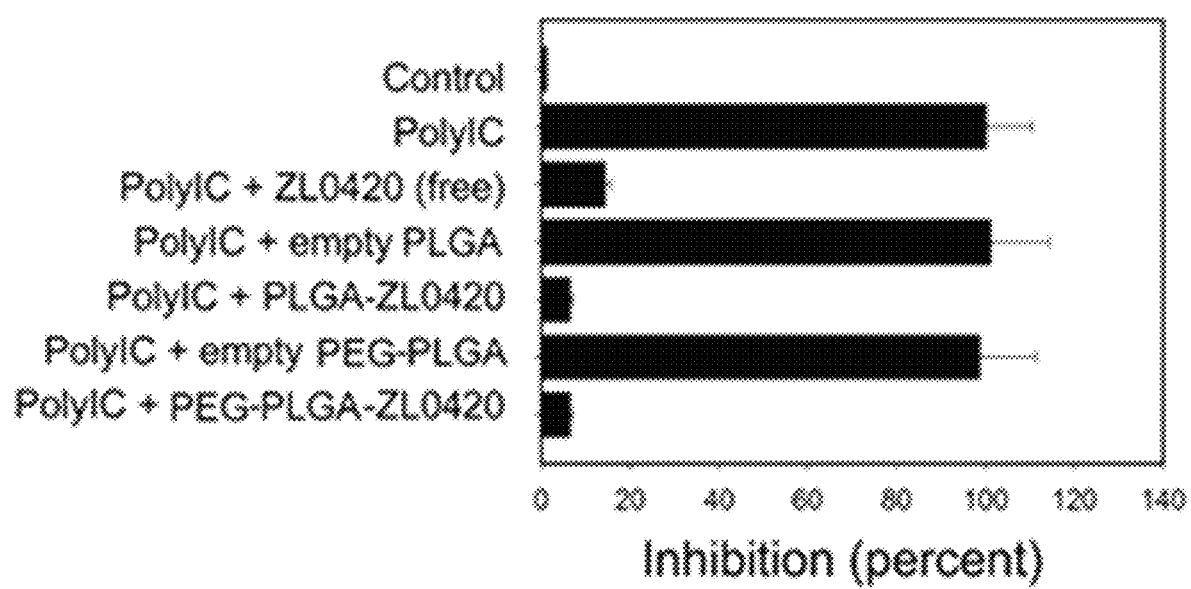
FIG. 10. Effect of ZL0420 and ZL0420-loaded nanoparticles on poly(I:C)-stimulated inflammatory gene activation.

Certain embodiments use novel molecular inhibitors encapsulated in nanoparticles for local delivery (via aerosols or inhalers). Advantages of nanoparticle-based delivery of the BRD4 inhibitors include the potential to reduce systemic exposure and resultant side effects by aerosolized delivery of the nanoencapsulated drugs to the airways. Delivery of the medication to the site of action would also allow for reduced overall dosing in comparison to systemic (i.v. or oral) dosing levels that would be required to achieve the same therapeutic response. In addition, sustained release of the therapeutic compound from the nanoparticles should increase the overall half-life of the drugs, potentially reducing the dosing frequency. Nanoparticle delivery by aerosolization was previously reported for polymeric nanoparticles loaded with salbutamol (Rytting et al., *Expert Opinion on Drug Delivery,* 5:629-39, 2008). FIG. 6 shows that the drug released from the nanoparticles maintains its pharmacological activity, as well as agreement between the kinetics of in vitro drug release from the nanoparticles and the sustained protection over time against acetylcholine-induced bronchospasm in anaesthetized guinea pigs (n=6, mean±s.d.), according to the Konzett-Rößler model. Acetylcholine was injected intravenously at a dose of 9 μg/kg every 10 minutes; after the first 10 minutes, salbutamol-loaded nanoparticles were administered once by nebulization of the aqueous nanoparticle suspension at a dose of 6 μg/kg using the Respimat® Soft Mist™ inhaler. Nanoparticle characteristics (particle size, surface charge, and drug loading) before and after nebulization were not significantly different.

TABLE 7

Characterization of polymeric (PLGA) nanoparticles loaded with BRD4 inhibitors.

| Compound | Particle size (nm) | Encapsulation efficiency (%) |
|---|---|---|
| ZL0420 | 92 ± 2 | 91.8 |
| ZL0454 | 117 ± 1 | 36.4 |

The inventors have successfully encapsulated the specific BRD4 inhibitors ZL0420 and ZL0454 into biodegradable (PEGylated) nanoparticles and conducted proof of efficacy. The lead compounds ZL0420 and ZL0454 were encapsulated into polymeric nanoparticles by a modified solvent displacement method. The polymeric matrix was comprised of poly(lactic-co-glycolic acid) (PLGA), a biodegradable and biocompatible polymer that has already gained FDA approval.

Particle diameter, encapsulation efficiency, and drug release were assessed (Table 7). The encapsulation efficiency is much greater for the ZL0420 compound, although the encapsulation efficiency of both compounds is acceptable for efficacy testing (Table 7).

Drug release was tested in vitro. Both compounds show an initial burst release over 3 h, followed by a longer release phase (FIG. 7). Efficacy testing was first performed using cultured human small airway epithelial cells (hSAECs). Cells were first pretreated with unencapsulated drug or nanoparticle preparations and followed by exposure to innate immune response stimulator PolyIC. mRNA expression for polyIC-induced BRD4-dependent genes was measured using Q-RT-PCR (FIG. 8). In comparison to the potent effect of polyIC to activate BRD4-dependent gene expression, the unencapsulated drugs reduced expression to less than 15% (FIG. 8). Blank nanoparticles had no inhibitory effect. Both ZL0420- and ZL0454-loaded nanoparticles potently inhibited BRD4-dependent gene expression, even slightly more potent than that of the unencapsulated drug. This difference may be due to the prolonged release or more efficient uptake.

Furthermore, we determined the in vivo efficacy of nanoparticle preparations in our mouse model of acute poly(I:C)-induced airway neutrophilic inflammation. ZL0420-encapsulated nanoparticles were administered to mice at different dosages (0.08, 0.4, and 2 mg/kg, i.n.) before poly(I:C) challenge. We observed that poly(I:C) induced a profound neutrophilic inflammation around the small and medium sized airways 24 h after introduction (FIG. 9C) that was effectively inhibited by ZL0420-encapsulated nanoparticles at dosages of both 0.4 and 2 mg/kg. The number of leukocytes in the BALF of poly(I:C)-treated mice was inhibited by ZL0420-encapsulated nanoparticle treatment (FIG. 9A, left panel). Also, the increased number of neutrophils in the BALF of PBS-treated mice exposed to poly(I:C) was reduced in mice treated with ZL0420-encapsulated nanoparticles and exposed to poly(I:C) (FIG. 9A, right panel). Correspondingly, poly(I:C)-induced mRNA expression of inflammatory cytokine IL6 and ISG56 were effectively blocked by ZL0420-encapsulated nanoparticles treatment (FIG. 9B).

Additional refinements of the nanoformulations containing the BRD4 inhibitor compounds include the encapsulation of BRD4 inhibitors in nanoparticles comprised of an additional biocompatible polymer, PEGylated poly(lactic-co-glycolic acid) (PEG-PLGA) and the optimization of nanoparticle synthesis and purification procedures to increase nanoparticle stability. This newer batch of nanoparticles (both PLGA and PEG-PLGA nanoformulations) still displayed therapeutic efficacy in vitro in human small airway epithelial cells (hSAECs). Repeating the experiments corresponding to FIG. 8 with this newer set of stabilized ZL0420-loaded nanoparticles (with Z-average particle diameters of 102 nm for PLGA nanoparticles and 131 nm for the PEG-PLGA nanoparticles), FIG. 10 shows that both types of polymeric drug-loaded nanoparticles outperform the unencapsulated free drug ZL0420 in reducing poly(I:C)-induced activation of inflammatory genes.

Example 3

Evaluation of the in vivo efficacy of optimized BRD4 inhibitors ZL0516 and ZL0590 in DSS-induced colitis model. Epithelial damage and impaired wound healing are major issues impeding the efficiency of current ulcerative colitis (UC) therapies. Thus, the inventors first test the efficacy of BRD4 inhibitors in DSS-induced acute colitis which mimics the initiation of colitis by epithelial injury. This colitis model mimics epithelial barrier disruption and is widely used to assess mucosal inflammation and healing (Low et al., *Drug Des Devel Ther* 2013, 7:1341-57). The efficacy of ZL0516 and ZL0590 will be examined in the DSS colitis model in C57BL/6 mice and analyze the relevant biomarkers.

Evaluation of the in vivo efficacy of ZL0516 and ZL0590 in an animal model mimicking chronic UC. T helper lymphocyte Th2/Th17 chronic inflammatory responses are key events contributing to mucosal ulceration in IBD. The DSS-induced model of chronic colitis mimicking chronic UC will be used to test the compounds. Also, selected candidates can be tested using the model of oxazolone (oxa)-induced chronic colitis (Low et al., *Drug Des Devel Ther* 2013, 7:1341-57). Both models result in chronic long-lasting colonic inflammation, mimicking the histological features and Th2 and Th17 responses seen in human UC (Beswick et al., *J Immunol* 2014, 193:2218-29; Heller et al., *Immunity* 2002, 17:629-38; Kim et al., *J Vis Exp* 2012, 84-86).

Evaluation of the in vivo efficacy of ZL0516 and ZL0590 in the Cbir1 CD4+ T cell transfer model of IBD colitis. A CD-relevant CD45RBhigh T cell transfer IBD representative animal model (Mottet et al., *J Immunol* 2003, 170:3939-43; Stepankova et al., *Inflamm Bowel Dis* 2007, 13:1202-11) has been adapted for the current studies. The animal experimental design using the T cell transfer model.

Characterization of drug distribution as well as BRD4 protein activity in vivo. The inventors will apply mass spectrometric imaging (MSI) to determine drug distribution. MSI is an analytical technique that provides 2-dimensional spatial maps of the distribution of the BRD4 inhibitor in mouse tissues (Lietz et al., *Adv Drug Deliv Rev* 2013, 65:1074-85; Greer et al., *J Proteomics* 2011, 74:2617-31). In brief, the distribution of BRD4 inhibitors can be determined in cryosectioned tissues using tandem mass spectrometry (MS). Tandem MS increases the confidence of identification of the inhibitors from other isobaric species in the tissue (Troendle et al., *Journal of the American Society for Mass Spectrometry* 1999, 10:1315-1321). The spectra are acquired in a grid-like pattern and converted into a 2-dimensional distribution across the tissue section, allowing a map of BRD4 inhibitor distribution. Freshly sectioned mice tissues from mouse models subjected to increasing concentrations of ZL0516 and ZL0590 will be subjected to MSI. Relative quantitation will be performed using stable isotopic standards spotted in increasing concentration onto the tissue sections (Nilsson et al., *PLoS One* 2010, 5, e11411). To determine the relationship of BRD4 inhibitor concentration to BRD4 activity in vivo, the inventors will conduct spatially resolved selected reaction monitoring (SRM) for biomarkers of BRD4 activity. For this purpose, H3K122ac will be measured, an acetylation mark mediated by BRD4, and HEXIM1, a protein that is induced by BRD4 inhibition, regarded as the gold standard of BRD4 inhibitory effect. In this experiment, mouse tissues will be sprayed with trypsin, and the proteotypic peptides for H3K122ac and HEXIM1 will be measured by tandem MS. Stable isotopic standards for H3K122ac and HEXIM will enable relative quantification. Using this advanced MSI, the inventors will be able to determine distributions of ZL0516 and ZL0590, their relative concentration in colonic tissue in normal and inflamed mucosa, and their relationship to BRD4 target activity. This will enable the understanding of the mucosal uptake and effect of the inhibitors in vivo.

Development of BRD4 inhibitor-loaded nanoparticles for targeted therapy to areas of active colonic inflammation. Encapsulation of the BRD4 inhibitors ZL0516 and ZL0590 in nanoparticles designed to bind to actively inflamed epithelium and release their contents in the colon is expected to direct the therapy to the site of inflammation and reduce systemic side effects. This is especially vital in UC, which is associated with reduced colonic transit times (Amidon et al., *AAPS PharmSciTech* 2015, 16:731-41). Four approaches will guide the design of colon-targeted nanoparticles: (A) The nanoparticle matrix will be comprised of the biodegradable and biocompatible polymer poly(ε-caprolactone), which is resistant to acid degradation in the stomach, but polymer degradation and drug release can be promoted by the action of lipases at the site of inflammation. (B) Polysaccharides resistant to gastric and intestinal enzymes but which are metabolized by anaerobic bacteria in the colon will be used to coat the nanoparticle surfaces, thereby restricting premature particle degradation. (C) Nanoparticle diameter will be optimized, as smaller particles have higher tissue binding compared to larger particles, and loss of mucous-gel layers at sites of mucosal inflammation allows for preferential accumulation of nanoparticles by enterocytes and macrophages. (D) The expression of ICAM-1 is upregulated in inflamed cells of the colon, so peptides targeting ICAM-1 will be chemically conjugated to the poly(ε-caprolactone) nanoparticle matrix to enhance the accumulation of the nanoparticles at the site of inflammation. Polymeric nanoparticles comprised of poly(lactic acid), poly(ε-caprolactone), and polyethylene glycol conjugated with an ICAM-1-targeting peptide have been previously synthesized. These targeted nanoparticles showed higher uptake in inflamed primary human pulmonary microvascular endothelial cells, which expressed greater levels of ICAM-1 as compared to non-inflamed cells. The DMPK profiles of these ZL0516 and ZL0590-loaded nanoparticles will be assessed, and compared with the parental drugs.

Characterization of the in vivo efficacy of BRD4-inhibitor loaded nanoparticles in IBD models and analyze the drug concentration/distribution. In vivo efficacy of BRD4 inhibitor-loaded nanoparticles will be evaluated in models of DSS-induced and oxa-induced chronic colitis as well as T cell transfer model. BRD4 inhibitor-loaded nanoparticles will be administrated orally (p.o.) at increasing dosages (0.08, 0.4, and 2 mg/kg) after the initiation of inflammation. Inflammatory and fibrotic responses of treated mice will be examined using histopathological, immunological, cellular, and molecular approaches. Fibrosis will be examined by quantification of myofibroblast expansion, smooth muscle hypertrophy and extracellular matrix deposition. The drug concentration/tissue distribution of the BRD4 inhibitors following nanoparticle administration will be compared to the drug distribution following dosing of the inhibitors without nanoparticles to assess the efficiency of the nanoparticle-based drug targeting strategy. This will be performed using MSI.

Figure 11:
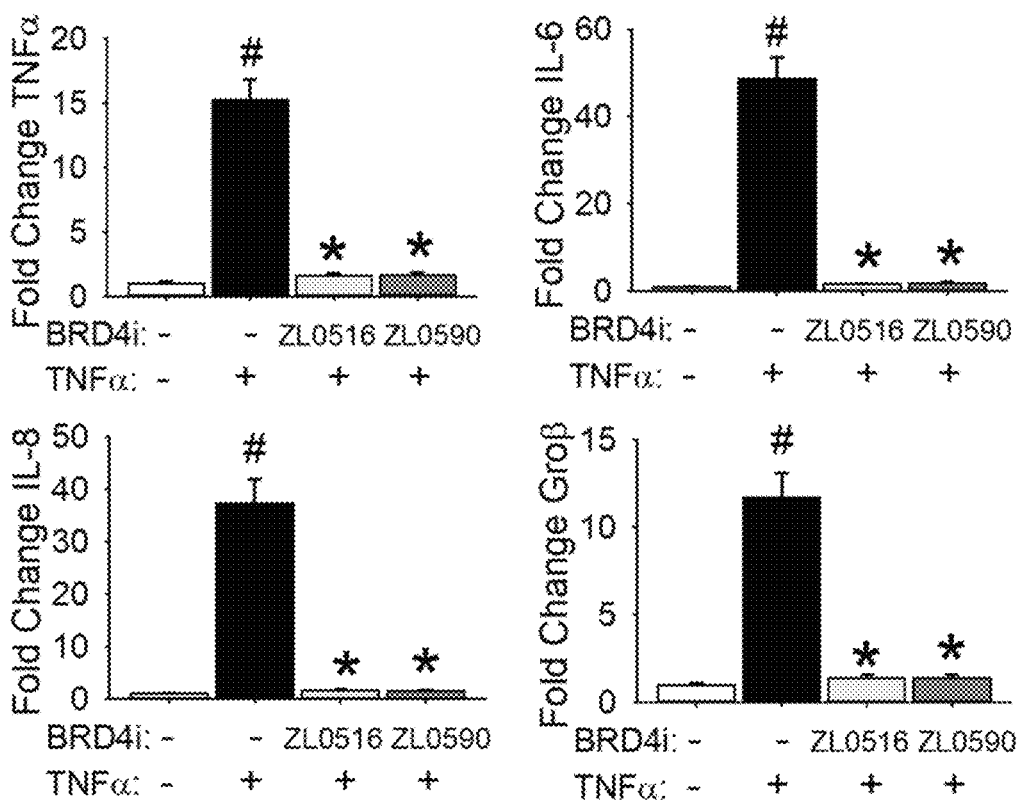
FIG. 11. TNFα-induced expressions of NFκB dependent inflammatory cytokines are inhibited by BRD4 inhibitors ZL0516 & ZL0590 in HCECs. Human colonic epithelial cells (HCECs) were preincubated with or without ZL0516 and ZL0590 (10 µM) were stimulated with or without TNFα (20 µg/mL, 1 h). Expression levels of epithelial NFκB-dependent genes were determined by qRT-PCR. The fold change relative to control is shown for each gene (Mean±SD, n=3), # $p<0.01$, compared to control, * $p<0.01$ compared with TNFα only.
Figure 12A:
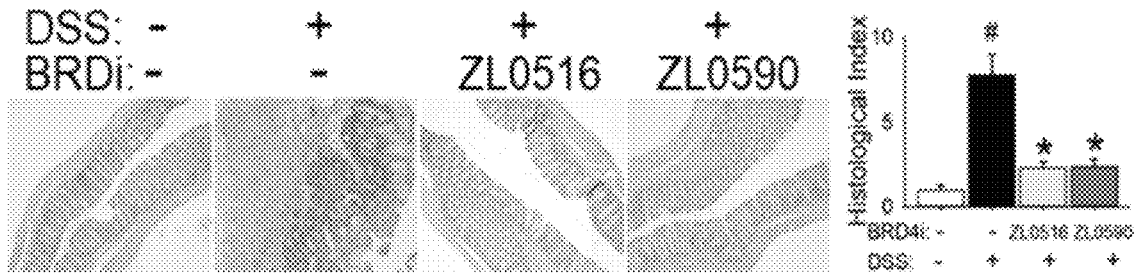
FIGS. 12A-B BRD4 inhibitors ZL0516 & ZL0590 blocked DSS-induced Colitis. (A). BRD4 inhibitors block colonic inflammation. Three groups of mice were given 3% DSS (p.o.) for 10 days. Two DSS-treated groups were also given BRD4 inhibitor ZL0516 or ZL0590 (10 mg/kg, ip.) daily. Left, H&E analysis, right, histological index, # $p<0.01$, compared to control, * $p<0.01$, compared to DSS only, n=5. (B). NFκB downstream inflammatory cytokines are activated in DSS colitis and inhibited in vivo by BRD4 inhibitors. qRT-PCR analysis of mRNA expression in colonic mucosa. The fold change relative to control is shown. # $p<0.01$, compared to control, * $p<0.01$, compared to DSS only, n=5.
Figure 12B:
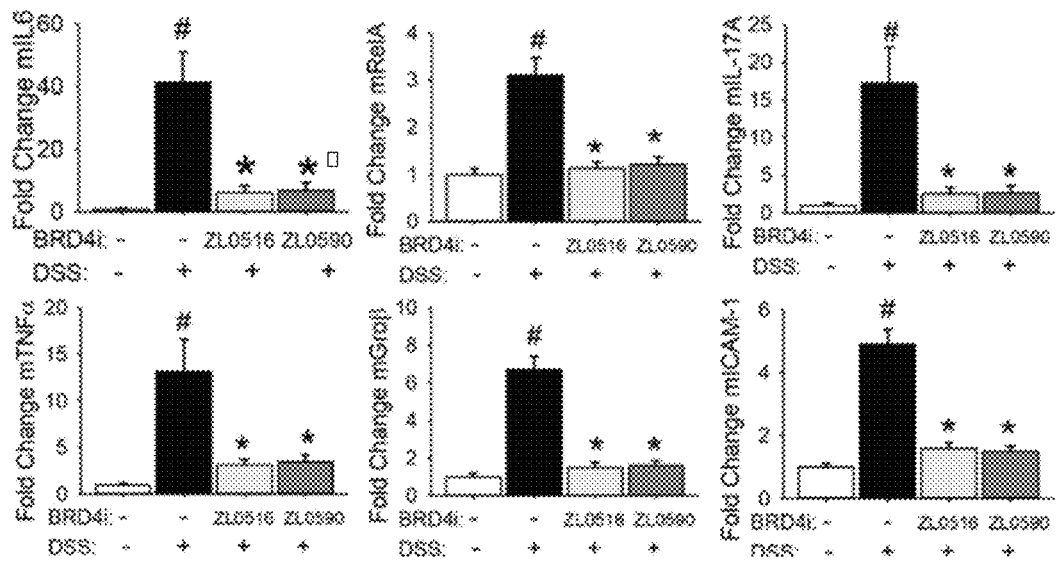
Figure 13:
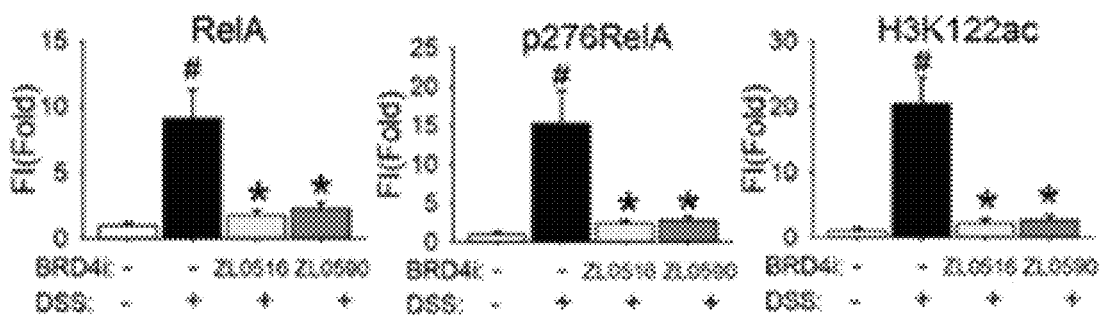
FIG. 13. BRD4 inhibitors block DSS-induced activation of NFκB-BRD4 pathway in colons of mice indicated by immunofluorescence staining. Top two panels, NFκB activation: IF of RelA and p276 RelA; nuclear staining (DAPI). The third panel, H3K122 acetylation. Bottom, quantifications of total fluorescence intensities (using Image J). # $p<0.01$, compared to control, * $p<0.01$, compared to DSS only, n=5.

TNFα-induced expressions of NFκB dependent inflammatory cytokines are inhibited by BRD4 inhibitors ZL0516 and ZL0590 in HCECs. Human colonic epithelial cells (HCECs) were preincubated with or without ZL0516 and ZL0590 (10 μM) were stimulated with or without TNFα (20 μg/mL, 1 h). Expression levels of epithelial NFκB-dependent genes were determined by qRT-PCR. The fold change relative to control is shown for each gene (Mean±SD, n=3), # p<0.01, compared to control, *p<0.01 compared with TNFα only (FIG. 11). BRD4 inhibitors ZL0516 and ZL0590 blocked DSS-induced Colitis. (FIG. 12A) BRD4 inhibitors block colonic inflammation. Three groups of mice were given 3% DSS (p.o.) for 10 days. Two DSS-treated groups were also given BRD4 inhibitor ZL0516 or ZL0590 (10 mg/kg, ip.) daily. Left, H&E analysis, right, histological index, # p<0.01, compared to control, *p<0.01, compared to DSS only, n=5. (FIG. 12B). NFκB downstream inflammatory cytokines are activated in DSS colitis and inhibited in vivo by BRD4 inhibitors. qRT-PCR analysis of mRNA expression in colonic mucosa. The fold change relative to control is shown. # p<0.01, compared to control, *p<0.01, compared to DSS only, n=5 (FIG. 12. BRD4 inhibitors block DSS-induced activation of NFκB-BRD4 pathway in colons of mice indicated by immunofluorescence staining (FIG. 13).

TABLE 8

Binding affinities (IC50, nM) of selected BRD4 inhibitors of bromodomains(BDs) and selectivity in comparison with JQ1 and RVX-208.

| $IC_{50}$ (μM) | JQ1 | RVX-208 | ZL0420 | ZL0454 | ZL0590 | ZL0591 | ZL0516 |
|---|---|---|---|---|---|---|---|
| BRD4 (BD1) | 92 | 1,142 | 27 | 49 | 93 | 96 | 84 |
| BRD4 (BD2) | 62 | 135 | 32 | 32 | 1,050 | 1,170 | 718 |
| BRD2 (BD1) | 78 | 5,780 | 803 | 772 | 824 | 729 | 866 |
| BRD2 (BD2) | 52 | 251 | 1,736 | 1,836 | 1,276 | 1,345 | 914 |
| BRD3 (BD1) | 81 | 3,962 | 2,275 | 2,493 | 2,265 | 2,083 | 3,122 |
| BRD3 (BD2) | 69 | 203 | 2,193 | 2,241 | 2,014 | 1,936 | 2,495 |
| BRDT (BD1) | 183 | 4,836 | 3,183 | 3,292 | 2,349 | 2,186 | 3,592 |
| BRDT (BD2) | 217 | 708 | 2,781 | 3,082 | 1,863 | 1,945 | 3,176 |
| CBP | 9,600 | >10,000 | >10,000 | >10,000 | >10,000 | >10,000 | >10,000 |

TABLE 9

Binding affinities ($IC_{50}$, nM) of advanced lead BRD4 inhibitors ZL0590, ZL0591, ZL0516, and negative control ZL0497 to bromodomains and gene-expression inhibitory activities.

| $IC_{50}$ values (in nM) | | ZL0590 | ZL0591 | ZL0516 | ZL0497 |
|---|---|---|---|---|---|
| Binding affinities for bromodomains | BRD4-BD1 | 93 | 96 | 84 | >10,000 |
| | BRD4-BD2 | 1,050 | 1,170 | 718 | >10,000 |
| | BRD2-BD1 | 824 | 729 | 886 | >10,000 |
| | BRD2-BD2 | 1,276 | 1,345 | 914 | >10,000 |
| | BRD3 (BD1) | 2,265 | 2,083 | 3,122 | >10,000 |
| | BRD3 (BD2) | 2,014 | 1,936 | 2,495 | >10,000 |
| | BRDT (BD1) | 2,349 | 2,186 | 3,592 | >10,000 |
| | BRDT (BD2) | 1,863 | 1,945 | 3,176 | >10,000 |
| | CBP | >10,000 | >10,000 | >10,000 | >10,000 |
| Gene-expression inhibition | hSAECs (IL-6) | 390 | 240 | 310 | >10,000 |
| | hSAECs (CIG5) | 180 | 400 | 280 | >10,000 |

The invention claimed is:

1. A compound, or a pharmaceutically acceptable salt thereof, having Formula III:

Formula III

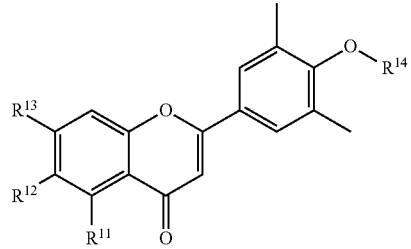

wherein:

$R^{11}$, $R^{12}$, and $R^{13}$ are independently H, —OH, halogen, alkoxy, —NH$_2$, —CF$_3$, —(CO)R$^{17}$ where R$^{17}$ is alkyl, alkoxy, amino, or alkylamino;

$R^{14}$ is a C1-4 alkyl substituted with one or more of OH, alkoxy, amino, alkylamino, or an unsubstituted 5-6 membered heterocycle with 1-3 heteroatoms.

2. The compound of claim 1, wherein the compound is selected from compound having a structure of

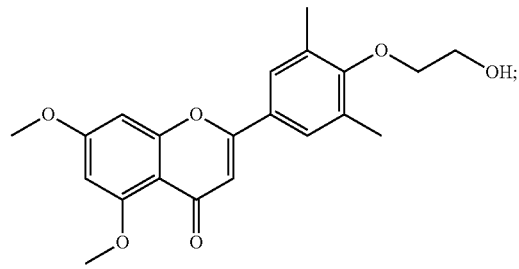

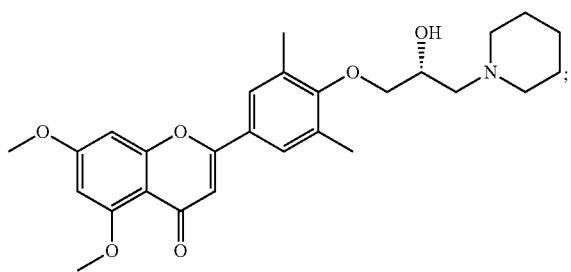

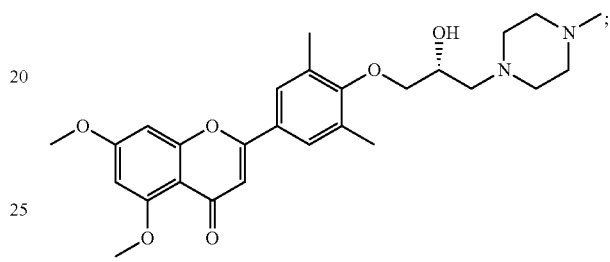

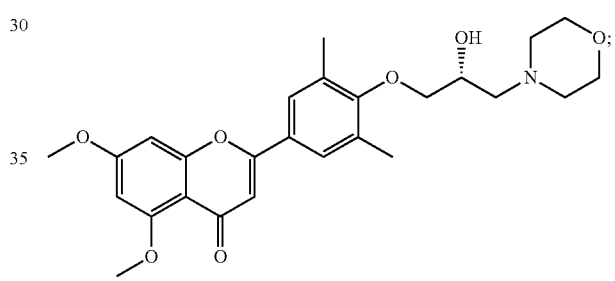

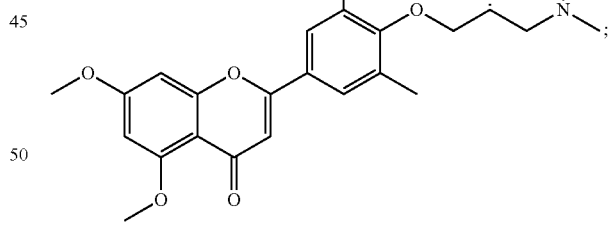

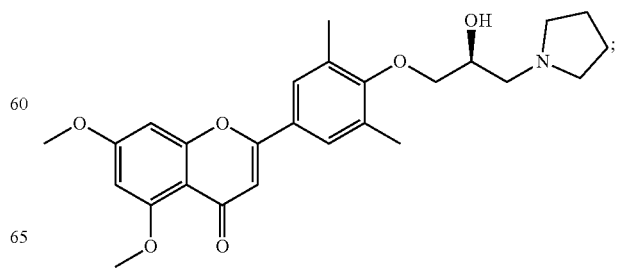

-continued

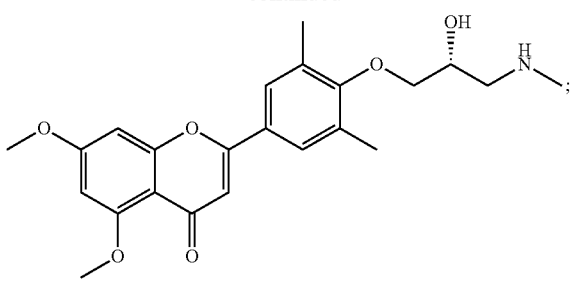

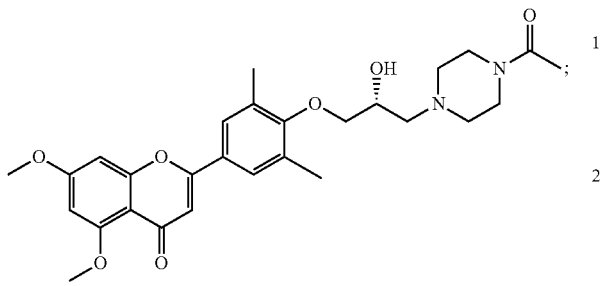

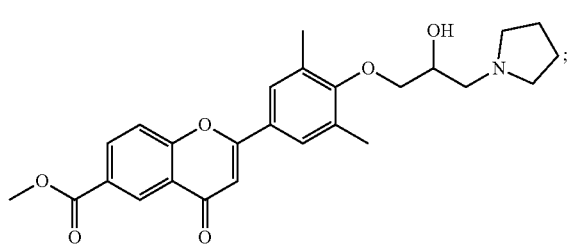

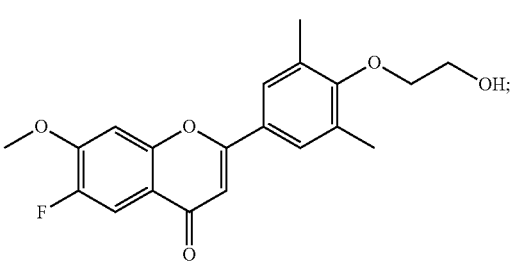

-continued

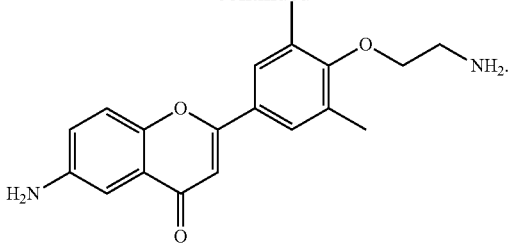

3. The compound of claim 2, wherein the compound has a structure of;

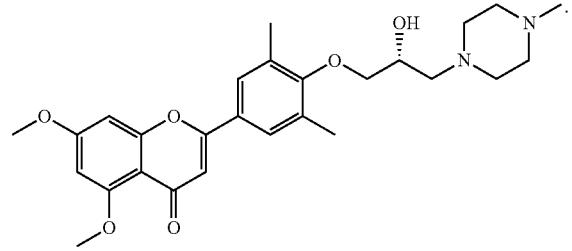

4. A compound, or a pharmaceutically acceptable salt thereof, having the Formula IIIa:

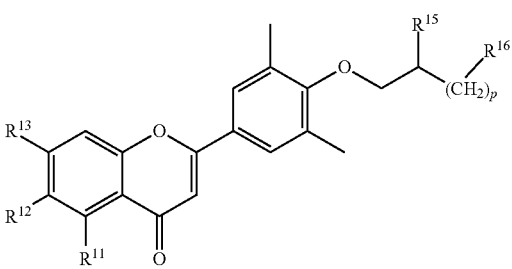

Formula IIIa wherein:
$R^{11}$, $R^{12}$, and $R^{13}$ are independently H, —OH, halogen, alkoxy, —NH$_2$, —CF$_3$, —(CO)R$^{17}$ where R$^{17}$ is alkyl, alkoxy, amino, or alkylamino;
$R^{15}$ is H, —OH, alkyl, or NH$_2$;
p is 0-4;
$R^{16}$ is H, —OH, alkyl, alkoxy; or —NR$^{18}$R$^{19}$ where R$^{18}$ and R$^{19}$ are independently H, alkyl; or R$^{18}$ and R$^{19}$ are optionally joined to form a 3-6 membered substituted or unsubstituted heterocycle having 1-3 heteroatoms;
wherein at least one of $R^{11}$, $R^{12}$, or $R^{13}$ is —OH, halogen, alkoxy, —NH$_2$, —CF$_3$, —(CO)R$^{17}$ when R$^{15}$ is H, and R$^{16}$ is H or alkyl.

\* \* \* \* \*